US008519118B2

(12) United States Patent
Czech et al.

(10) Patent No.: US 8,519,118 B2
(45) Date of Patent: *Aug. 27, 2013

(54) RIP140 REGULATION OF GLUCOSE TRANSPORT

(75) Inventors: Michael P. Czech, Westborough, MA (US); Aimee Powelka, Framingham, MA (US); Adilson L. Guilherme, Shrewsbury, MA (US); Andrew D. Cherniack, Worcester, MA (US)

(73) Assignee: University of Massachusetts, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/345,390

(22) Filed: Jan. 6, 2012

(65) Prior Publication Data

US 2012/0208862 A1 Aug. 16, 2012

Related U.S. Application Data

(63) Continuation of application No. 12/575,981, filed on Oct. 8, 2009, now Pat. No. 8,093,223, which is a continuation of application No. 11/075,646, filed on Mar. 7, 2005, now Pat. No. 7,691,823.

(60) Provisional application No. 60/550,677, filed on Mar. 5, 2004.

(51) Int. Cl.
*C07H 21/04* (2006.01)

(52) U.S. Cl.
USPC ......... 536/24.5; 536/24.1; 536/24.31; 514/44

(58) Field of Classification Search
None
See application file for complete search history.

(56) References Cited

U.S. PATENT DOCUMENTS

| 6,346,374 B1 | 2/2002 | Tartaglia et al. |
| 2002/0119499 A1 | 8/2002 | Taniguchi et al. |
| 2005/0059007 A1 | 3/2005 | Czech et al. |

FOREIGN PATENT DOCUMENTS

WO WO 02/33046 4/2002

OTHER PUBLICATIONS

Aranda et al., "Nuclear Hormone Receptors and Gene Expression," *Physiol. Rev.*, 81(3):1269-1304 (2001).
Bernal-Mizrachi et al., "Dexamethasone induction of hypertension and diabetes is PPAR-α dependent in LDL receptor-null mice," *Nat. Med.*, 9(8):1069-1075 (Jul. 6, 2003).
Bernlohr et al., "Expression of specific mRNAs during adipose differentiation: Identification of an mRNA encoding a homologue of myelin P2 protein," *Proc. Nat. Acad. Sci. USA*, 81(17):5468-5472 (1984).
Cain et al., "Members of the VAMP Family of Synaptic Vesicle Proteins Are Components of Glucose Transporter-containing Vesicles from Rat Adipocytes," *J. Biol. Chem.*, 267(17):11681-11684 (1992).
Chinnadurai, "CtBP family proteins: more than transcriptional corepressors," *BioEssays*, 25(1):9-12 (2003).
Christian et al., "Characterization of Four Autonomous Repression Domains in the Corepressor Receptor Interacting Protein 140," *J Biol. Chem.*, 279(15):15645-15651 (Jan. 2004).
Czech et al., "Signaling Mechanisms That Regulate Glucose Transport," *J Biol. Chem.*, 274(4):1865-1868 (1999).
Davignon et al., "Gene Structure of Murine *Gna11* and *Gna15*: Tandemly Duplicated Gq Class G Protein α Subunit Genes," *Genomics*, 31:359-366 (1996).
DiGirolamo et al., "Metabolic patterns and insulin responsiveness of enlarging fat cells," *J. Lipid Res.*, 15:332-3388 (1974).
Elmendorf et al., "Insulin Signaling Regulating the Trafficking and Plasma Membrane Fusion of GLUT4-Containing Intracellular Vesicles," *Exp. Cell Res.*, 253(1):55-62 (1999).
Farooqui et al., "Effects of Retinoid Ligands on RIP140: Molecular Interaction with Retinoid Receptors and Biological Activity," *Biochemistry*, 42(4):971-979 (2003).
Frost et al., "Evidence for the Involvement of Vicinal Sulfhydryl Groups in Insulin-activated Hexose Transport by 3T3-L1 Adipocytes," *J. Biol. Chem.*, 260(5):2646-2652 (1985).
GenBank Accession No. AF248484, 56 pages (Apr. 4, 2000).
GenBank Accession No. AV272221, 3 pages (Nov. 5, 1999).
GenBank Accession No. NM_003489, 8 pages (Mar. 24, 1999).
GenBank Accession No. NM_008735, 4 pages (Jan. 6, 2000).
GenBank Accession No. NM_173440, 4 pages (Jan. 14, 2003).
GenBank Accession No. NP_003480, 5 pages (Mar. 24, 1999).
GenBank Accession No. NP_005027, 18 pages (May 14, 1999).
GenBank Accession No. NP_775616, 3 pages (Jan. 14, 2003).
GenBank Accession No. P37231, 12 pages (Oct. 1, 1994).
GenBank Accession No. Q03181, 8 pages (Nov. 18, 2003).
Hart et al., "The estrogen receptor: more than the average transcription factor," *Biochem. Cell Biol.*, 80(3):335-341 (2002).
Hassan et al., "Promoter targeting of chromatin-modifying complexes," *Front. Biosci.*, 6:d1054-1064 (2001).
Heery, "A signature motif in transcriptional co-activators mediates binding to nuclear receptors," *Nature*, 387:733-736 (1997).
Heller-Harrison et al., "Insulin-mediated Targeting of Phosphatidylinositol 3-Kinase to GLUT4-containing Vesicles," *J. Biol. Chem.*, 271(17):10200-10204 (1996).
Hu et al., "AdipoQ is a Novel Adipose-specific Gene Dysregulated in Obesity," *J. Biol. Chem.*, 271(18):10697-10703 (1996).
Hu et al., "Suppressive Effect of Receptor-interacting Protein 140 on Coregulator Binding to Retinoic Acid Receptor Complexes, Histone-modifying Enzyme Activity, and Gene Activation," *J. Biol. Chem.*, 279(1):319-325 (2004).
Johnson et al., "A Di-Leucine Sequence and a Cluster of Acidic Amino Acids Are Required for Dynamic Retention in the Endosomal Recycling Compartment of Fibroblasts," *Mol. Biol. Cell*, 12(2):367-381 (2001).
Johnson et al., "Identification of an Insulin-responsive, Slow Endocytic Recycling Mechanism in Chinese Hamster Ovary Cells," *J. Biol. Chem.*, 273(28):17968-17977 (1998).

(Continued)

*Primary Examiner* — Kimberly Chong
(74) *Attorney, Agent, or Firm* — Fish & Richardson P.C.

(57) ABSTRACT

Inhibition of RIP140 increases glucose transport. Compounds that inhibit RIP140 expression or activity are useful for treating disorders associated with aberrant glucose transport (e.g., diabetes), treating obesity, increasing metabolism (e.g., fatty acid metabolism), and increasing brown fat.

19 Claims, 18 Drawing Sheets

(56) References Cited

OTHER PUBLICATIONS

Kandror et al., "Comparison of glucose-transporter-containing vesicles from rat fat and muscle tissues: evidence for a unique endosomal compartment," *Biochem. J.*, 307:383-390 (1995).

Kandror et al., "Compartmentalization of protein traffic in insulin-sensitive cells," *Am. J. Physiol. Endocrinol. Metab.*, 271(34):E1-E14 (1996).

Kandror et al., "The Insulin-like Growth Factor II/Mannose 6-Phosphate Receptor Utilizes the Same Membrane Compartments as GLUT4 for Insulin-dependent Trafficking to and from the Rat Adipocyte Cell Surface," *J. Biol. Chem.*, 271(36):21703-21708 (1996).

Koh et al., "Peroxisome Proliferator-Activated Receptor (PPAR)-α Activation Prevents Diabetes in OLETF Rats: Comparison With PPAR-γ Activation," *Diabetes*, 52:2331-2337 (2003).

Lampson et al., "Demonstration of insulin-responsive trafficking of GLUT4 and vpTR in fibroblasts," *J. Cell Sci.*, 113:4065-4076 (2000).

Lee et al., "Cloning and Characterization of Mouse RIP140, a Corepressor for Nuclear Orphan Receptor TR2," *Mol. Cell. Biol.*, 18(11):6745-6755 (1998).

Martin et al., "GLUT4 Trafficking in Insulin-Sensitive Cells: A Morphological Review," *Cell Biochem. Biophys.*, 30(1):89-113 (1999).

Martin et al., "The Glucose Transporter (GLUT-4) and Vesicle-associated Membrane Protein-2 (VAMP-2) are Segregated from Recycling Endosomes in Insulin-sensitive Cells," *J. Cell Biol.*, 134(3):625-635 (1996).

McDonnell et al., "Connections and Regulation of the Human Estrogen Receptor," *Science*, 296:1642-1644 (2002).

McKenna, "ENDO 2003: Malcolm Parker—RIP140 corepressor is a key regulator of ovulation and adipocyte function," NURSA e-Journal, vol. 1, No. 1, ID# 2.06242003.2 ISSN 1550-7629, 3 pages (2003).

Min et al., "Adipsin, the adipocyte serine protease: gene structure and control of expression by tumor necrosis factor," *Nucleic Acids Res.*, 14(22):8879-8892 (1986).

Mootha et al., "Errα and Gabpa/b specify PGC-1α-dependent oxidative phosphorylation gene expression that is altered in diabetic muscle," *Proc. Natl. Acad. Sci. USA*, 101(17):6570-6575 (2004).

Murphy et al., "PPAR-γ agonists: therapeutic role in diabetes, inflammation and cancer," *Trends Pharmacol. Sci.*, 21:469-474 (2000).

Nolte et al., "Ligand binding and co-activator assembly of the peroxisome proliferator-activated receptor-γ," *Nature*, 395:137-143 (1998).

Ntambi et al., "Differentiation-induced Gene Expression in 3T3-L1 Preadipocytes," *J. Biol. Chem.*, 263(33):17291-17300 (1988).

Parker et al., "Identification of RIP140 as a nuclear receptor cofactor with a role in female reproduction," *FEBS Letters*, 546:149-153 (2003).

Privalsky, "The Role of Corepressors in Transcriptional Regulation by Nuclear Hormone Receptors," *Annu. Rev. Physiol.*, 66:315-360 (2004).

Qi et al., "Peroxisome Proliferator-Activated Receptors, Coactivators, and Downstream Targets," *Cell Biochem. Biophys.*, 32:187-204 (2000).

Remillard et al., "Linking Dioxins to Diabetes: Epidemiology and Biologic Plausibility," *Environ. Health Perspect.*, 110(9):853-858 (Jul. 17, 2002).

Schreiber et al., "The estrogen-related receptor α (ERRα) functions in PPARγ coactivator 1α (PGC-1α)-induced mitochondrial biogenesis," *Proc. Natl. Acad. Sci. USA*, 101(17):6472-6477 (2004).

Subtil et al., "Characterization of the Insulin-regulated Endocytic Recycling Mechanism in 3T3-L1 Adipocytes Using a Novel Reporter Molecule," *J. Biol. Chem.*, 275(7):4787-4795 (2000).

Tamori et al., "Role of Peroxisome Proliferator-Activated Receptor-γ in Maintenance of the Characteristics of Mature 3T3-L1 Adipocytes," *Diabetes*, 51:2045-2055 (2002).

Tiraby et al., "Acquirement of Brown Fat Cell Features by Human White Adipocytes," *J. Biol. Chem.*, 278(35):33370-33376 (2003).

van Bilsen et al., "Peroxisome proliferator-activated receptors: Lipid binding proteins controling gene expression," *Mol. Cell. Biochem.*, 239:131-138 (2002).

Vo et al., "Acetylation of Nuclear Hormone Receptor-Interacting Protein RIP140 Regulates Binding of the Transcriptional Corepressor CtBP," *Mol. Cell. Biol.*, 21(18):6181-6188 (2001).

Wei, "Retinoid Receptors and Their Coregulators," *Annu. Rev. Pharmacol. Toxicol.*, 43:47-72 (2003).

Weitzel et al., "Regulation of mitochondrial biogenesis by thyroid hormone," *Exp. Physiol.*, 88(1):121-128 (2003).

Wilson-Fritch et al., "Mitochondrial Biogenesis and Remodeling during Adipogenesis and in Response to the Insulin Sensitizer Rosiglitazone," *Mol. Cell. Biol.*, 23(3):1085-1094 (2003).

Wilson-Fritch et al., "Mitochondrial remodeling in adipose tissue associated with obesity and treatment with rosiglitazone," *J. Clin. Invest.*, 114(9):1281-1289 (2004).

Xu et al., "Structural basis for antagonist-mediated recruitment of nuclear co-repressors by PPARα," *Nature*, 415:813-817 (2002).

Zilliacus et al., "Regulation of Glucocorticoid Receptor Activity by 14-3-3-Dependent Intracellular Relocalization of the Corepressor RIP140," *Mol. Endo.*, 15(4):501-511 (2001).

Fig. 1 - Page 1 of 3
Sequences producing significant alignments with murine
RIP140 by BLAST search

| GenBank® GI No. | GenBank® Acc. No. | Organism |
| --- | --- | --- |
| 26331275 | AK036273.1 | Mus musculus |
| 27734109 | NM 173440.1 | Mus musculus |
| 38614216 | BC060232.1 | Mus musculus |
| 23499610 | AC117256.4 | Mus musculus |
| 3820493 | AF053062.1\|AF053062 | Mus musculus |
| 27671827 | XM 221724.1 | Rattus norvegicus |
| 37537280 | BS000013.1 | Pan troglodytes |
| 7717255 | AL163207.2\|HS21C007 | Homo sapiens |
| 7019596 | AF127577.2\|AF127577 | Homo sapiens |
| 7407668 | AF248484.1\|AF248484 | Homo sapiens |
| 25955638 | BC040361.1 | Homo sapiens |
| 4505454 | NM 003489.1 | Homo sapiens |
| 940538 | X84373.1\|HSRIP140 | H. sapiens |
| 26088404 | AK041348.1 | Mus musculus |
| 26351120 | AK084498.1 | Mus musculus |
| 26081847 | AK030495.1 | Mus musculus |
| 12860545 | AK020076.1 | Mus musculus |
| 39645072 | BC063719.1 | Xenopus laevis |
| 7717257 | AL163208.2\|HS21C008 | Homo sapiens |
| 37537281 | BS000014.1 | Pan troglodytes |
| 177170 | M97568.1\|HUM21SEQN | Human |
| 19743922 | NM 130854.1 | Homo sapiens |
| 19743918 | NM 002850.2 | Homo sapiens |
| 18158380 | AC099759.4 | Homo sapiens |
| 4508115 | AC005061.2 | Homo sapiens |
| 26104839 | AK088511.1 | Mus musculus |
| 3702283 | AC005788.1\|AC005788 | Homo sapiens |
| 11321861 | AL162212.12 | Human |
| 600816 | Z46728.1\|SC9910 | S.cerevisiae |
| 22776527 | AP004596.1 | Oceanobacillus iheyensis |
| 4753195 | AC007478.1\|AC007478 | Arabidopsis thaliana |

Fig. 1 Page 2 of 3

| 21665929 | AL627328.17 | Mouse |
|---|---|---|
| 22507262 | AC121915.2 | Mus musculus |
| 37182612 | AY358747.1 | Homo sapiens |
| 27358548 | AE016810.1 | Vibrio vulnificus |
| 24051511 | AE015148.1 | Shigella flexneri |
| 30040895 | AE016982.1 | Shigella flexneri |
| 1041358 | Z66515.1\|CER53 | Caenorhabditis elegans |
| 29150537 | AC018445.21 | Homo sapiens chromosome |
| 21930255 | AC112673.7 | Homo sapiens |
| 8810256 | AC009000.6 | Homo sapiens |
| 21535916 | AC090018.12 | Homo sapiens |
| 13422568 | AE005800.1 | Caulobacter crescentus |
| 16604088 | AC096576.3 | Homo sapiens |
| 26107941 | AE016760.1 | Escherichia coli |
| 27356674 | AC134236.3 | Oryza sativa |
| 16949651 | AC095043.3 | Homo sapiens |
| 21757027 | AK097323.1 | Homo sapiens cDNA |
| 516158 | L28709.1\|ECOCHAABC | Escherichia coli |
| 37991234 | AK121611.1 | Oryza sativa |
| 25709117 | AC108860.14 | Homo sapiens |
| 25141001 | AC113377.2 | Homo sapiens |
| 7019816 | AK000011.1 | Homo sapiens |
| 32985464 | AK100255.1 | Oryza sativa |
| 8894207 | AL138717.6 | Human |
| 10881117 | AC019230.5\|AC019230 | Homo sapiens |
| 42544001 | AC074034.19 | Homo sapiens |
| 1663711 | D90757.1 | Escherichia coli K12 |
| 1651596 | D90756.1 | Escherichia coli K12 |
| 37221178 | NM 015493.3 | Homo sapiens |
| 25901045 | AP005660.3 | Homo sapiens |
| 12514931 | AE005339.1\|AE005339 | Escherichia |

Fig. 1 Page 3 of 3

|          |                      | coli O157:H7          |
|----------|----------------------|-----------------------|
| 1787467  | AE000220.1|AE000220  | Escherichia coli K12  |
| 1787453  | AE000219.1|AE000219  | Escherichia coli K12  |
| 18855221 | AL626769.18          | Mouse                 |
| 14330253 | AL122035.6|CNS01DSY  | Human                 |
| 220593   | D00926.1|MUSS2L122   | Mus musculus          |
| 17298195 | AP004218.2           | Homo sapiens          |
| 7959302  | AB040951.1           | Homo sapiens          |
| 13361156 | AP002556.1           | Escherichia coli O157:H7 |
| 23132695 | AC098584.2           | Homo sapiens          |
| 24431910 | AC080037.11          | Homo sapiens          |
|          |                      |                       |
|          |                      |                       |

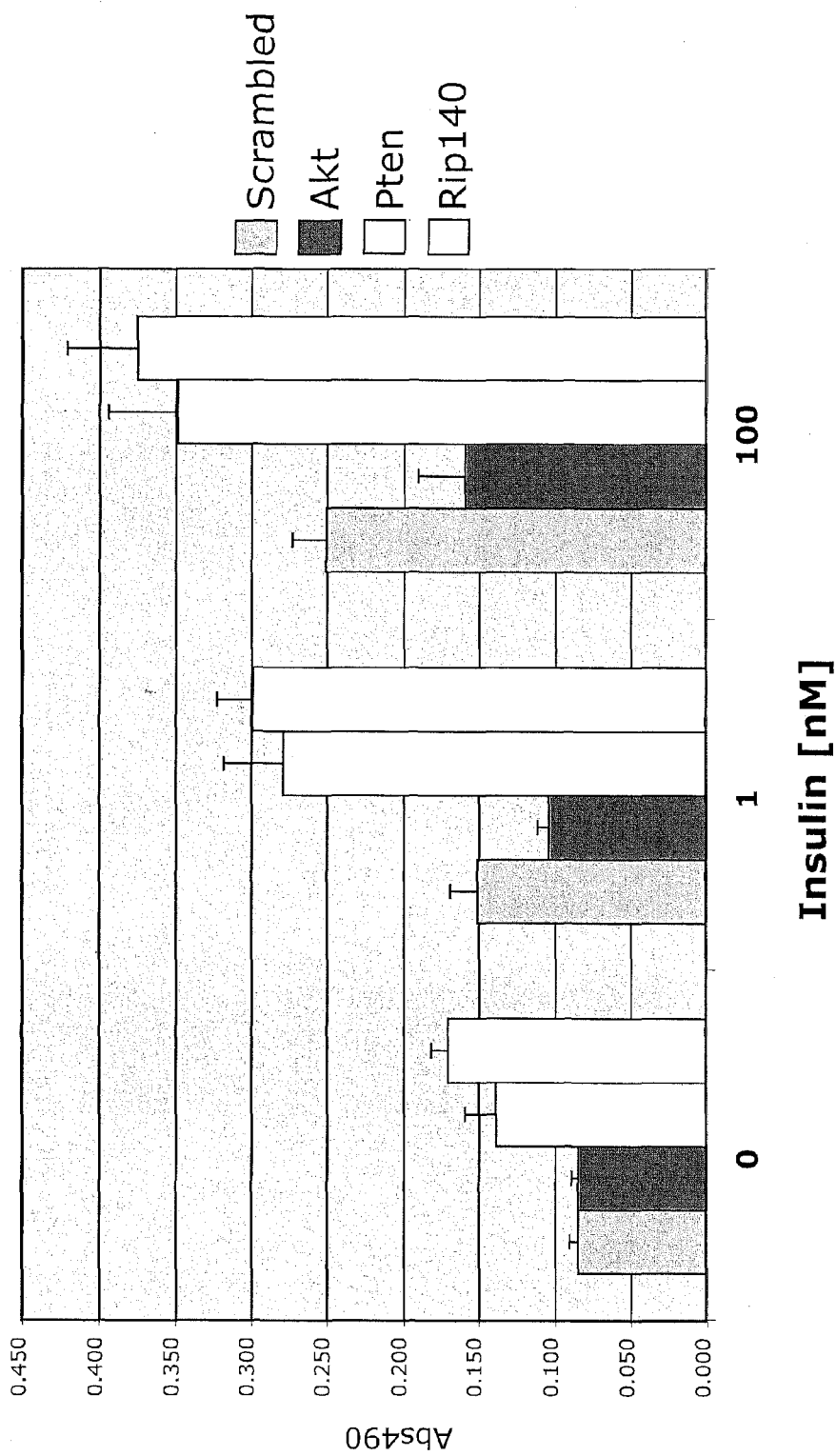
FIG. 2 Depletion of RIP140 Potentiates Insulin-Stimulated Akt Phosphorylation

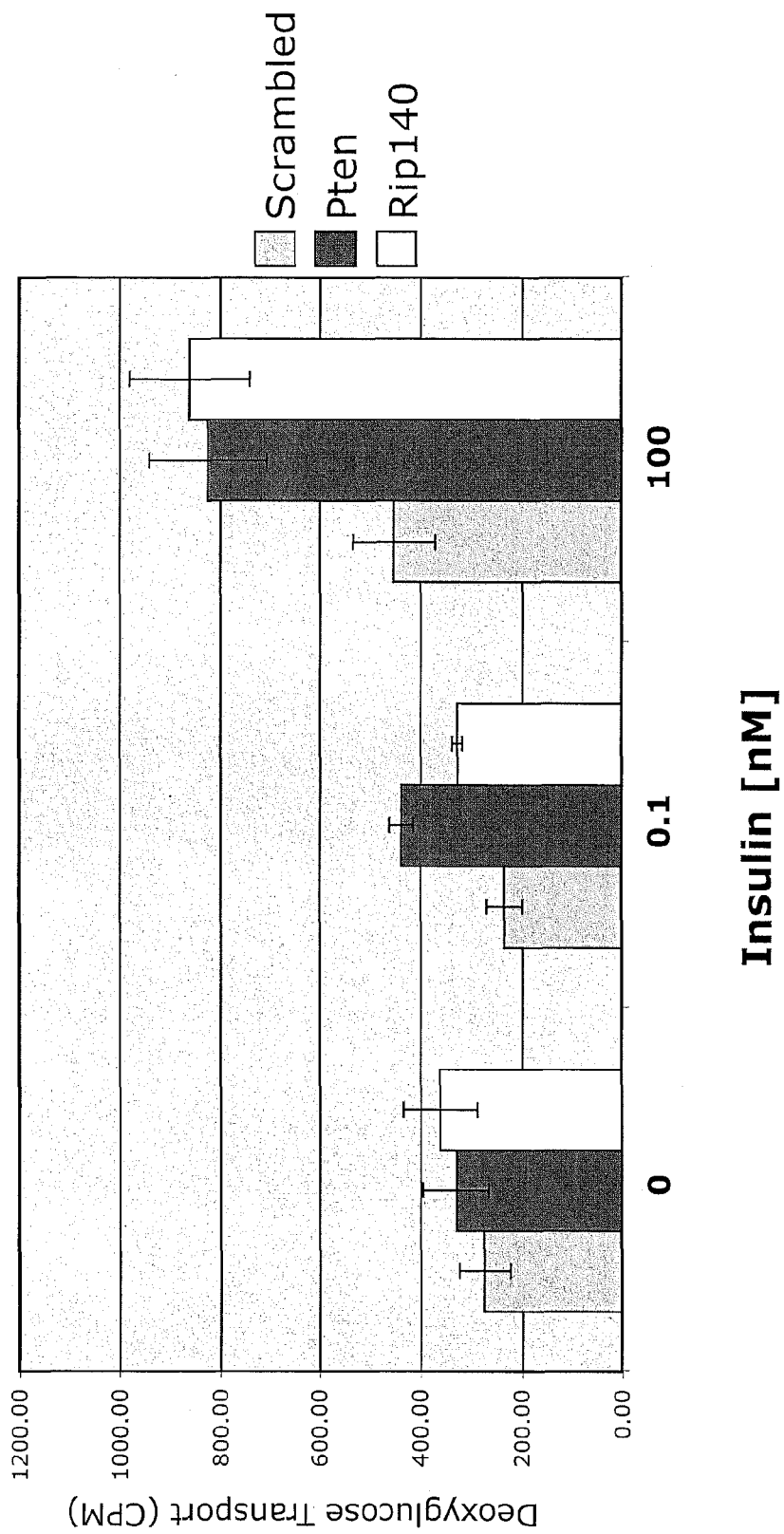
Fig. 3 Depletion of RIP140 Potentiates Insulin-Stimulated Deoxyglucose Transport FIG. 5 Choosing Gene Targets for siRNA-Mediated Screen: RIP140

| Probe Set ID | Gene Name | 26vsR26wk | | | 4vs26wk | | | FibvsAdip | | |
|---|---|---|---|---|---|---|---|---|---|---|
| | | FC | call | change | FC | call | change | FC | call | change |
| 110472_f_at | RIKEN cDNA D330024H06 gene | -1.05 | P | NC* | -2.05 | P | D | 4.81 | P | |
| 110296_at | cysteine conjugate-beta lyase | 1.35 | P* | NC* | 1.1 | NC | NC | 4.81 | A* | NC* |
| 104457_at | Mus musculus transcribed sequence | -1.1 | A | NC | -1.95 | A | NC | 4.81 | A* | NC* |
| 101991_at | flavin containing monooxygenase 1 | 1.59 | P | I | -2.96 | P | D | 4.81 | P | |
| 100464_at | RIKEN cDNA 3110043O21 gene | -1.17 | P | D | -1.62 | P | D | 4.81 | P | |
| 92820_at | RIKEN cDNA B930035K21 gene | -1.29 | A | NC | -1.15 | A | NC | 4.7 | A | NC |
| 133942_at | Mus musculus transcribed sequences | -1.29 | A | NC | -1.26 | A | NC | 4.7 | A* | NC* |
| 133276_r_at | --- | 1.59 | A* | NC | 1.2 | A | NC | 4.7 | A* | NC |
| 117161_at | expressed sequence AI987712 | 1.15 | P | NC | -2.09 | A* | NC* | 4.7 | A | NC |
| 116925_at | RIKEN cDNA 6130400H19 gene | 1.46 | A | NC | -1.87 | A | NC | 4.7 | A | NC |
| 115909_at | Mus musculus transcribed sequences | -1.12 | P | NC | -2.41 | P | D* | 4.7 | P | |
| 112095_at | RIKEN cDNA 1810059A23 gene | 2 | A | NC | -1.62 | A | NC | 4.7 | A | NC |
| 106456_at | RIKEN cDNA 2900056N03 gene | -1.38 | A | NC | -1.18 | A | NC | 4.7 | A | NC |
| 103741_at | homeo box D10 | -1.74 | A | NC | 1.05 | A | NC | 4.7 | A | NC |
| 103487_at | lymphocyte antigen 6 complex, locus H | 1.32 | A* | NC | -1.02 | A | NC | 4.7 | A | NC |
| 103288_at | nuclear receptor interacting protein | 1.12 | P | NC* | -6.5 | P | D* | 4.7 | P | |
| 102651_at | glucokinase | -1.41 | A | NC* | 2 | A | NC | 4.7 | A | NC* |
| 97198_at | ATP-binding cassette, sub-family A ... | 1.38 | P | I* | -1.38 | P | D* | 4.59 | A* | I* |
| 96913_at | hydroxyacyl-Coenzyme A dehydrogenase, beta sub | 1.48 | P | | -1.66 | P | D | 4.59 | P | |
| 94743_f_at | complement component factor h | -1.59 | P | NC | 2.05 | P | I* | 4.59 | A | NC |
| 92814_at | cytochrome P450, 2J5 | -2.24 | A | NC | 2 | A | NC* | 4.59 | A | NC |
| 92581_at | acetyl-Coenzyme A dehydrogenase, medium chain | 1.55 | P | I* | -1.82 | P | D | 4.59 | P | |
| 133342_at | Mus musculus transcribed sequence | 2.14 | A | NC | -5.53 | A | NC* | 4.59 | P | |
| 117262_at | RIKEN cDNA 2810435D12 gene | 2.3 | A | NC | -1.74 | A | NC | 4.69 | A | NC* |
| 116162_g_at | Musashi homolog 2 (Drosophila) | -1.18 | A | NC | -1.38 | P* | NC* | 4.59 | A* | NC |
| 115967_at | RIKEN cDNA 5630400M01 gene | 1.15 | A | NC | 1.7 | A* | NC | 4.59 | A* | NC |
| 112294_at | RAB3D, member RAS oncogene family | -1.18 | P | NC | -2.05 | P | D* | 4.59 | P | I* |
| 111974_at | Mus musculus transcribed sequences | -3.82 | A | NC | 1.02 | A | NC | 4.59 | A | NC |
| 109011_at | nuclear receptor interacting protein | 1.35 | P | NC | -2.7 | P | D | 4.59 | A* | I* |
| 111244_at | Mus musculus 16 days embryo head cDNA | 1.12 | P* | NC | -7.64 | P | D | 4.59 | P | |

| Affymetrix probe | Accession No. | Gene Name | Gene Symbol | Fold-Change | Call |
|---|---|---|---|---|---|
| 1418963_at | BC011118 | CCAAT/enhancer binding protein (C/EBP), alpha | Cebpa | -1.02603 | p |
| 1419536_at | NM_009883 | CCAAT/enhancer binding protein (C/EBP), beta | Cebpb | -1.247463 | p |
| 1422223_at | AK031146 | CCAAT/enhancer binding protein (C/EBP), delta | Cebpd | -1.24980 | p |
| 1425761_a_at | AK112273 | CCAAT/enhancer binding protein (C/EBP), gamma | Cebpg | -1.097830 | p |
| 1420497_s_at | NM_009982 | CCAAT/enhancer binding protein zeta | Cebpz | 1.017693 | p |
| 1421814_at | NM_007953 | estrogen related receptor, alpha | Esrra | -1.16204 | p |
| 1421825_s_at | BB3MC294 | estrogen-related receptor, beta | Esrrb | | p |
| 1421826_at | NM_009455 | estrogen-related receptor, beta like 1 | Esrrbl1 | | p |
| 1450685_at | NM_011933 | GA repeat binding protein, alpha | Gabpa | -1.144324 | p |
| 1453352_at | BQ771503 | GA repeat binding protein, beta 1 | Gabpb1 | -1.06902 | p |
| 1452632_at | AK033408 | GA repeat binding protein, beta 2 | Gabpb2 | -1.153276 | p |
| 1410452_at | BB323506 | Rev-ErbA alpha | | 1.055267 | p |
| 1416933_at | NM_011964 | LXR beta | Nr1h2 | | a |
| 1416604_a_at | NM_013839 | LXR alpha | Nr1h3 | -1.176448 | p |
| 1416169_at | NM_010150 | COUP-TFII beta | Nr2f2 | 1.226426 | p |
| 1448515_at | NM_010444 | EAR2 | Nr2f6 | -3.508268 | a |
| 1426734_at | BB703394 | Nurr1 | Nr4a1 | -1.322397 | p |
| 1417088_s_at | NM_026297 | nuclear receptor binding factor 1 | Nrbf1 | -1.05919 | a |
| 1448735_at | NM_026907 | nuclear receptor binding factor 2 | Nrbf2 | -1.03054 | a |
| 1423671_at | BF202218 | nuclear receptor binding protein | Nrbp | -1.02693 | p |
| 1424757_a_at | BC006410 | nuclear respiratory factor 1 | Nrf1 | -3.535256 | a |
| 1431810_at | NM_008923 | nuclear receptor interacting protein 1 | Nrip1 | -1.14203 | p |
| 1451787_s_at | AW020731 | nuclear receptor interacting protein 3 | Nrip3 | 1.24777 | p |
| 1425345_at | A514189 | progesterone receptor membrane component 1 | Pgrmc1 | | p |
| 1423571_at | BF727450 | progesterone receptor membrane component 2 | Pgrmc2 | | p |
| 1439661_at | BC019089 | peroxisome proliferator activated receptor alpha | Ppara | -1.06319 | p |
| 1416789_at | NM_134027 | peroxisome proliferator activated receptor delta | Ppard | -1.543764 | p |
| 1420715_s_at | NM_011146 | PPAR gamma, coactivator 1 alpha | Ppargc1a | -1.012487 | p |
| 1430416_at | BB107641 | PPAR gamma, coactivator 1 beta | Ppargc1b | -1.056951 | p |
| 1425762_a_at | U77845 | retinoid X receptor alpha | Rxra | -1.244918 | p |
| 1416690_s_at | NM_009025 | retinoid X receptor gamma | Rxrg | 1.146013 | p |
| 1416762_at | NM_011375 | sterol regulatory element binding factor 1 | Srebf1 | -1.130069 | p |
| 1449640_s_at | AJ276423 | sterol regulatory element binding factor 2 | Srebf2 | -1.153569 | p |
| 1441118_at | BM173552 | Repression factor A, mitochondria | Tfam | 1.013281 | p |
| 1436215_at | BB469709 | transcription factor B1, mitochondrial | Tfb1m | 1.046024 | p |
| 1452424_at | AV301315 | transcription factor B2, mitochondrial | Tfb2m | 1.197788 | p |
| 1422343_at | AV095126 | thyroid hormone receptor alpha | Thra | -1.02188 | p |
| 1454878_at | BE285499 | | | | p |

Figure 11

FIGURE 12A - page 1 of 3

```
   1 aacactgata tttgcattta atggggaaca aaagatgaag aaggaaaagg aatatattca
  61 ctaaggattc tatctgctta ctgctacaga cctatgtgtt aaggaattct tctcctcctc
 121 cttgcgtaga agttgatcag cactgtggtc agactgcatt tatcttgtca ttgccagaag
 181 aaatcttgga cagaatgtaa cagtacgtct ctctctgatt gcgatggaag gtgataaact
 241 gatactcctt tattaaagtt acatcgcact caccacagaa aaccattctt taaagtgaat
 301 agaaaccaag cccttgtgaa cacttctatt gaacatgact catggagaag agcttggctc
 361 tgatgtgcac caggattcta ttgttttaac ttacctagaa ggattactaa tgcatcaggc
 421 agcaggggga tcaggtactg ccgttgacaa aaagtctgct gggcataatg aagaggatca
 481 gaactttaac atttctggca gtgcatttcc cacctgtcaa agtaatggtc cagttctcaa
 541 tacacataca tatcaggggt ctggcatgct gcacctcaaa aaagccagac tgttgcagtc
 601 ttctgaggac tggaatgcag caaagcggaa gaggctgtct gattctatca tgaatttaaa
 661 cgtaaagaag gaagctttgc tagctggcat ggttgacagt gtgcctaaag caaacagga
 721 tagcacatta ctggcctctt tgcttcagtc attcagctct aggctgcaga ctgttgctct
 781 gtcacaacaa atcaggcaga gcctcaagga gcaaggatat gccctcagtc atgattcttt
 841 aaaagtggag aaggatttaa ggtgctatgg tgttgcatca agtcacttaa aaactttgtt
 901 gaagaaaagt aaagttaaag atcaaaagcc tgatacgaat cttcctgatg tgactaaaaa
 961 cctcatcaga gataggtttg cagagtctcc tcatcatgtt ggacaaagtg aacaaaggt
1021 catgagtgaa ccgttgtcat gtgctgcaag attacaggct gttgcaagca tggtggaaaa
1081 aagggctagt cctgccacct cacctaaacc tagtgttgct tgtagccagt tagcattact
1141 tctgtcaagc gaagcccatt tgcagcagta ttctcgagaa cacgctttaa aaacgcaaaa
1201 tgcaaatcaa gcagcaagtg aaagacttgc tgctatggcc agattgcaag aaaatggcca
1261 gaaggatgtt ggcagttacc agctcccaaa aggaatgtca agccatctta atggtcaggc
1321 aagaacatca tcaagcaaac tgatggctag caaaagtagt gctacagtgt ttcaaaatcc
1381 aatgggtatc attccttctt cccctaaaaa tgcaggttat aagaactcac tggaaagaaa
1441 caatataaaa caagctgcta caaatagttt gcttttacat cttcttaaaa gccagactat
1501 acctaagcca atgaatggac acagtcacag tgagagagga agcattttg aggaaagtag
1561 tacacctaca actattgatg aatattcaga taacaatcct agttttacag atgacagcag
1621 tggtgatgaa agttcttatt ccaactgtgt tcccatagac ttgtcttgca aacaccgaac
1681 tgaaaaatca gaatctgacc aacctgtttc cctggataac ttcactcaat ccttgctaaa
1741 cacttgggat ccaaaagtcc cagatgtaga tatcaaagaa gatcaagata cctcaaagaa
1801 ttctaagcta aactcacacc agaaagtaac acttcttcaa ttgctacttg gccataagaa
1861 tgaagaaaat gtagaaaaaa acaccagccc tcagggagta cacaatgatg tgagcaagtt
1921 caatacacaa aattatgcaa ggacttctgt gatagaaagc cccagtacaa atcggactac
1981 tccagtgagc actccacctt tacttacatc aagcaaagca gggtctccca tcaatctctc
2041 tcaacactct ctggtcatca aatggaattc cccaccatat gtctgcagta ctcagtctga
2101 aaagctaaca aatactgcat ctaaccactc aatggacctt acaaaaagca aagacccacc
2161 aggagagaaa ccagcccaaa atgaaggtgc acagaactct gcaacgttta gtgccagtaa
2221 gctgttacaa aatttagcac aatgtggaat gcagtcatcc atgtcagtgg aagagcagag
2281 acccagcaaa cagctgttaa ctggaaacac agataaaccg ataggtatga ttgatagatt
2341 aaatagccct tgctctcaa ataaaacaaa tgcagttgaa gaaaataaag catttagtag
2401 tcaaccaaca ggtcctgaac cagggctttc tggttctgaa atagaaaatc tgcttgaaag
2461 acgtactgtc ctccagttgc tcctggggaa ccccaacaaa gggaagagtg aaaaaaaaga
2521 gaaaactccc ttaagagatg aaagtactca ggaacactca gagagagctt taagtgaaca
2581 aatactgatg gtgaaaataa aatctgagcc ttgtgatgac ttacaaattc ctaacacaaa
2641 tgtgcacttg agccatgatg ctaagagtgc cccattcttg ggtatggctc ctgctgtgca
2701 gagaagcgca cctgccttac cagtgtccga agactttaaa tcggagcctg tttcacctca
2761 ggattttct ttctccaaga atggtctgct aagtcgattg ctaagacaaa atcaagatag
2821 ttacctggca gatgattcag acaggagtca cagaaataat gaaatggcac ttctagaatc
2881 aaagaatctt tgcatggtcc ctaagaaaag gaagctttat actgagccat agaaaatcc
2941 atttaaaaag atgaaaaaca acattgttga tgctgcaaac aatcacagtg ccccagaagt
3001 actgtatggg tccttgctta accaggaaga gctgaaattt agcagaaatg atcttgaatt
3061 taaatatcct gctggtcatg gctcagccag cgaaagtgaa cacaggagtt gggccagaga
3121 gagcaaaagc tttaatgttc tgaaacagct gcttctctca gaaaactgtg tgcgagattt
3181 gtccccgcac agaagtaact ctgtggctga cagtaaaaag aaaggacaca aaaataatgt
```

FIGURE 12A - page 2 of 3

```
3241 gaccaacagc aaacctgaat ttagcatttc ttctttaaat ggactgatgt acagttccac
3301 tcagcccagc agttgcatgg ataacaggac attttcatac ccaggtgtag taaaaactcc
3361 tgtgagtcct actttccctg agcacttggg ctgtgcaggg tctagaccag aatctgggct
3421 tttgaatggg tgttccatgc ccagtgagaa aggacccatt aagtgggtta tcactgatgc
3481 ggagaagaat gagtatgaaa aagactctcc aagattgacc aaaaccaacc caatactata
3541 ttacatgctt caaaaaggag gcaattctgt taccagtcga gaaacacaag acaaggacat
3601 tggagggag gcttcatctg ctgaaagtgt ctcacaggtc acagccaaag aagagttact
3661 tcctactgca gaaacgaaag cttctttctt taatttaaga agcccttaca atagccatat
3721 gggaaataat gcttctcgcc cacacagcgc aaatggagaa gtttatggac ttctgggaag
3781 cgtgctaacg ataagaaag aatcagaata aaatgtacct gccatccagt tttggatctt
3841 tttaaaacta atgagtatga acttgagatc tgtataaata agagcatgat ttgaaaaaaa
3901 gcatggtata attgaaactt ttttcatttt gaaagtatt ggttactggt gatgttgaaa
3961 tatgcatact aattttgct taacattaga tgtcatgagg aaactactga actagcaatt
4021 ggttgtttaa cacttctgta tgcatcagat aacaactgtg agtagcctat gaatgaaatt
4081 cttttataaa tattaggcat aaattaaaat gtaaaactcc attcatagtg gattaatgca
4141 ttttgctgcc tttattaggg tactttattt tgcttttcag aagtcagcct acataacaca
4201 tttttaaagt ctaaactgtt aaacaactct ttaaggata attatccaat aaaaaaaaac
4261 ctagtgctga ttcacagctt attatccaat tcaaaataa attagaaaaa tatatgctta
4321 catttttcac ttttgctaaa aagaaaaaaa aaaggtgttt attttttaact cttggaagag
4381 gttttgtggt tcccaatgtg tctgtcccac cctgatcctt ttcaatatat atttctttaa
4441 accttgtgct acttagtaaa aattgattac aattgaggga agtttgatag atcctttaaa
4501 aaaaaggcag attttccattt tttgtatttt aactacttta ctaaattaat actcctcctt
4561 ttacagaatt agaaagtta acatttatct ttaggtggtt tcctgaaaag ttgaatattt
4621 aagaaattgt ttttaacaga agcaaaatgg cttttctttg gacagttttc accatctctt
4681 gtaaaagtta attctcacca ttcctgtggt acctgcgagt gttatgacca ggattcctta
4741 aacctgaact cagaccactt gcattagaac catctggagc acttgtttta aaatgcagat
4801 tcataggcag catctcagat ctacagaaca agaatctctg ctaagtggac ctggaatctt
4861 ccatctgcat cttaacatgc tctctaggtg tttcttgtgt ttgagaacca tgacttatga
4921 ctttcctcag aacatgagac tgtaaaacaa aaacaaaaaa ctatgtgatg cctctatttt
4981 cccaataca gtcacacatc agctcaaaat ttgcaatatt gtagttcata tattaccgtt
5041 atgtctttgg aaatcgggtt cagaacactt tttatgacaa aaattgggtg gaggggataa
5101 ctttcatatc tggctcaaca tctcaggaaa atctgtgatt atttgtgtgt tctaatgagt
5161 aacatctact tagttagcct tagggatgga aaaacagggc cacttaccaa actcaggtga
5221 ttccaggatg gtttggaaac ttctcctgaa tgcatcctta acctttatta aaaccattgt
5281 cctaagaaca atgccaacaa agcttacaac atttagttta aacccaagaa gggcactaaa
5341 ctcagattga ctaaataaaa agtacaaagg gcacatatac gtgacagaat tgtacacaat
5401 cactccattg gatcttttac tttaaagtag tgatgaaaag tacatgttga tactgtctta
5461 gaagaaatta atatattagt gaagccacat ggggtttcag ttgcgaaaca ggtctgtttt
5521 tatgttcagt ttgtacaatc cacaattcat tcaccagata ttttgttctt aattgtgaac
5581 caggttagca aatgacctat caaaaattat tctataatca ctactagtta ggatattgat
5641 ttaaaattgt tctacttgaa gtggtttcta agatttttat attaaaaata ggtgtgattt
5701 cctaatatga tctaaaaccc taaatggtta ttttccctca gaatgatttg taaatagcta
5761 ctggaaatat tatacagtaa taggagtggg tattatgcaa catcatggag aagtgaaggc
5821 ataggcttat tctgacataa aattccactg gccagttgaa tatattctat tccatgtcca
5881 tactatgaca atcttattgt caacactata taataagct tttaaacaag tcatttttct
5941 tgatcgttgt ggaaggtttg gagccttaga ggtatgtcag aaaaaatatg ttggtattct
6001 cccttgggta ggggaaatg acctttttac aagagagtga aatttaggtc agggaaaaga
6061 ccaagggcca gcattgctac ttttgtgtgt gtgtgtgtgg gttttgtttt gtttttttgg
6121 ttggctggtt gttttcgttg ttgttaacaa aggaatgaga atatgtaata cttaaataaa
6181 catgaccacg aagaatgctg ttctgattta ctagagaatg tcccaatttt gaatttaggg
6241 tgattttaaa gaacagtgag aaagggcata catccacaga ttcactttgt ttatgcatat
6301 gtagatacaa ggatgcacat atacacattt tcaaggacta ttttagatat ctagacaatt
6361 tcttctaata aagtcatttg tgaagggta ctacagctta ttgacatcag taaggtagca
6421 ttcattacct gtttattctc tgctgcatct tacagaagag taaactggtg agagtatata
```

FIGURE 12A - page 3 of 3

```
6481 ttttatatat atatatatat atatatatat aatatgtata tatatatata ttgacttgtt
6541 acatgaagat gttaaaatcg gttttttaaag gtgatgtaaa tagtgatttc cttaatgaaa
6601 aatacatatt ttgtattgtt ctaatgcaac agaaaagcct tttaatctct ttggttcctg
6661 tatattccat gtataagtgt aaatataatc agacaggttt aaaagttgtg catgtatgta
6721 tacagttgca agtctggaca aatgtataga ataaaccttt tatttaagtt gtgattacct
6781 gctgcatgaa aagtgcatgg gggaccctgt gcatctgtgc atttggcaaa atgtcttaac
6841 aaatcagatc agatgttcat cctaacatga cagtattcca tttctggaca tgacgtctgt
6901 ggtttaagct ttgtgaaaga atgtgctttg attcgaaggg tcttaaagaa ttttttttaat
6961 cgtcaaccac ttttaaacat aaagaattca cacaactact ttcatgaatt ttttaatccc
7021 attgcaaaca ttattccaag agtatcccag tattagcaat actggaatat aggcacatta
7081 ccattcatag taagaattct ggtgtttaca caaccaaatt tgatgcgatc tgctcagtaa
7141 tataatttgc cattttttatt agaaatttaa ttcttcatg tgatgtcatg aaactgtaca
7201 tactgcagtg tgaatttttt tgttttgttt tttaatcttt tagtgtttac ttcctgcagt
7261 gaatttgaat aaatgagaaa aaatgcattg tc
```

FIGURE 12B

```
   1 mthgeelgsd vhqdsivlty legllmhqaa ggsgtavdkk saghneedqn fnisgsafpt
  61 cqsngpvlnt htyqgsgmlh lkkarllqss edwnaakrkr lsdsimnlnv kkeallagmv
 121 dsvpkgkqds tllasllqsf ssrlqtvals qqirqslkeq gyalshdslk vekdlrcygv
 181 asshlktllk kskvkdqkpd tnlpdvtknl irdrfaesph hvgqsgtkvm seplscaarl
 241 qavasmvekr aspatspkps vacsqlalll sseahlqqys rehalktqna nqaaserlaa
 301 marlqengqk dvgsyqlpkg msshlngqar tsssklmask ssatvfqnpm giipsspkna
 361 gyknslernn ikqaannsll lhllksqtip kpmnghshse rgsifeesst pttideysdn
 421 npsftddssg dessysncvp idlsckhrte ksesdqpvsl dnftqsllnt wdpkvpdvdi
 481 kedqdtskns klnshqkvtl lqlllghkne envekntspq gvhndvskfn tqnyartsvi
 541 espstnrttp vstpplltss kagspinlsq hslvikwnsp pyvcstqsek ltntasnhsm
 601 dltkskdppg ekpaqnegaq nsatfsaskl lqnlaqcgmq ssmsveeqrp skqlltgntd
 661 kpigmidrln spllsnktna veenkafssq ptgpepglsg seienllerr tvlqlllgnp
 721 nkgksekkek tplrdestqe hseralseqi lmvkiksepc ddlqipntnv hlshdaksap
 781 flgmapavqr sapalpvsed fksepvspqd fsfsknglls rllrqnqdsy laddsdrshr
 841 nnemallesk nlcmvpkkrk lyteplenpf kkmknnivda annhsapevl ygsllnqeel
 901 kfsrndlefk ypaghgsase sehrswares ksfnvlkqll lsencvrdls phrsnsvads
 961 kkkghknnvt nskpefsiss lnglmyssstq psscmdnrtf sypgvvktpv sptfpehlgc
1021 agsrpesgll ngcsmpsekg pikwvitdae kneyekdspr ltktnpilyy mlqkggnsvt
1081 sretqdkdiw reassaesvs qvtakeellp taetkasffn lrspynshmg nnasrphsan
1141 gevygllgsv ltikkese
```

FIGURE 13A – page 1 of 2

```
   1 gagacattgc agcagagccc cgaactcggg aggcgacggc gaccgcggcg caggcggagg
  61 acgagccggc cccagcccgc ccgagcgcag cgcccgtggc ctcgcgcggc cgcagggcac
 121 ggctaacctg ggaaggaggg agcgacgcgg atcggcggcc cggagccgcg gcggcctcga
 181 aggcgtggac tgtgagcggt tgcagagctg ttctcaggac ataatccttt aacattcggg
 241 aggaacacat ccaggaggtg cgcagttgac tgaggaggcc cggagaatct gaagactccg
 301 atgacatcag agttgctttt caacagcctt ctcagcttcc tttcccacat agcagaggct
 361 caggctgagg cagacgatac tgacgtgcgt ttggtgagca acgaaagatg atgaagaaag
 421 aaaaccagca tattccctga gacctgggtg ccagcgctgc cgctgtgcta aggaagttgc
 481 gaggctggcc cttgcctagc cactcatcag tgctgtagtc tgcacccgag tttgccccag
 541 cctctgagcc cctcgtcact gcctgaagat ccctggtca gaatgttaac agtgcatctc
 601 tgcccgactg ctatgggagg tgatcaggtg acgctcactt cctgacgtca cgtgggatct
 661 tactgacgag aggagctctt tcacgtgaac ggaagccgag ccctgtgag cgcttgtatt
 721 gaacatgact catggagaag agcttggctc tgatgtgcat caggattcta ttgtcttaac
 781 ttacctcgaa gggttactaa tgcatcaggc agcaggggga tcaggcactg ccattaacaa
 841 aaagtctgct ggccacaaag aggaagacca gaactttaac ctctcgggca gtgcgtttcc
 901 ctcctgtcaa agcaatggtc ccactgtcag tacccagacg taccagggat ctggcatgct
 961 gcacctcaaa aaagccagac tgctgcagtc ttccgaggac tggaacgcgg caaagcggaa
1021 gaggctgtct gattccatcg tgaatttaaa cgtaaagaag gaagcgttgc tggctggcat
1081 ggttgacagt gtgcctaaag gcaaacagga tagcacattg ctggcctctt tgcttcagtc
1141 attcagctct aggctgcaga ctgttgctct gtcacagcag attagacaga gcctcaagga
1201 gcagggatat gccctcagtc acgagtcttt aaaagtggag aaggatttaa ggtgctatgg
1261 cgtggcctca agtcacttaa aaactctgtt gaagaaaagt aaaaccaagg atcaaaagtc
1321 aggtcccacc ctccctgacg tgactccaaa ccttatcaga gatagctttg ttgagtcatc
1381 ccatcccgca gtgggacaaa gtgggacaaa ggtcatgagt gagcccttgt catgtgctgc
1441 aagattacag gctgttgcca gcatggtgga gaaagggcg agtcccgctg cctccccaaa
1501 gcctagtgtt gcctgcagcc agttggcgct gctcctgtcc agcgaggccc acctgcagca
1561 gtactctcgg gaacatgctc taaaaacgca gaacgcacat caggtggcaa gcgaaagact
1621 tgcagccatg gccagattgc aagagaatgg gcagaaggac gtgggcagtt cgcagctctc
1681 caaaggggtg tctggccatc tcaacgggca ggccagagca ctgccggcaa gcaaactggt
1741 ggccaacaag aataacgctg ccacctttca gagtccaatg ggtgttgtcc cttcctcccc
1801 caaaaacacg agctataaga actcactgga aagaaacaac ctaaagcagg ctgctaataa
1861 cagtctgctt ttgcatctct tcaaaagcca gaccatacccc acgccgatga acggcacag
1921 ccagaacgag agagcgagca gttttgagag tagcacgccc accacgattg atgagtactc
1981 cgataacaac ccgagcttta cagatgacag cagtggagac gaaagctcgt actccaattg
2041 cgttcccata gacctgtctt gcaaacaccg gatcgaaaag ccggaagctg agcggcccgt
2101 ttcgctggag aacctaaccc agtccttgtt aaacacgtgg gatcccaaga tccccggcgt
2161 tgacatcaaa gaagatcaag atacctcaac aaattccaag ctgaattcac accagaaagt
2221 cactcttctt cagttgctgc tcggccataa aagtgaagaa actgttgaaa ggaacgccag
2281 ccctcaggac atccatagtg atgggactaa gttcagtcct cagaattaca caaggacttc
2341 tgtcatcgaa agccccagta ccaacaggac taccccagtg agcactccac cactgtatac
2401 agccagccaa gcagagtctc ccatcaatct ttcccagcac tctctggtca tcaagtggaa
2461 ttccccgccg tatgcctgca gtactcccgc ttccaagctc acgaacaccg cgcctagcca
2521 cctgatggac ctcacgaaag gcaaagagtc ccaagccgag aaaccagccc cgagtgaagg
2581 tgcacaaaat tccgccacgt tcagtgccag taaactgtta caaaatttgg ctcagtgcgg
2641 attgcagtct tccgggccag gggaagagca gagaccctgc aaacagctgt taagtggaaa
2701 cccagacaaa cctctcggtc tgattgatag attaaacagc cctctgctct caaataaaac
2761 caatgcggct gaagagagca agccttcag cagtcagcct gcgggcctg agccgggact
2821 tcctggttgt gagatagaaa atctcttgga aagacggact gtccttcagt tgctcctggg
2881 aaattccagc aaagggaaga tgagaagaa agagaaaacc cccgcacgag acgaggctcc
2941 tcaggagcat tcggagaggg ctgcaaatga acagatactc atggtgaaga ttaaatccga
3001 gccttgtgac gacttccaga cccacaacac aaacctgccc ttaaaccacg atgccaagag
3061 cgccccttc ttaggtgtga ctcccgccat ccacaggagc acagcggcct taccagtgtc
3121 ggaggacttt aaatccgagc ctgcttcacc tcaggattc tctttctcaa agaacgggct
```

FIGURE 13A - page 2 of 2

```
3181 gttgagtcgc ttgctgagac agaatcaaga gagttacccg gcagatgagc aggacaagag
3241 tcacagaaac agtgagctgc caaccctgga gtcgaagaac atctgcatgg tcccgaagaa
3301 aaggaagctg tatacgaac cactggagaa tccatttaaa aagatgaaaa atactgccgt
3361 agatactgcc aatcatcaca gcggcccgga agtactctac gggtcgttgc ttcatcagga
3421 agagctgaag tttagcagga atgagctcga ttataaatac cctgctgggc atagttcagc
3481 cagcgatggt gaccacagga gttgggccag agagagcaaa agcttcaatg ttctcaagca
3541 gctgctgctc tccgagaact gtgtgcgaga tctgtcccca cacaggagtg actctgtccc
3601 cgacacgaaa aagaaaggac acaaaaacaa cgcgcccggc agcaaacctg aattcggcat
3661 ttcttcttta aatggactga tgtatagttc cccgcagcct ggcagttgtg tgacggatca
3721 taggacattt tcatacccgg aatggtaaa gaccctctg agccctcctt tcccagagca
3781 cttgggctgt gtggggtcca gaccagaacc tgggcttttg aatggatgtt ccgtgcccgg
3841 tgagaaggga cccattaagt gggtcatcgc agatatggat aagaatgaat acgaaaaga
3901 ctctccaaga ctgaccaaaa ctaatccgat cctctattac atgctccaga agggaggggg
3961 caattctgtt accacacaag aaacccagga caaagacatc tggagggagc ctgcgtcagc
4021 cgagagtctc tcacaggtta cagtcaaaga agagctactt cccgctgcag aaactaaagc
4081 ttctttcttt aatctaagaa gcccgtacaa tagccatatg ggaaataatg cttctcgccc
4141 acacagtaca aatggagaag tgtatggact tctgggaaac gcgctcacca taaaaaaga
4201 gtcagaataa atgtgtacct gccataccac tttgggtctt tttaaaattt agtcagtatg
4261 aacttgagat ctgtataaat aagagcatga tttgagaaaa gcatggtata actgaaactc
4321 cttccttttg aaagtattgg tcactggtga tgtttaaata tgcatactaa tttttgctta
4381 acattagatg tcatgaggaa acaattgaac tcgaggttgg ttgtttacta tttctgtatg
4441 catcagataa caactgtgac tagcctacga atgaacctgt ttttataatc gtaaataaga
4501 ggcatacatt aaaatgcaca acttcaccag g
```

FIGURE 13B

```
   1 mthgeelgsd vhqdsivlty legllmhqaa ggsgtainkk saghkeedqn fnlsgsafps
  61 cqsngptvst qtyqgsgmlh lkkarllqss edwnaakrkr lsdsivnlnv kkeallagmv
 121 dsvpkgkqds tllasllqsf ssrlqtvals qqirqslkeq gyalsheslk vekdlrcygv
 181 asshlktllk ksktkdqksg ptlpdvtpnl irdsfvessh pavgqsgtkv mseplscaar
 241 lqavasmvek raspaaspkp svacsqlall lsseahlqqy srehalktqn ahqvaserla
 301 amarlqengq kdvgssqlsk gvsghlngqa ralpasklva nknnaatfqs pmgvvpsspk
 361 ntsyknsler nnlkqaanns lllhllksqt iptpmnghsq nerassfess tpttideysd
 421 nnpsftddss gdessysncv pidlsckhri ekpeaerpvs lenltqslln twdpkipgvd
 481 ikedqdtstn sklnshqkvt llqllghks eetvernasp qdihsdgtkf spqnytrtsv
 541 iespstnrtt pvstpplyta sqaespinls qhslvikwns ppyacstpas kltntapshl
 601 mdltkgkesq aekpapsega qnsatfsask llqnlaqcgl qssgpgeeqr pckqllsgnp
 661 dkplglidrl nspllsnktn aaeeskafss qpagpepglp gceienller rtvlqlllgn
 721 sskgknekke ktpardeapq ehseraaneq ilmvkiksep cddfqthntn lplnhdaksa
 781 pflgvtpaih rstaalpvse dfksepaspq dfsfskngll srllrqnqes ypadeqdksh
 841 rnselptles knicmvpkkr klyteplenp fkkmkntavd tanhhsgpev lygsllhqee
 901 lkfsrneldy kypaghssas dgdhrsware sksfnvlkql llsencvrdl sphrsdsvpd
 961 tkkkghknna pgskpefgis slnglmyssp qpgscvtdhr tfsypgmvkt plsppfpehl
1021 gcvgsrpepg llngcsvpge kgpikwviad mdkneyekds prltktnpil yymlqkgggn
1081 svttqetqdk diwrepasae slsqvtvkee llpaaetkas ffnlrspyns hmgnnasrph
1141 stngevygll gnaltikkes e
```

RIP140 REGULATION OF GLUCOSE TRANSPORT

CROSS-REFERENCE TO RELATED APPLICATIONS

This application is a continuation of U.S. patent application No. 12/575,981, filed on Oct. 8, 2009 (issued as U.S. Pat. No. 8,093,223 on Jan. 10, 2012), which claims the benefit of priority of U.S. patent application Serial No. 11/075,646, filed on Mar. 7, 2005 (issued as U.S. Pat. No. 7,691,823 on Apr. 6, 2012), and U.S. Provisional Patent Application Ser. No. 60/550,677, filed on Mar. 5, 2004. These prior applications are herein incorporated by reference in their entirety.

STATEMENT OF FEDERALLY SPONSORED RESEARCH

The invention was made with government support under grant no. DK030648 awarded by the National Institutes of Health. The government has certain rights in thisF invention.

TECHNICAL FIELD

This invention relates to molecular biology, cell biology, cellular metabolism, and diabetes.

BACKGROUND

Insulin stimulates glucose transport in muscle and fat. One of the most critical pathways that insulin activates is the rapid uptake of glucose from the circulation in both muscle and adipose tissue. Most of insulin's effect on glucose uptake in these tissues is dependent on the insulin-sensitive glucose transporter, GLUT4 (reviewed in Czech and Corvera, *J. Biol. Chem.*, 274:1865-1868, 1999; Martin et al., *Cell Biochem. Biophys.*, 30:89-113, 1999; Elmendorf et al., *Exp. Cell Res.*, 253:55-62, 1999). The mechanism of insulin action is impaired in diabetes, leading to less glucose transport into muscle and fat. This is thought to be a primary defect in type II diabetes. Potentiating insulin action has a beneficial effect on type II diabetes. This is believed to be the mechanism of action of the drug Rezulin (troglitazone).

Type II diabetes mellitus (non-insulin-dependent diabetes) is a group of disorders characterized by hyperglycemia that can involve an impaired insulin secretory response to glucose and insulin resistance. One effect observed in type II diabetes is a decreased effectiveness of insulin in stimulating glucose uptake by skeletal muscle. Type II diabetes accounts for about 85-90% of all diabetes cases.

RIP140 (receptor interacting protein 140, also known as NRIP1, for Nuclear Receptor-interacting Protein 1) is a corepressor that can inhibit the transcriptional activity of a number of nuclear receptors.

SUMMARY

The present invention relates to findings regarding the role of RIP140 in glucose transport.

Accordingly, the invention relates to methods of increasing glucose transport in a cell by inhibiting RIP140 expression or activity. In some cases, RIP140 expression is inhibited by a mechanism that involves RNA inhibition (RNAi), e.g., an siRNA or other mechanism related to the use of a nucleic acid (e.g., an antisense nucleic acid that is targeted to RIP140).

Accordingly, in one aspect, the invention features a method for increasing glucose transport in a cell by providing a cell and contacting the cell with an agent that inhibits expression or activity of a RIP140 polypeptide, thereby increasing glucose transport in the cell. Also featured is a method for decreasing glucose transport by providing a cell and contacting the cell with an agent that increases expression or activity of a RIP140 polypeptide, thereby increasing glucose transport in the cell.

The agent can include a polynucleotide, a polypeptide, a small non-nucleic acid organic molecule, a small inorganic molecule, or an antibody, e.g., a small inhibitory RNA (siRNA) (e.g., including a sequence selected from SEQ ID NO:1, SEQ ID NO:2, SEQ ID NO:3, and SEQ ID NO:4) an antisense oligonucleotide, an inhibitory RNA, or a ribozyme. The cell is contacted in vitro or in vitro.

In some embodiments, the agent inhibits RIP140-mediated suppression of expression of a gene. In some embodiments, the agent decreases binding of RIP140 polypeptide to a second polypeptide. In some embodiments, the second polypeptide is a Peroxisome Proliferator-Activated Receptor (PPAR), e.g., PPAR alpha, PPAR delta, or PPAR gamma.

Also provided herein is a method for increasing insulin-stimulated glucose uptake in a subject (e.g., a human) that is at risk for or suffering from a disorder related to glucose metabolism (e.g., diabetes or obesity), by administering to the subject an agent that decreases expression or activity of a RIP140 polypeptide in an amount sufficient to modulate glucose metabolism in a cell of the subject, thereby increasing insulin-stimulated glucose uptake in the subject.

The disorder can be type I diabetes, type II diabetes. In some embodiments, the agent is an siRNA (e.g., an siRNA comprising SEQ ID NO:1, SEQ ID NO:2, SEQ ID NO:3, or SEQ ID NO:4)

Also provided herein is a method for identifying a candidate agent that modulates expression or activity of a RIP140 polypeptide. The method includes (a) providing a sample comprising a RIP140 polypeptide or a nucleic acid encoding the polypeptide; (b) contacting the sample with a test compound under conditions in which the polypeptide is active, the nucleic acid is expressed, or both; (c) evaluating expression or activity of the RIP140 polypeptide in the sample; and (d) comparing the expression or activity of the RIP140 polypeptide of (c) to expression or activity of the RIP140 polypeptide in a control sample lacking the test compound, wherein a change in RIP140 polypeptide expression or activity indicates that the test compound is a candidate agent that can modulate the expression or activity of the RIP140 polypeptide.

The sample can include a cell, e.g., an adipocyte. In other embodiments, the sample is a cell-free sample. In various embodiments, the evaluating includes performing a cell-free assay.

The evaluating can include determining whether glucose transport is modulated in the presence of the test compound, e.g., by determining glucose uptake.

The test compound can include a polynucleotide, a polypeptide, a small non-nucleic acid organic molecule, a small inorganic molecule, or an antibody, e.g., an antisense oligonucleotide, an inhibitory RNA, or a ribozyme.

In some embodiments, modulation of glucose transport is evaluated using an antibody. Glucose transport can be increased or decreased in the presence of the test compound.

In some embodiments, an activity of RIP140 is evaluated, e.g., by determining the level of interaction of RIP140 with a second polypeptide, e.g., a PPAR, e.g., PPARalpha, PPAR-delta, or PPARgamma.

The method can further include testing the candidate agent in an animal model, e.g., an animal model of obesity or diabetes, e.g, by evaluating RIP140 RNA levels, and/or by evaluating one or more of insulin levels or glucose levels. The method can further include, e.g., optimizing the agent and formulating the agent for pharmaceutical use.

In some embodiments, RIP140-mediated modulation of gene expression is evaluated, e.g. RIP140-mediated suppression of gene expression, or RIP140-mediated enhancement of gene expression. A change in RIP140 activity can be evaluated by determining a change in the level of expression of a second gene, relative to a control.

Also provided herein is a method of increasing the amount of brown fat in a subject by administering an amount of a RIP140 inhibitor sufficient to decrease the level of expression or activity of RIP140 in a white fat cell to the subject. Increasing brown fat can increase the level of metabolism in the subject and thereby decrease obesity.

Also provided herein is method for identifying a candidate agent that modulates expression or activity of a polypeptide selected from the group consisting of C/EBP beta, C/EBP zeta, GA repeat binding protein alpha, LXR beta, EAR2, Nur77, nuclear receptor binding factor 1, nuclear receptor interacting protein 3, PPAR alpha, PPAR binding protein, PPAR gamma, and coactivator 1 beta, the method including (a) providing a sample comprising the polypeptide or a nucleic acid encoding the polypeptide; (b) contacting the sample with a test compound under conditions in which the polypeptide is active, the nucleic acid is expressed, or both; (c) evaluating expression or activity of the polypeptide in the sample; and (d) comparing the expression or activity of the polypeptide of (c) to expression or activity of the polypeptide in a control sample lacking the test compound, wherein a change in polypeptide expression or activity indicates that the test compound is a candidate agent that can modulate the expression or activity of the polypeptide.

Also provided herein is a method for identifying a candidate agent that modulates expression or activity of a polypeptide selected from group consisting of C/EBP delta, C/EBP gamma, Rev-ErbA alpha, LXR alpha, COUP/TFII beta, progesterone receptor membrane component 1, progesterone receptor membrane component 2, and retinoid receptor beta, by (a) providing a sample comprising the polypeptide or a nucleic acid encoding the polypeptide; (b) contacting the sample with a test compound under conditions in which the polypeptide is active, the nucleic acid is expressed, or both; (c) evaluating expression or activity of the polypeptide in the sample; and (d) comparing the expression or activity of the polypeptide of (c) to expression or activity of the polypeptide in a control sample lacking the test compound, wherein a change in polypeptide expression or activity indicates that the test compound is a candidate agent that can modulate the expression or activity of the polypeptide.

In general, the methods in which cellular functions are assayed, the cell used in the assay can conduct glucose transport (e.g., is an adipose cell, a muscle cell, or a liver cell). Thus, in certain methods, a compound that can bind RIP140 is assayed in a cell that can conduct glucose transport (and optionally, is insulin sensitive), contacting a the cell with a compound that can bind to RIP140, and determining whether the cell increases a cellular function associated with glucose transport or increased fatty acid metabolism.

The invention also features a method of identifying a candidate compound for increasing glucose transport in a cell. The method includes providing a sample comprising a Peroxisome Proliferator-Activated Receptor (PPAR), contacting the sample with a RIP140 and a test compound, determining the level of interaction between the PPAR (PPARalpha, PPARdelta, or PPARgamma) and RIP140, such that a decrease in the level of interaction between the PPAR and RIP140 in the presence of the test compound compared to a control that does not comprise the test compound indicates that the compound is a candidate compound for increasing glucose transport in a cell.

In another embodiment, the invention relates to a method of increasing the amount of brown fat in a subject. The method includes administering an amount of a RIP140 inhibitor sufficient to decrease the level of expression or activity of RIP140 in a white fat cell to the subject. In some embodiments, the RIP inhibitor is an siRNA or other nucleic acid that functions in the RNAi pathway.

By "specifically binds" is meant a molecule that binds to a particular entity, e.g., a RIP140 polypeptide in a sample, but which does not substantially recognize or bind to other molecules in the sample, e.g., a biological sample, which includes the particular entity, e.g., a RIP140 polypeptide.

A "polypeptide" is a chain of amino acids regardless of length or post-translational modifications. Thus, the terms polypeptides, protein, and peptide are used interchangeably. As used herein, the term "RIP140" means a RIP140 polypeptide.

An animal or human, is "at risk for" or "predisposed to" developing a condition such as a glucose transport-related disorder (e.g., type II diabetes) if there is an increased probability that it will develop the condition compared to a population (e.g., the general population, an age-matched population, a population of the same sex). The increased probability can be due to one or a combination of factors including the presence of specific alleles/mutations of a gene or exposure to a particular environment.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, drawings, and from the claims.

DESCRIPTION OF DRAWINGS

FIG. 1 is a list of sequences identified as having significant homology to RIP140.

FIG. 2 is a bar graph illustrating the results of experiments in which cells were transfected with siRNA targeting RIP140, PTEN, Akt, or scrambled and the amount of Akt phosphorylation determined in the presence or absence of insulin.

FIG. 3 is a bar graph illustrating the results of experiments in which cells were transfected with siRNA targeting RIP140, PTEN, or scrambled (control) and deoxyglucose transport assayed in the presence or absence of insulin.

FIG. 5 is a chart indicating the results of experiments detecting the level of expression of the listed expressed sequences in mice characterized by having different features of glucose metabolism.

FIG. 11 is a table listing the Affymetrix probe, GenBank® Accession Number, gene name, gene symbol, and fold change in genes in response to RIP140 depletion, as measured by Affymetrix gene chip analysis. Affymetrix gene chip analysis was performed on day 8 3T3-L1 adipocytes electroporated with scrambled siRNA or RIP140 siRNA. Fold change indicates the difference in expression between scrambled- and RIP140 siRNA-transfected cells. Increased expression of transcription factors, including PGC-1β, ERRα, and Gabpa, may explain the changes in cellular metabolism seen with RIP140 depletion.

FIG. 12 A is a representation of a human RIP140 nucleotide sequence (SEQ ID NO: 5).

FIG. 12B is a representation of a human RIP140 amino acid sequence (SEQ ID NO: 6).

FIG. 13A. is a representation of a murine RIP140 nucleotide sequence (SEQ ID NO: 7).

FIG. 13B is a representation of a murine RIP140 amino acid sequence (SEQ ID NO: 8).

DETAILED DESCRIPTION

Figure 4:
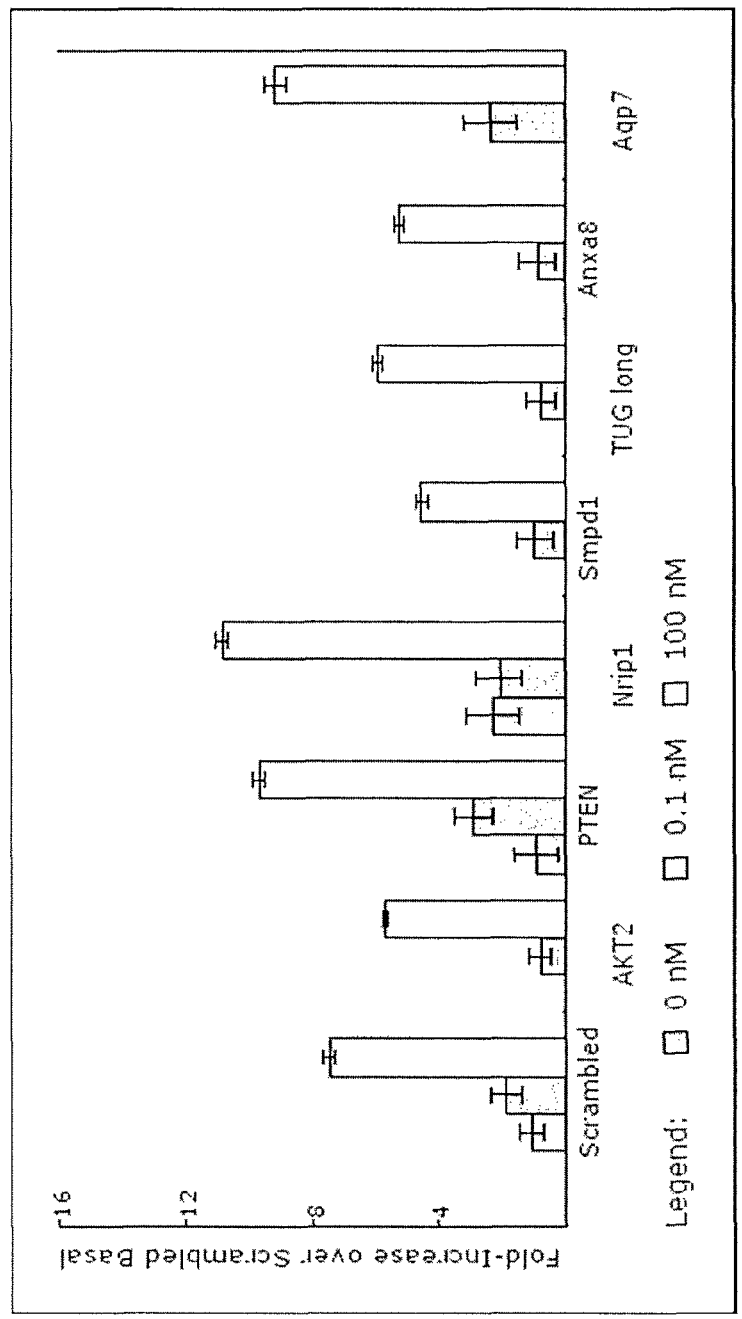
FIG. 4 is a bar graph illustrating the results of experiments in which cells were transfected with siRNA targeting Akt2, PTEN, Nrip1, Smpd1, TUG long, Anxa8, or scrambled (control) and deoxyglucose transport assayed in the presence or absence of insulin.

It has been found that RIP140 plays a role in glucose transport and the decreasing the level of RIP140 expression increases glucose transport. Thus, compounds that decrease RIP140 expression or activity are useful for increasing glucose transport and can be used as therapeutics for treating disorders in which it is desirable to increase glucose transport, for example, in diabetes. Decreasing RIP140 expression or activity is also useful for increasing the amount of brown fat, thereby increasing metabolism and thus promoting weight loss. Compounds that can decrease RIP expression or activity are useful for treating conditions or disorders associated with an undesirable amount of white fat, e.g., obesity or obesity associate with type II diabetes. Furthermore, RIP140 interacts with several different PPARs. Compounds that decrease the interaction between RIP140 and a ligand such as a PPAR (Peroxisome Proliferator-Activated Receptor; e.g., PPARalpha, PPARdelta, and PPARgamma) are useful for treating disorders associated with RIP140 activity, e.g., diabetes or obesity. Furthermore, compounds that inhibit RIP140 expression or activity not only are useful for increasing glucose uptake in a cell, but are also useful for increasing insulin sensitivity of a cell, and are generally useful for activating transcription through PPARs and enhancing energy expenditure and cellular metabolism.

RIP140 and PPAR

RIP140 is a nuclear protein containing approximately 1158 amino acids, with a size of approximately 128 kDa. RIP140 binds to nuclear receptors via LXXLL motifs, wherein L is leucine and X is any amino acid (Heery et al., Nature, 387 (6634):733-6, 1997). Ten LXXLL motifs are found in the RIP140 sequence. RIP140 also interacts with histone deacetylases and with C-terminal binding protein (CTBP) via a PXDLS motif found in the RIP140 sequence.

A human RIP140 nucleotide sequence is listed in GenBank® under Accession No. NM_003489. The corresponding human amino acid sequence is found under Accession No. NP_003480. The nucleotide sequence of the chromosomal region containing the entire human RIP140 gene can be found in GenBank® under Accession No. AF248484. A murine RIP140 nucleotide sequence can be found in GenBank® under Accession No. NM_173440. The corresponding murine amino acid sequence is found under Accession No. NP 775616. RIP140 is highly conserved between vertebrate species.

A number of RIP140 homologs are known in the art. A partial list of such sequences is provided in FIG. 1 Inhibition of expression of a RIP140 in a cell that normally conducts glucose transport in response to stimulation by insulin (e.g., a fat cell) results in increased glucose transport. A biologically active RIP140 or fragment thereof includes sequences that can be transfected into a RIP140−/− cell and restore RIP140 activity.

In some embodiments, RIP140 activity can be determined by examining levels of RIP140 binding to PPARs. PPAR sequences are known in the art, for example see Genbank® accession nos. NP005027 (PPARalpha), Q03181 (PPARdelta), P37231 (PPARgamma).

Screening Assays

The methods described herein include methods (also referred to herein as "screening assays") for identifying modulators, i.e., test compounds or agents, of RIP140 expression or RIP140 activity. Such test compounds include, e.g., polypeptides, peptides, peptidomimetics, peptoids, small inorganic molecules, small non-nucleic acid organic molecules, nucleic acids (e.g., anti-sense nucleic acids, siRNA, oligonucleotides, synthetic oligonucleotides), carbohydrates, or other agents that bind to RIP140 proteins, have a stimulatory or inhibitory effect on, for example, RIP140 expression or RIP140 activity, or have a stimulatory or inhibitory effect on, for example, the expression or activity of a RIP140 substrate. Compounds thus identified can be used to modulate the activity of target gene products (e.g., RIP140 genes) in a therapeutic protocol, to elaborate the biological function of a RIP140, or to identify compounds that disrupt RIP140 interactions (e.g., with a PPAR such as PPARalpha, PPARdelta, or PPARgamma).

In general, screening assays involve assaying the effect of a test agent on expression or activity of a RIP140 nucleic acid or polypeptide in a test sample (i.e., a sample containing the RIP140 nucleic acid or polypeptide). Expression or activity in the presence of the test compound or agent is compared to expression or activity in a control sample (i.e., a sample containing a RIP140 polypeptide that was incubated under the same conditions, but without the test compound). A change in the expression or activity of the RIP140 nucleic acid or polypeptide in the test sample compared to the control indicates that the test agent or compound modulates expression or activity of the RIP140 nucleic acid or polypeptide and is a candidate agent.

Compounds can be tested for their ability to modulate one or more RIP140 mediated activities. For example, compounds that inhibit RIP140 activity result in at least one of increased insulin sensitivity, increased glucose transport, increased energy expenditure, increased metabolism, or increased fatty acid oxidation. Methods of assaying a compound for such activities are known in the art. In some cases, a compound is tested for it's ability to directly affect RIP140 expression or binding to a RIP140 ligand (e.g., by decreasing the amount of RIP140 RNA in a cell, decreasing the amount of RIP140 protein in a cell, or decreasing the repressor-associated binding of RIP140) and tested for its ability to modulate a metabolic effect associated with RIP140 (e.g., increased insulin sensitivity, increased glucose transport, increased energy expenditure, increased metabolism, or increased fatty acid oxidation).

In one embodiment, assays are provided for screening candidate or test molecules that are substrates of a RIP140 polypeptide or a biologically active portion thereof in a cell that is insulin sensitive (e.g., a cell that can increase glucose transport in response to insulin). In another embodiment, the assays are for screening candidate or test compounds that bind to a RIP140 or modulate the activity of a RIP140 or a biologically active portion thereof. Such compounds include those that disrupt the interaction between RIP140 and a PPAR (e.g., PPARalpha, PPARdelta, or PPARgamma).

The test compounds used in the methods can be obtained using any of the numerous approaches in the art including combinatorial library methods, including: biological libraries; peptoid libraries (libraries of molecules having the functionalities of peptides, but with a novel, non-peptide backbone which are resistant to enzymatic degradation but which nevertheless remain bioactive; e.g., Zuckermann et al., *J. Med. Chem.*, 37:2678-2685, 1994); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, *Anticancer Drug Des.*, 12:145, 1997).

Examples of methods for the synthesis of molecular libraries can be found in the literature, for example in: DeWitt et al., *Proc. Natl. Acad. Sci. USA*, 90:6909, 1993; Erb et al., *Proc. Natl. Acad. Sci. USA*, 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.*, 33:2061, 1994; and Gallop et al., *J. Med. Chem.*, 37:1233, 1994.

Libraries of compounds may be presented in solution (e.g., Houghten, *Bio/Techniques*, 13:412-421, 1992), or on beads (Lam, *Nature*, 354:82-84, 1991), chips (Fodor, *Nature* 364:555-556, 1993), bacteria (U.S. Pat. No. 5,223,409), spores (U.S. Pat. Nos. 5,571,698; 5,403,484; and 5,223,409), plasmids (Cull et al., *Proc. Natl. Acad. Sci. USA*, 89:1865-1869, 1992) or phage (Scott and Smith, *Science*, 249:386-390, 1990; Devlin, *Science*, 249:404-406, 1990; Cwirla et al., *Proc. Natl. Acad. Sci. USA*, 87:6378-6382, 1990; and Felici, *J. Mol. Biol.*, 222:301-310, 1991).

In one embodiment, a cell-based assay is employed in which a cell that expresses a RIP140 protein or biologically active portion thereof is contacted with a test compound. The ability of the test compound to modulate RIP140 expression or activity is then determined, e.g., by monitoring, glucose transport, insulin sensitivity, increased energy expenditure, increased metabolism, or increased fatty acid oxidation. The cell, for example, can be a yeast cell or a cell of mammalian origin, e.g., rat, mouse, or human.

The ability of the test compound to modulate RIP140 binding to a compound, e.g., a RIP140 substrate, or to bind to RIP140 can also be evaluated. This can be accomplished, for example, by coupling the compound, e.g., the substrate, with a radioisotope or enzymatic label such that binding of the compound, e.g., the substrate, to RIP140 can be determined by detecting the labeled compound, e.g., substrate, in a complex. Alternatively, RIP140 can be coupled with a radioisotope or enzymatic label to monitor the ability of a test compound to modulate RIP140 binding to a RIP140 substrate in a complex. For example, compounds (e.g., RIP140 substrates) can be labeled with $^{125}$I, $^{35}$S, $^{14}$C, or $^{3}$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a RIP140 substrate) to interact with RIP140 with or without the labeling of any of the interactants can be evaluated. For example, a microphysiometer can be used to detect the interaction of a compound with RIP140 without the labeling of either the compound or the RIP140 (McConnell et al., *Science* 257:1906-1912, 1992). As used herein, a "microphysiometer" (e.g., Cytosensor®) is an analytical instrument that measures the rate at which a cell acidifies its environment using a light-addressable potentiometric sensor (LAPS). Changes in this acidification rate can be used as an indicator of the interaction between a compound and RIP140.

In yet another embodiment, a cell-free assay is provided in which a RIP140 protein or biologically active portion thereof is contacted with a test compound and the ability of the test compound to bind to the RIP140 protein or biologically active portion thereof is evaluated. In general, biologically active portions of the RIP140 proteins to be used in assays described herein include fragments that participate in interactions with non-RIP140 molecules, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected using fluorescence energy transfer (FET) (see, for example, Lakowicz et al., U.S. Pat. No. 5,631,169; Stavrianopoulos et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, the ability of the RIP140 protein to bind to a target molecule (e.g., a PPAR) can be determined using real-time Biomolecular Interaction Analysis (BIA) (e.g., Sjolander et al., *Anal. Chem.*, 63:2338-2345, 1991, and Szabo et al., *Curr. Opin. Struct. Biol.*, 5:699-705, 1995). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In various of these assays, the target gene product (RIP140) or the test substance is anchored onto a solid phase. The target gene product/test compound complexes anchored on the solid phase can be detected at the end of the reaction. Generally, the target gene product is anchored onto a solid surface, and the test compound (which is not anchored) can be labeled, either directly or indirectly, with detectable labels discussed herein.

It may be desirable to immobilize either RIP140, an anti-RIP140 antibody, or its target molecule (e.g., a PPAR such as PPARalpha, PPARdelta, or PPARgamma) to facilitate separation of complexed from uncomplexed forms of one or both of the proteins, as well as to accommodate automation of the assay. Binding of a test compound to a RIP140 protein, or interaction of a RIP140 protein with a target molecule in the presence and absence of a test compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, glutathione-S-transferase/RIP140 fusion proteins or glutathione-S-transferase/target fusion proteins can be adsorbed onto glutathione Sepharose™ beads (Sigma Chemical, St. Louis, Mo.) or glutathione derivatized microtiter plates, which are then combined with the test compound or the test compound and either the non-adsorbed target protein or RIP140 protein. The mixture is then incubated under conditions conducive to complex formation (e.g., at physiological conditions for salt and pH). Following incubation, the beads or microtiter plate wells are washed to remove any unbound components, the matrix immobilized in the case of beads, and the complex determined either directly or indirectly, for example, as described above. Alternatively, the complexes can be dissociated from the matrix, and the level of RIP140 binding or activity determined using standard techniques.

Other techniques for immobilizing either a RIP140 protein or a target molecule on matrices include using conjugation of biotin and streptavidin. Biotinylated RIP140 protein or target molecules can be prepared from biotin-NHS (N-hydroxysuccinimide) using techniques known in the art (e.g., biotinylation kit, Pierce Chemicals, Rockford, Ill.), and immobilized in the wells of streptavidin-coated 96 well plates (Pierce Chemical).

To conduct the assay, the non-immobilized component is added to the coated surface containing the anchored component. After the reaction is complete, unreacted components are removed (e.g., by washing) under conditions such that any complexes formed will remain immobilized on the solid surface. The complexes anchored on the solid surface can be detected in a number of ways. Where the previously non-immobilized component is pre-labeled, the presence of a label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In some cases, the assay is performed utilizing antibodies reactive with RIP140 protein or target molecules, but which do not interfere with binding of the RIP140 protein to its target molecule (e.g., a PPAR). Such antibodies can be derivatized to the wells of the plate, and unbound target or RIP140 protein trapped in the wells by antibody conjugation. Methods for detecting such complexes, in addition to those described above for the GST-immobilized complexes, include immunodetection of complexes using antibodies reactive with the RIP140 protein or target molecule, as well as enzyme-linked assays which rely on detecting an enzymatic activity associated with the RIP140 protein or target molecule.

Alternatively, cell-free assays can be conducted in a liquid phase. In such an assay, the reaction products are separated from unreacted components, by any of a number of standard techniques, including but not limited to: differential centrifugation (see, for example, Rivas and Minton, *Trends Biochem. Sci.*, 18:284-7, 1993); chromatography (gel filtration chromatography, ion-exchange chromatography); electrophoresis (e.g., Ausubel et al., eds. *Current Protocols in Molecular Biology* 1999, J. Wiley: New York.); and immunoprecipitation (see, for example, Ausubel et al., eds., 1999, *Current Protocols in Molecular Biology*, J. Wiley: New York). Such resins and chromatographic techniques are known to one skilled in the art (e.g., Heegaard, *J. Mol. Recognit.*, 11:141-148, 1998; Hage et al., *J. Chromatogr. B. Biomed. Sci. Appl.*, 699:499-525, 1997). Further, fluorescence energy transfer may also be conveniently utilized, as described herein, to detect binding without further purification of the complex from solution.

The assay can include contacting the RIP140 protein or a biologically active portion thereof with a known compound that binds to RIP140 to form an assay mixture, contacting the assay mixture with a test compound, and determining the ability of the test compound to interact with a RIP140 protein, wherein determining the ability of the test compound to interact with a RIP140 protein includes determining the ability of the test compound to preferentially bind to RIP140 or biologically active portion thereof, or to modulate the activity of a target molecule, as compared to the known compound.

A RIP140 can, in vivo, interact with one or more cellular or extracellular macromolecules, such as proteins (e.g., a PPAR). For the purposes of this discussion, such cellular and extracellular macromolecules are referred to herein as "binding partners." Compounds that disrupt such interactions are useful for regulating the activity of the target gene product. Such compounds can include, but are not limited, to molecules such as antibodies, peptides, and small molecules. In general, target genes/products for use in identifying agents that disrupt interactions are the RIP140 genes/products identified herein. In alternative embodiments, the invention provides methods for determining the ability of the test compound to modulate the activity of a RIP140 protein through modulation of the activity of a downstream effector of a RIP140 target molecule. For example, the activity of the effector molecule on an appropriate target can be determined, or the binding of the effector to an appropriate target can be determined, as described herein.

To identify compounds that interfere with the interaction between the target gene product (a RIP140) and its binding partner(s), a reaction mixture containing the target gene product and the binding partner is prepared, under conditions and for a time sufficient, to allow the two products to form a complex. To test an inhibitory agent, the reaction mixture is provided in the presence (test sample) and absence (control sample) of the test compound. The test compound can be initially included in the reaction mixture, or can be added at a time subsequent to the addition of the target gene and its cellular or extracellular binding partner. Control reaction mixtures are incubated without the test compound or with a control compound. The formation of complexes between the target gene product and the cellular or extracellular binding partner is then detected. The formation of a complex in the control reaction, and less formation of complex in the reaction mixture containing the test compound, indicates that the compound interferes with the interaction of the target gene product and the interactive binding partner. Such compounds are candidate compounds for inhibiting the expression or activity or a RIP140. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

Binding assays can be carried out in a liquid phase or in heterogenous formats. In one type of heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

To conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

In another embodiment, modulators of RIP140 expression (RNA or protein) are identified. For example, a cell or cell-free mixture is contacted with a test compound and the expression of RIP140 mRNA or protein evaluated relative to the level of expression of RIP140 mRNA or protein in the absence of the test compound. When expression of RIP140 mRNA or protein is greater in the presence of the test compound than in its absence, the test compound is identified as a stimulator (candidate compound) of RIP140 mRNA or protein expression. Alternatively, when expression of RIP140 mRNA or protein is less (statistically significantly less) in the presence of the test compound than in its absence, the test compound is identified as an inhibitor (candidate compound) of RIP140 mRNA or protein expression. The level of RIP140 mRNA or protein expression can be determined by methods described herein and methods known in the art such as Northern blot or Western blot for detecting RIP140 mRNA or protein.

In another aspect, the new methods described herein pertain to a combination of two or more of the assays described herein. For example, a modulating agent can be identified using a cell-based or a cell-free assay, and the ability of the agent to modulate the activity of a RIP140 protein can be confirmed in vivo, e.g., in an animal such as an animal model for obesity or diabetes (e.g., type II diabetes, e.g., ob/ob mice, db/db mice; see, e.g., Sima A A F, Shafrir E. *Animal Models in Diabetes: A Primer*. Taylor and Francis, Publ Amsterdam, Netherlands, 2000).

This invention further pertains to novel agents identified by the above-described screening assays. Accordingly, it is within the scope of this invention to further use an agent (compound) identified as described herein (e.g., a RIP140 modulating agent, an antisense RIP140 nucleic acid molecule, a RIP140 siRNA, a RIP140-specific antibody, or a RIP140-binding partner) in an appropriate animal model to determine the efficacy, toxicity, side effects, or mechanism of action, of treatment with such an agent. Furthermore, novel agents identified by the above-described screening assays can be used for treatments as described herein.

Compounds that modulate RIP140 expression or activity (RIP140 modulators) can be tested for their ability to affect metabolic effects associated with RIP140, e.g., with decreased expression or activity of RIP140 using methods known in the art and methods described herein. For example, the ability of a compound to modulate glucose transport (in the presence or absence of insulin) can be tested using an assay for 2-deoxyglucose uptake as described in Frost and Lane (*J. Biol. Chem.*, 260:2646-2652, 1985) and glucose conversion to glyceride fatty acids can be assayed as described in DiGirolamo et al. (*J. Lipid Res.*, 15:332-338, 1974). The conversion of white fat to brown fat can be monitored as described by Tiraby et al. (*J. Biol. Chem.*, 278:33370-33376, 2003), e.g., by assaying UCP1 (uncoupling protein 1). An increase in the amount of UCP1 or other indicator of brown fat metabolism indicates that RIP140 expression or activity in inhibited.

RIP140 Modulators

Methods of modulating RIP140 expression or activity can be accomplished using a variety of compounds including nucleic acid molecules that are targeted to a RIP140 nucleic acid sequence or fragment thereof, or to a RIP140 polypeptide. Compounds that may be useful for inhibiting RIP140 expression or activity include polynucleotides, polypeptides, small non-nucleic acid organic molecules, small inorganic molecules, antibodies or fragments thereof, antisense oligonucleotides, siRNAs, and ribozymes. Methods of identifying such compounds are described herein.

RNA Inhibition (RNAi)

Molecules that are targeted to a RIP140 RNA are useful for the methods described herein, e.g., inhibition of RIP140 expression, e.g., for treating type II diabetes. Examples of nucleic acids include siRNAs (e.g., GGAATGAGCTCGATTATAA (SEQ ID NO:1); GGACAAAGGTCATGAGTGA (SEQ ID NO:2), GAATAACGCTGCCACCTTT (SEQ ID NO:3), and GAAACGCGCTCACCATAAA (SEQ ID NO:4)). Other such molecules that function using the mechanisms associated with RNAi can also be used including chemically modified siRNAs and vector driven expression of hairpin RNA that are then cleaved to siRNA. The nucleic acid molecules or constructs that are useful as described herein include dsRNA (e.g., siRNA) molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA, and the other strand is complementary to the first strand. The dsRNA molecules can be chemically synthesized, can transcribed be in vitro from a DNA template, or can be transcribed in vivo from, e.g., shRNA. The dsRNA molecules can be designed using methods known in the art, e.g., Dharmacon.com (see, siDESIGN CENTER) or "The siRNA User Guide," available on the Internet at mpibpc.gwdg.de/abteilungen/100/105/sirna.html.

Negative control siRNAs ("scrambled") generally have the same nucleotide composition as the selected siRNA, but without significant sequence complementarity to the appropriate genome. Such negative controls can be designed by randomly scrambling the nucleotide sequence of the selected siRNA; a homology search can be performed to ensure that the negative control lacks homology to any other gene in the appropriate genome. Controls can also be designed by introducing an appropriate number of base mismatches into the selected siRNA sequence.

The nucleic acid compositions that are useful for the methods described herein include both siRNA and crosslinked siRNA derivatives. Crosslinking can be used to alter the pharmacokinetics of the composition, for example, to increase half-life in the body. Thus, the invention includes siRNA derivatives that include siRNA having two complementary strands of nucleic acid, such that the two strands are crosslinked. For example, a 3' OH terminus of one of the strands can be modified, or the two strands can be crosslinked and modified at the 3'OH terminus. The siRNA derivative can contain a single crosslink (e.g., a psoralen crosslink). In some cases, the siRNA derivative has at its 3' terminus a biotin molecule (e.g., a photocleavable biotin), a peptide (e.g., a Tat peptide), a nanoparticle, a peptidomimetic, organic compounds (e.g., a dye such as a fluorescent dye), or dendrimer. Modifying SiRNA derivatives in this way can improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The nucleic acid compositions described herein can be unconjugated or can be conjugated to another moiety, such as a nanoparticle, to enhance a property of the compositions, e.g., a pharmacokinetic parameter such as absorption, efficacy, bioavailability, and/or half-life. The conjugation can be accomplished using methods known in the art, e.g., using the methods of Lambert et al., *Drug Deliv. Rev.*, 47, 99-112, 2001 (describes nucleic acids loaded to polyalkylcyanoacrylate (PACA) nanoparticles); Fattal et al., *J. Control Release*, 53:137-143, 1998 (describes nucleic acids bound to nanoparticles); Schwab et al., *Ann. Oncol.*, 5 Suppl. 4:55-8, 1994 (describes nucleic acids linked to intercalating agents, hydrophobic groups, polycations or PACA nanoparticles); and Godard et al., *Eur. J. Biochem.*, 232:404-410, 1995 (describes nucleic acids linked to nanoparticles).

The nucleic acid molecules can also be labeled using any method known in the art; for instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the molecule can be radiolabeled, e.g., using $^3$H, $^{32}$P, or other appropriate isotope.

Synthetic siRNAs can be delivered into cells by cationic liposome transfection and electroporation. Sequences that are modified to improve their stability can be used. Such modifications can be made using methods known in the art (e.g., siSTABLE™, Dharmacon). Such stabilized molecules are particularly useful for in vivo methods such as for administration to a subject to decrease RIP140 expression. Longer term expression can also be achieved by delivering a vector that expresses the siRNA molecule (or other nucleic acid) to a cell, e.g., a fat, liver, or muscle cell. Several methods for expressing siRNA duplexes within cells from recombinant DNA constructs allow longer-term target gene suppression in cells, including mammalian Pol III promoter systems (e.g., H1 or U6/snRNA promoter systems (Tuschl, *Nature Biotechnol.*, 20:440-448, 2002) capable of expressing functional double-stranded siRNAs; (Bagella et al., *J. Cell. Physiol.*, 177:206-213, 1998; Lee et al., *Nature Biotechnol.*, 20:500-505, 2002; Paul et al., *Nature Biotechnol.*, 20:505-508, 2002; Yu et al., *Proc. Natl. Acad. Sci. USA*, 99(9):6047-6052, 2002; Sui et al., *Proc. Natl. Acad. Sci. USA*, 99(6):5515-5520, 2002). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al., 1998, supra; Lee et al., 2002, supra; Paul et al., 2002, supra; Yu et al., 2002, supra; Sui et al., 2002, supra). Constructs containing siRNA sequence under the control of T7 promoter also make functional siRNAs when cotransfected into the cells with a vector expression T7 RNA polymerase (Jacque, *Nature*, 418:435-438, 2002).

Animal cells express a range of noncoding RNAs of approximately 22 nucleotides termed micro RNA (miRNAs) and can regulate gene expression at the post transcriptional or translational level during animal development. miRNAs are excised from an approximately 70 nucleotide precursor RNA stem-loop. By substituting the stem sequences of the miRNA precursor with miRNA sequence complementary to the target mRNA, a vector construct that expresses the novel miRNA can be used to produce siRNAs to initiate RNAi against specific mRNA targets in mammalian cells (Zeng, *Mol. Cell*, 9:1327-1333, 2002). When expressed by DNA vectors containing polymerase III promoters, micro-RNA designed hairpins can silence gene expression (McManus, RNA 8:842-850, 2002). Viral-mediated delivery mechanisms can also be used to induce specific silencing of targeted genes through expression of siRNA, for example, by generating recombinant adenoviruses harboring siRNA under RNA Pol II promoter transcription control (Xia et al., *Nat. Biotechnol.*, 20(10): 1006-10, 2002).

Injection of the recombinant adenovirus vectors into transgenic mice expressing the target genes of the siRNA results in in vivo reduction of target gene expression (id). In an animal model, whole-embryo electroporation can efficiently deliver synthetic siRNA into post-implantation mouse embryos (Calegari et al., *Proc. Natl. Acad. Sci. USA*, 99:14236-14240, 2002). In adult mice, efficient delivery of siRNA can be accomplished by "high-pressure" delivery technique, a rapid injection (within 5 seconds) of a large volume of siRNA containing solution into animal via the tail vein (Liu, *Gene Ther.*, 6:1258-1266, 1999; McCaffrey, *Nature*, 418:38-39, 2002; Lewis, *Nature Genetics*, 32:107-108, 2002). Nanoparticles and liposomes can also be used to deliver siRNA into animals. Likewise, in some embodiments, viral gene delivery, direct injection, nanoparticle particle-mediated injection, or liposome injection may be used to express siRNA in humans.

In some cases, a pool of siRNAs is used to modulate the expression of RIP140. The pool is composed of at least 2, 3, 4, 5, 8, or 10 different sequences targeted to RIP140.

SiRNAs or other compositions that inhibit RIP140 expression or activity are effective for ameliorating undesirable effects of a disorder related to glucose transport when RIP140 RNA levels are reduced by at least 25%, 50%, 75%, 90%, or 95%. In some cases, it is desired that RIP140 RNA levels be reduced by not more than 10%, 25%, 50%, or 75%. Methods of determining the level of RIP140 expression can be determined using methods known in the art. For example, the level of RIP140 RNA can be determined using Northern blot detection on a sample from a cell line or a subject. Levels of RIP140 protein can also be measured using, e.g., an immunoassay method.

Antisense Nucleic Acids

Antisense nucleic acids are useful for inhibiting RIP140. Such antisense nucleic acid molecules, i.e., nucleic acid molecules whose nucleotide sequence is complementary to all or part of an mRNA encoding a RIP140. An antisense nucleic acid molecule can be antisense to all or part of a non-coding region of the coding strand of a nucleotide sequence encoding a polypeptide of the invention. The non-coding regions ("5' and 3' untranslated regions") are the 5' and 3' sequences that flank the coding region and are not translated into amino acids.

Based upon the sequences disclosed herein, one of skill in the art can easily choose and synthesize any of a number of appropriate antisense molecules to target a gene described herein. For example, a "gene walk" comprising a series of oligonucleotides of 15-30 nucleotides spanning the length of a nucleic acid (e.g., a RIP140 nucleic acid) can be prepared, followed by testing for inhibition of expression of the gene. Optionally, gaps of 5-10 nucleotides can be left between the oligonucleotides to reduce the number of oligonucleotides synthesized and tested.

An antisense oligonucleotide can be, for example, about 5, 10, 15, 20, 25, 30, 35, 40, 45, or 50 nucleotides or more in length. An antisense nucleic acid described herein can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-s methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The new antisense nucleic acid molecules can be administered to a mammal, e.g., a human patient. Alternatively, they can be generated in situ such that they hybridize with or bind to cellular mRNA and/or genomic DNA encoding a selected polypeptide to thereby inhibit expression, e.g., by inhibiting transcription and/or translation. The hybridization can be by conventional nucleotide complementarities to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. For example, to achieve sufficient intracellular concentrations of the antisense molecules, vector constructs can be used in which the antisense nucleic acid molecule is placed under the control of a strong pol II or pol III promoter.

An antisense nucleic acid molecule can be an α-anomeric nucleic acid molecule. An α-anomeric nucleic acid molecule forms specific double-stranded hybrids with complementary RNA in which, contrary to the usual, β-units, the strands run parallel to each other (Gaultier et al., *Nucleic Acids Res.*, 15:6625-6641, 1987). The antisense nucleic acid molecule can also comprise a 2'-o-methylribonucleotide (Inoue et al., *Nucleic Acids Res.*, 15:6131-6148, 1987) or a chimeric RNA-DNA analog (Inoue et al., *FEBS Lett.*, 215:327-330, 1987).

Antisense molecules that are complementary to all or part of a glucose transport-related gene are also useful for assaying expression of such genes using hybridization methods known in the art. For example, the antisense molecule can be labeled (e.g., with a radioactive molecule) and an excess amount of the labeled antisense molecule is hybridized to an RNA sample. Unhybridized labeled antisense molecule is removed (e.g., by washing) and the amount of hybridized antisense molecule measured. The amount of hybridized molecule is measured and used to calculate the amount of expression of the glucose transport-related gene. In general, antisense molecules used for this purpose can hybridize to a sequence from a glucose transport-related gene under high stringency conditions such as those described herein. When the RNA sample is first used to synthesize cDNA, a sense molecule can be used. It is also possible to use a double-stranded molecule in such assays as long as the double-stranded molecule is adequately denatured prior to hybridization.

Ribozymes

Ribozymes that have specificity for a RIP140 nucleic acid sequence can also be used to inhibit RIP140 expression. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haseloff and Gerlach, *Nature*, 334:585-591, 1988)) can be used to catalytically cleave mRNA transcripts to thereby inhibit translation of the protein encoded by the mRNA. Methods of designing and producing ribozymes are known in the art (see, e.g., Scanlon, 1999, *Therapeutic Applications of Ribozymes*, Humana Press). A ribozyme having specificity for a RIP140 nucleic acid molecule or fragment thereof can be designed based upon the nucleotide sequence of a RIP140 cDNA. For example, a derivative of a *Tetrahymena* L-19 IVS RNA can be constructed in which the nucleotide sequence of the active site is complementary to the nucleotide sequence to be cleaved in a RIP140 RNA (Cech et al. U.S. Pat. No. 4,987,071; and Cech et al., U.S. Pat. No. 5,116,742). Alternatively, an mRNA encoding a RIP140 or fragment thereof can be used to select a catalytic RNA having a specific ribonuclease activity from a pool of RNA molecules (See, e.g., Bartel and Szostak, *Science*, 261:1411-1418, 1993).

Nucleic acid molecules that form triple helical structures can also be used to modulate RIP140 expression. For example, expression of a RIP140 polypeptide can be inhibited by targeting nucleotide sequences complementary to the regulatory region of the gene encoding the polypeptide (e.g., the promoter and/or enhancer) to form triple helical structures that prevent transcription of the gene in target cells. See generally Helene, *Anticancer Drug Des.*, 6(6):569-84, 1991; Helene, *Ann. N.Y. Acad. Sci.*, 660:27-36, 1992; and Maher, *Bioassays*, 14(12):807-15, 1992.

A nucleic acid molecule for use as described herein can be modified at the base moiety, sugar moiety or phosphate backbone to improve, e.g., the stability, hybridization, or solubility of the molecule. For example, the deoxyribose phosphate backbone of a nucleic acid can be modified to generate peptide nucleic acids (see Hyrup et al., *Bioorganic & Medicinal Chem.*, 4(1): 5-23, 1996). Peptide nucleic acids (PNAs) are nucleic acid mimics, e.g., DNA mimics, in which the deoxyribose phosphate backbone is replaced by a pseudopeptide backbone and only the four natural nucleobases are retained. The neutral backbone of PNAs allows for specific hybridization to DNA and RNA under conditions of low ionic strength. The synthesis of PNA oligomers can be performed using standard solid phase peptide synthesis protocols, e.g., as described in Hyrup et al., 1996, supra; Perry-O'Keefe et al., *Proc. Natl. Acad. Sci. USA*, 93: 14670-675, 1996.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup, 1996, supra; or as probes or primers for DNA sequence and hybridization (Hyrup, 1996, supra; Perry-O'Keefe et al., *Proc. Natl. Acad. Sci. USA*, 93: 14670-675, 1996).

PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup, 1996, supra, and Finn et al., *Nucleic Acids Res.*, 24:3357-63, 1996. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., *Nucleic Acids Res.*, 17:5973-88, 1989). PNA monomers are then coupled in a stepwise manner to produce a chimeric molecule with a 5' PNA segment and a 3' DNA segment (Finn et al., *Nucleic Acids Res.*, 24:3357-63, 1996). Alternatively, chimeric molecules can be synthesized with a 5' DNA segment and a 3' PNA segment (Peterser et al., *Bioorganic Med. Chem. Lett.*, 5:1119-11124, 1975).

A nucleic acid targeting a RIP140 nucleic acid sequence can include appended groups such as peptides (e.g., for targeting host cell receptors in vivo), or agents facilitating transport across the cell membrane (see, e.g., Letsinger et al., *Proc. Natl. Acad. Sci. USA*, 86:6553-6556, 1989; Lemaitre et al., *Proc. Natl. Acad. Sci. USA*, 84:648-652, 1989; WO 88/09810) or the blood-brain barrier (see, e.g., WO 89/10134). In addition, oligonucleotides can be modified with hybridization-triggered cleavage agents (see, e.g., Krol et al., *Bio/Techniques*, 6:958-976, 1988) or intercalating agents (see, e.g., Zon, *Pharm. Res.*, 5:539-549, 1988). To this end, the oligonucleotide may be conjugated to another molecule, e.g., a peptide, hybridization triggered cross-linking agent, transport agent, or a hybridization-triggered cleavage agent.

RIP140 Polypeptides

Isolated RIP140 polypeptides, fragments thereof, and variants thereof are provided herein. These polypeptides can be used, e.g., as immunogens to raise antibodies, in screening methods, or in methods of treating subjects, e.g., by administration of the polypeptides. An "isolated" or "purified" polypeptide or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of polypeptides in which the polypeptide of interest is separated from cellular components of the cells from which it is isolated or recombinantly produced. Thus, a polypeptide that is substantially free of cellular material includes preparations of polypeptides having less than about 30%, 20%, 10%, or 5% (by dry weight) of heterologous protein (also referred to herein as "contaminating protein"). In general, when the polypeptide or biologically active portion thereof is recombinantly produced, it is also substantially free of culture medium, i.e., culture medium represents less than about 20%, 10%, or 5% of the volume of the protein preparation. In general, when the polypeptide is produced by chemical synthesis, it is substantially free of chemical precursors or other chemicals, i.e., it is separated from chemical precursors or other chemicals that are involved in the synthesis of the polypeptide. Accordingly such preparations of the polypeptide have less than about 30%, 20%, 10%, or 5% (by dry weight) of chemical precursors or compounds other than the polypeptide of interest.

Expression of polypeptides can be assayed to determine the amount of expression. Methods for assaying protein expression are known in the art and include Western blot, immunoprecipitation, and radioimmunoassay.

As used herein, a "biologically active portion" of a RIP140 protein includes a fragment of a RIP140 protein that participates in an interaction between a RIP140 molecule and a non-RIP140 molecule (e.g., a PPAR). Biologically active portions of a RIP140 protein include peptides including amino acid sequences sufficiently homologous to the amino acid sequence of a RIP140 protein that includes fewer amino acids than a full-length RIP140 protein, and exhibits at least one activity of a RIP140 protein. Typically, biologically active portions include a domain or motif with at least one activity of the RIP140 protein (e.g., an LXXLL motif, or a PXDLS motif). A biologically active portion of a RIP140 protein can be a polypeptide that is, for example, 10, 25, 50, 100, 200 or more amino acids in length. Biologically active portions of a RIP140 protein can be used as targets for developing agents that modulate a RIP140 mediated activity, e.g., compounds that inhibit RIP140 activity and result in at least one of increased insulin sensitivity, increased glucose transport, increased energy expenditure, increased metabolism, or increased fatty acid oxidation.

In some embodiments, the RIP140 polypeptide has a sequence identical to a sequence disclosed herein (e.g., a human RIP140 amino acid sequence found under GenBank® Acc. No. Accession No. NP_003480). Other useful polypeptides are substantially identical (e.g., at least about 45%, 55%, 65%, 75%, 85%, 95%, or 99%) to the sequence found under Accession No. NP_003480 and (a) retains the functional activity of RIP140 yet differs in amino acid sequence due to natural allelic variation or mutagenesis, or (b) exhibit an altered functional activity (e.g., as a dominant negative) where desired. Provided herein are variants that have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the polypeptide. An antagonist of a polypeptide can inhibit one or more of the activities of the naturally occurring form of the polypeptide by, for example, competitively binding to a downstream or upstream member of a cellular signaling cascade that includes the polypeptide. Thus, specific biological effects can be elicited by treatment with a variant of limited function. Treatment of a subject with a variant having a subset of the biological activities of the naturally occurring form of the polypeptide can have fewer side effects in a subject relative to treatment with the naturally occurring form of the polypeptide. In some embodiments, the variant RIP140 polypeptide is a dominant negative form of RIP140. Dominant negatives are desired, e.g., in methods in which inhibition of RIP140 action is desired, e.g., to achieve inhibition of glucose transport and/or treatment of a metabolic disorder such as diabetes.

Also provided herein are chimeric or fusion proteins.

The comparison of sequences and determination of percent identity between two sequences is accomplished using a mathematical algorithm. The percent identity between two amino acid sequences is determined using the Needleman and Wunsch, *J. Mol. Biol.*, 48:444-453, 1970) algorithm, which has been incorporated into the GAP program in the GCG software package (available on the Internet at gcg.com), using either a Blossum 62 matrix or a PAM250 matrix, and a gap weight of 16 and a length weight of 1. The percent identity between two nucleotide sequences is determined using the GAP program in the GCG software package (also available on the Internet at gcg.com), using a NWSgapdna.CMP matrix, a gap weight of 40, and a length weight of 1.

In general, percent identity between amino acid sequences referred to herein is determined using the BLAST 2.0 program, which is available to the public on the Internet at ncbi.nlm.nih.gov/BLAST. Sequence comparison is performed using an ungapped alignment and using the default parameters (Blossum 62 matrix, gap existence cost of 11, per residue gap cost of 1, and a lambda ratio of 0.85). The mathematical algorithm used in BLAST programs is described in Altschul et al., *Nucleic Acids Research* 25:3389-3402, 1997.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a RIP140 protein is generally replaced with another amino acid residue from the same side chain family. Alternatively, mutations can be introduced randomly along all or part of a RIP140 coding sequence, such as by saturation mutagenesis, and the resultant mutants can be screened for RIP140 biological activity to identify mutants that retain activity. The encoded protein can be expressed recombinantly and the activity of the protein can be determined.

Antibodies

A RIP140 polypeptide, or a fragment thereof, can be used as an immunogen to generate antibodies using standard techniques for polyclonal and monoclonal antibody preparation. The full-length polypeptide or protein can be used or, alternatively, antigenic peptide fragments can be used as immunogens. The antigenic peptide of a protein comprises at least 8 (e.g., at least 10, 15, 20, or 30) amino acid residues of the amino acid sequence of a RIP140 polypeptide, and encompasses an epitope of RIP140 such that an antibody raised against the peptide forms a specific immune complex with the polypeptide.

An immunogen typically is used to prepare antibodies by immunizing a suitable subject (e.g., rabbit, goat, mouse or other mammal). An appropriate immunogenic preparation can contain, for example, a recombinantly expressed or a chemically synthesized polypeptide. The preparation can further include an adjuvant, such as Freund's complete or incomplete adjuvant, or similar immunostimulatory agent.

Polyclonal antibodies can be prepared as described above by immunizing a suitable subject with a RIP140 polypeptide as an immunogen. The antibody titer in the immunized subject can be monitored over time by standard techniques, such as with an enzyme linked immunosorbent assay (ELISA) using immobilized polypeptide. If desired, the antibody molecules can be isolated from the mammal (e.g., from the blood) and further purified by well-known techniques, such as protein A chromatography to obtain the IgG fraction. At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein, *Nature*, 256:495-497, 1975, the human B cell hybridoma technique (Kozbor et al., *Immunol. Today*, 4:72, 1983), the EBV-hybridoma technique (Cole et al., *Monoclonal Antibodies and Cancer Therapy*, Alan R. Liss, Inc., pp. 77-96, 1985) or trioma techniques. The technology for producing hybridomas is well known (see generally *Current Protocols in Immunology*, 1994, Coligan et al. (eds.) John Wiley & Sons, Inc., New York, N.Y.). Hybridoma cells producing a monoclonal antibody are detected by screening the hybridoma culture supernatants for antibodies that bind the polypeptide of interest, e.g., using a standard ELISA assay.

As an alternative to preparing monoclonal antibody-secreting hybridomas, a monoclonal antibody directed against a polypeptide can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System*, Catalog No. 27-9400-01; and the Stratagene SurfZAP™ *Phage Display Kit*, Catalog No. 240612). Additionally, examples of methods and reagents particularly amenable for use in generating and screening antibody display library can be found in, for example, U.S. Pat. No. 5,223,409; WO 92/18619; WO 91/17271; WO 92/20791; WO 92/15679; WO 93/01288; WO 92/01047; WO 92/09690; WO 90/02809; Fuchs et al., *Bio/Technology*, 9:1370-1372, 1991; Hay et al., *Hum. Antibod. Hybridomas*, 3:81-85, 1992; Huse et al., *Science*, 246:1275-1281, 1989; Griffiths et al., *EMBO J.*, 12:725-734, 1993.

Additionally, recombinant antibodies, such as chimeric and humanized monoclonal antibodies, including both human and non-human portions, which can be made using standard recombinant DNA techniques, are provided herein. Such chimeric and humanized monoclonal antibodies can be produced by recombinant DNA techniques known in the art, for example using methods described in WO 87/02671; European Patent Application 184,187; European Patent Application 171,496; European Patent Application 173,494; WO 86/01533; U.S. Pat. No. 4,816,567; European Patent Application 125,023; Better et al., *Science*, 240:1041-1043, 1988; Liu et al., *Proc. Natl. Acad. Sci. USA* 84:3439-3443, 1987; Liu et al., *J. Immunol.*, 139:3521-3526, 1987; Sun et al., *Proc. Natl. Acad. Sci. USA*, 84:214-218, 1987; Nishimura et al., *Canc. Res.*, 47:999-1005, 1987; Wood et al., *Nature*, 314: 446-449, 1985; and Shaw et al., *J. Natl. Cancer Inst.*, 80:1553-1559, 1988); Morrison, Science, 229:1202-1207, 1985; Oi et al., *Bio/Techniques*, 4:214, 1986; U.S. Pat. No. 5,225,539; Jones et al., *Nature*, 321:552-525, 1986; Verhoeyan et al., *Science*, 239:1534, 1988; and Beidler et al., *J. Immunol.*, 141:4053-4060, 1988.

Completely human antibodies are particularly desirable for therapeutic treatment of human patients. Such antibodies can be produced using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, and IgE antibodies. For an overview of this technology for producing human antibodies, see Lonberg and Huszar (*Int. Rev. Immunol.*, 13:65-93, 1995). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. (Jespers et al., *Biotechnology*, 12:899-903, 1994).

An antibody directed against RIP140 can be used to detect the polypeptide (e.g., in a cellular lysate or cell supernatant) to evaluate its abundance and pattern of expression. The antibodies can also be used diagnostically to monitor protein levels in tissue as part of a clinical testing procedure, e.g., for example, to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Pharmaceutical Compositions

A test compound that has been screened by a method described herein and determined to modulate RIP140 expression or activity, can be considered a candidate compound. A candidate compound that has been screened, e.g., in an in vivo model of a diabetes or obesity, and determined to have a desirable effect on the disorder, e.g., by increasing glucose transport, reducing glucose levels in vivo, or reducing insulin levels, can be considered a candidate therapeutic agent. Candidate therapeutic agents, once screened in a clinical setting, are therapeutic agents. Candidate therapeutic agents and therapeutic agents can be optionally optimized and/or derivatized, and formulated with physiologically acceptable excipients to form pharmaceutical compositions.

The compounds described herein that can modulate RIP140 expression or activity (e.g., can modulate the interaction between RIP140 and a PPAR) can be incorporated into pharmaceutical compositions. Such compositions typically include the compound and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. A parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be desirable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the methods of preparation can include vacuum drying or freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. Dosage units can also be accompanied by instructions for use.

Toxicity and therapeutic efficacy of such compounds can be determined known pharmaceutical procedures in cell cultures (e.g., in cultures of fat cells, muscle cells, or liver cells) or experimental animals (animal models of obesity or of diabetes (e.g., type II diabetes). These procedures can be used, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in to minimize potential damage to uninfected cells and, thereby, reduce side effects.

The data obtained from the cell culture assays and animal studies can be used in formulating a range of dosage for use in humans. The dosage of such compounds lies generally within a range of circulating concentrations that include the ED50 with little or no toxicity. The dosage may vary within this range depending upon the dosage form employed and the route of administration utilized. For a compound used as described herein (e.g., for treating diabetes in a subject), the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, about 0.01 to 25 mg/kg body weight, about 0.1 to 20 mg/kg body weight, about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, generally between 2 to 8 weeks, between about 3 to 7 weeks, or for about 4, 5, or 6 weeks. One in the art will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or can include a series of treatments. In the case of a subject suffering from diabetes, blood glucose levels can be monitored and the dosages adjusted accordingly.

For antibodies or a fragment thereof, the dosage is about 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible with such species-matched antibodies. Modifications such as lipidation can be used to stabilize antibodies and to enhance uptake and tissue penetration (e.g., into the brain). A method for lipidation of antibodies is described by Cruikshank et al. (*J. Acquired Immune Deficiency Syndromes and Human Retrovirology*, 14:193, 1997).

Compounds that modulate expression or activity of a RIP140 are described herein. Such a compound can be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) to modulate expression or activity of a polypeptide or nucleic acid of the invention, a physician, veterinarian, or researcher may, for example, prescribe a relatively low dose at first, subsequently increasing the dose until an appropriate response is obtained (e.g., an appropriate blood glucose level). In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) can be conjugated to a therapeutic moiety such as a cytotoxin, a therapeutic agent, or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

A nucleic acid molecule that is useful for modulating RIP140 expression or activity can be inserted into a vector and the resulting vector used as gene therapy vector. Gene therapy vectors can be delivered to a subject by, for example, intravenous injection, local administration (see U.S. Pat. No. 5,328,470) or by stereotactic injection (see e.g., Chen et al. (*Proc. Natl. Acad. Sci. USA*, 91:3054-3057, 1994). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

Compounds described herein and those identified as described herein can be used to treat a subject that is at risk for or has a glucose transport-related disorder such as type II diabetes. Methods of identifying such individuals are known in the art. Thus, methods and compositions for both prophylactic and therapeutic methods of treating a subject at risk of (or susceptible to) a disorder or having a disorder associated with aberrant or unwanted RIP140 expression or activity are described herein. As used herein, the term "treatment" is defined as the application or administration of a therapeutic compound to a patient, or application or administration of a therapeutic compound to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic compound includes, but is not limited to, small molecules such as small non-nucleic acid organic molecules, small inorganic molecules, peptides, synthetic peptides, antibodies, natural nucleic acid molecules (such as ribozymes, siRNAs, and antisense oligonucleotides), and molecules containing nucleic acid analogs.

Provided herein are methods for preventing in a subject (e.g., a human), a disease or condition associated with an aberrant or unwanted RIP140 expression or activity, by administering to the subject a RIP140 or an compound that modulates RIP140 expression or at least one RIP140 activity (e.g., RIP140 interaction with a PPAR such as PPARgamma). Subjects at risk for a disease that is caused or contributed to by aberrant or unwanted RIP140 expression or activity can be identified by, for example, any or a combination of diagnostic or prognostic assays as described herein. Administration of a prophylactic compound can occur prior to the manifestation of symptoms characteristic of full-blown disease, e.g., a subject exhibiting hyperglycemia but that does not exhibit effects of diabetes associated with advanced disease, such that the disease or disorder is prevented or, alternatively, delayed in its progression. Methods known in the art can be used to determine the efficacy of the treatment. The appropriate compound used for treating the subject can be determined based on screening assays described herein.

It is possible that some cases of diabetes are caused, at least in part, by an abnormal level of RIP140 gene product, or by the presence of a RIP140 gene product exhibiting abnormal activity (e.g., increased repressor activity compared to a wild type RIP140). As such, the reduction in the level and/or activity of such gene products will bring about the amelioration of disorder symptoms.

As discussed, successful treatment of glucose transport-related disorders can be brought about by techniques that serve to inhibit the expression or activity of target gene products. For example, compounds, e.g., an agent identified using one or more of the assays described above, that proves to exhibit negative modulatory activity, can be used as described herein to prevent and/or ameliorate symptoms of glucose transport-related disorders. Such molecules can include, but are not limited to, peptides, phosphopeptides, small organic or inorganic molecules, or antibodies (including, for example, polyclonal, monoclonal, humanized, anti-idiotypic, chimeric or single chain antibodies, and Fab, F(ab')$_2$ and Fab expression library fragments, scFV molecules, and epitope-binding fragments thereof).

Further, siRNA, antisense, and ribozyme molecules that inhibit expression of a RIP140 gene can also be used in accordance with the methods described herein to reduce the level of RIP140 expression, thus effectively reducing the level of RIP140 activity. Triple helix molecules can be utilized to reduce the level of RIP140 activity. Such nucleic acid molecules are discussed above and in the Examples.

Another method by which nucleic acid molecules can be utilized in treating or preventing a disease that can be treated by modulating RIP140 expression is through the use of aptamer molecules specific for RIP140 protein. Aptamers are nucleic acid molecules having a tertiary structure that permits them to specifically bind to protein ligands (e.g., Osborne, et al., *Curr. Opin. Chem. Biol.*, 1: 5-9, 1997; and Patel, *Curr. Opin. Chem. Biol.*, 1:32-46, 1997). Since nucleic acid molecules may be more conveniently introduced into target cells than therapeutic protein molecules may be, aptamers offer a method by which RIP140 protein activity can be specifically decreased without the introduction of drugs or other molecules that may have pluripotent effects.

An antibody that specifically recognizes a RIP140 can also be used. Since RIP140 is intracellular, if a whole antibody is used, internalizing antibodies are used. Lipofectin® or liposomes can be used to deliver the antibody or a fragment of the Fab region that binds to the RIP140 in a cell. Where fragments of the antibody are used, the smallest inhibitory fragment that binds to the target antigen is generally used. For example, peptides having an amino acid sequence corresponding to the Fv region of the antibody can be used. Alternatively, single chain neutralizing antibodies that bind to intracellular RIP140 can also be administered. Such single chain antibodies can be administered, for example, by expressing nucleotide sequences encoding single-chain antibodies within the target cell population (e.g., Marasco et al., *Proc. Natl. Acad. Sci. USA*, 90:7889-7893, 1993).

The identified compounds that inhibit RIP140 gene expression, synthesis and/or activity can be administered to a patient at therapeutically effective doses to prevent, treat, or ameliorate RIP140 disorders. A therapeutically effective dose refers to that amount of the compound sufficient to result in amelioration of symptoms of the disorders. Toxicity and therapeutic efficacy of such compounds can be determined by standard pharmaceutical procedures as described above.

The data obtained from the cell culture assays and animal studies can be used in formulating a range of dosage for use in humans. The dosage of such compounds lies generally within a range of circulating concentrations that include the $ED_{50}$ with little or no toxicity. The dosage can vary within this range depending upon the dosage form employed and the route of administration utilized. For any compound used as described herein, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays may utilize antibody mimics and/or "biosensors" that have been created through molecular imprinting techniques.

The compound that is able to modulate RIP140 activity is used as a template, or "imprinting molecule," to spatially organize polymerizable monomers prior to their polymerization with catalytic reagents. The subsequent removal of the imprinted molecule leaves a polymer matrix that contains a repeated "negative image" of the compound and is able to selectively rebind the molecule under biological assay conditions. A detailed review of this technique can be seen in Ansell et al., *Current Opinion in Biotechnology*, 7:89-94, 1996 and in Shea (*Trends in Polymer Science*, 2:166-173, 1994). Such "imprinted" affinity matrixes are amenable to ligand-binding assays, whereby the immobilized monoclonal antibody component is replaced by an appropriately imprinted matrix. An example of the use of such matrixes in this way can be seen in Vlatakis et al. (*Nature*, 361:645-647, 1993). Through the use of isotope-labeling, the "free" concentration of compound that modulates the expression or activity of RIP140 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz et al., *Analytical Chemistry*, 67:2142-2144, 1995.

RIP140 expression or activity can be modulated for therapeutic purposes. Accordingly, in an exemplary embodiment, the modulatory methods described herein involve contacting a cell with a compound that modulates one or more of the activities of RIP140 protein activity (e.g., RIP140 binding to a PPAR), associated with the cell. A compound that modulates RIP140 activity can be a compound as described herein, such as a nucleic acid or a protein, a naturally-occurring target molecule of a RIP140 protein (e.g., a RIP140 substrate or receptor), a RIP140 antibody, a RIP140 agonist or antagonist, a peptidomimetic of a RIP140 agonist or antagonist, or other small molecule.

In one embodiment, the compound stimulates one or more RIP140 activities. Examples of such stimulatory compounds include active RIP140 protein and a nucleic acid molecule encoding RIP140. In another embodiment, the compound inhibits one or more RIP140 activities. Examples of such inhibitory compounds include antisense RIP140 nucleic acid molecules, antiRIP140 antibodies, and RIP140 inhibitors. These modulatory methods can be performed in vitro (e.g., by culturing cells with the compound and returning the cells to a subject) or, alternatively, in vivo (e.g., by administering the compound to a subject). As such, the new methods include treating an individual afflicted with a disease or disorder characterized by aberrant or unwanted expression or activity of a RIP140 protein or nucleic acid molecule (e.g., type II diabetes). In one embodiment, the new methods involve administering a compound (e.g., a compound identified by a screening assay described herein), or combination of compounds that modulate (e.g., up regulates or down regulates) RIP140 expression or activity. In another embodiment, the methods involve administering a RIP140 protein or nucleic acid molecule as therapy to compensate for reduced, aberrant, or unwanted RIP140 expression or activity.

Stimulation of RIP140 activity is desirable in situations in which RIP140 is abnormally downregulated and/or in which increased RIP140 activity is likely to have a beneficial effect. For example, stimulation of RIP140 activity is desirable in situations in which a RIP140 is downregulated and/or in which increased RIP140 activity is likely to have a beneficial effect. Likewise, inhibition of RIP140 activity is desirable in situations in which RIP140 is abnormally upregulated and/or in which decreased RIP140 activity is likely to have a beneficial effect.

The invention is further illustrated by the following examples. The examples are provided for illustrative purposes only. They are not to be construed as limiting the scope or content of the invention in any way.

EXAMPLES

Example 1

Knockdown of RIP140 Potentiates Insulin-Stimulated Phosphorylation of Akt Protein Kinase RIP140 siRNA was selected as a candidate for regulation of glucose metabolism based on a screen using different sets of sequences expressed in mice having different metabolic profiles related to glucose metabolism (FIG. 5).

To test the role of RIP140 in insulin-related cellular responses, siRNAs were transfected into cultured adipose cells (differentiated 3T3-L1 adipocytes). siRNAs that were scrambled (nonsense), targeted to Akt, targeted to PTEN, or targeted to RIP140 were introduced into cultured cells. SiRNAs were obtained from Dharmacon. A mixture of siRNAs was used for the RIP140 knockdown. The mixture included the following sequences that are based on the RIP140 sequence found under GenBank® Acc. No. NM_173440: GGAATGAGCTCGATTATAA (SEQ ID NO:1); GGACAAAGGTCATGAGTGA (SEQ ID NO:2), GAATAACGCTGCCACCTTT (SEQ ID NO:3), and GAAACGCGCTCACCATAAA (SEQ ID NO:4).

Differentiated 3T3-L1 adipocyte cultures (day 4 or 5) having a minimum of 90% adipocytes were transfected with 6 nmol siRNA (experimental) per 150 µl cells ($9 \times 10^6$ cells/ml). Cells transfected with Akt were transfected with 30 nmol Akt2B and 20 nmol Akt1B siRNAs. Cells transfected with PTEN were transfected with 30 nm siRNA. Transfection was performed using electroporation.

Briefly, differentiated 3T3-L1 adipocytes (day 4 or 5) were transfected with siRNAs and plated. Cells were washed in PBS, 0.5% fat cell BSA in DMEM was added, and the cells were serum starved overnight. Insulin was then added to the plates (0 nM, 1.0 nM, or 100 nM in 0.5% BSA in DMEM) for 30 minutes then assayed for phosphorylation of the protein kinase Akt using an enzyme-linked immunosorbant assay. The level of Akt phosphorylation is expressed as absorbance an $OD_{490}$.

Insulin increased the amount of Akt phosphorylation. Knockdown of RIP140 increased the amount of Akt phosphorylation in the absence of insulin and increased the level of Akt phosphorylation in the presence of insulin over the level observed in control, insulin-treated cells (FIG. 2). PTEN knockdown served as a positive control since inhibition of PTEN results in the constitutive activation of the Akt pathway.

These data demonstrate that inhibition of RIP140 (e.g., inhibition of expression using siRNA) can increase the cellular response to insulin. Thus, inhibition of RIP140 is useful for increasing glucose transport and is useful for treating disorders in which it is desirable to increase such transport (e.g., type II diabetes).

Example 2

Knockdown of RIP140 Potentiates Insulin Action on Deoxyglucose Transport into Cultured Fat Cells To further examine the role of RIP140 in glucose transport, the effect of RIP140 inhibition on deoxyglucose transport was assayed. Briefly, differentiated 3T3-L1 adipocytes were seeded at 150,000 cells per well in 24 well plates and then siRNA targeted to PTEN, RIP or scrambled (control) was introduced as described above. Insulin was then added to the plates (0 nM, 0.1 nM, or 100 nM) for 30 minutes. Cells were then assayed for 2-deoxyglucose uptake as described in Frost and Lane (*J. Biol. Chem.*, 260:2646-2652, 1985).

It was observed that knockdown of RIP140 increased the amount of deoxyglucose transport in insulin treated cells to an even greater extent than in cells than in control cells incubated in the same concentration of insulin (FIG. 3).

Additional experiments were performed assaying deoxyglucose in cultured adipose cells using siRNA targeted to Anax8 (annexin A8), Aqp7 (aquaporin 7), TUG, Smpd1 (sphingomyelin phosphodiesterase 1), Nrip1 (RIP140), PTEN, Akt, and scrambled (FIG. 4) in the presence or absence of insulin. These experiments further demonstrate the large increase in deoxyglucose uptake in adipose cells when RIP140 is inhibited compared to the level of increase in during inhibition of the other sequences. As above, the increase in deoxyglucose uptake is even greater when RIP140 is inhibited than in the positive control (PTEN).

These data further demonstrate that RIP140 can affect glucose transport and that inhibition of RIP140 is an effective method of increasing glucose transport and related metabolic activity.

Example 3

RIP140 Depletion Selectively Enhances GLUT4 Expression

Figure 6:
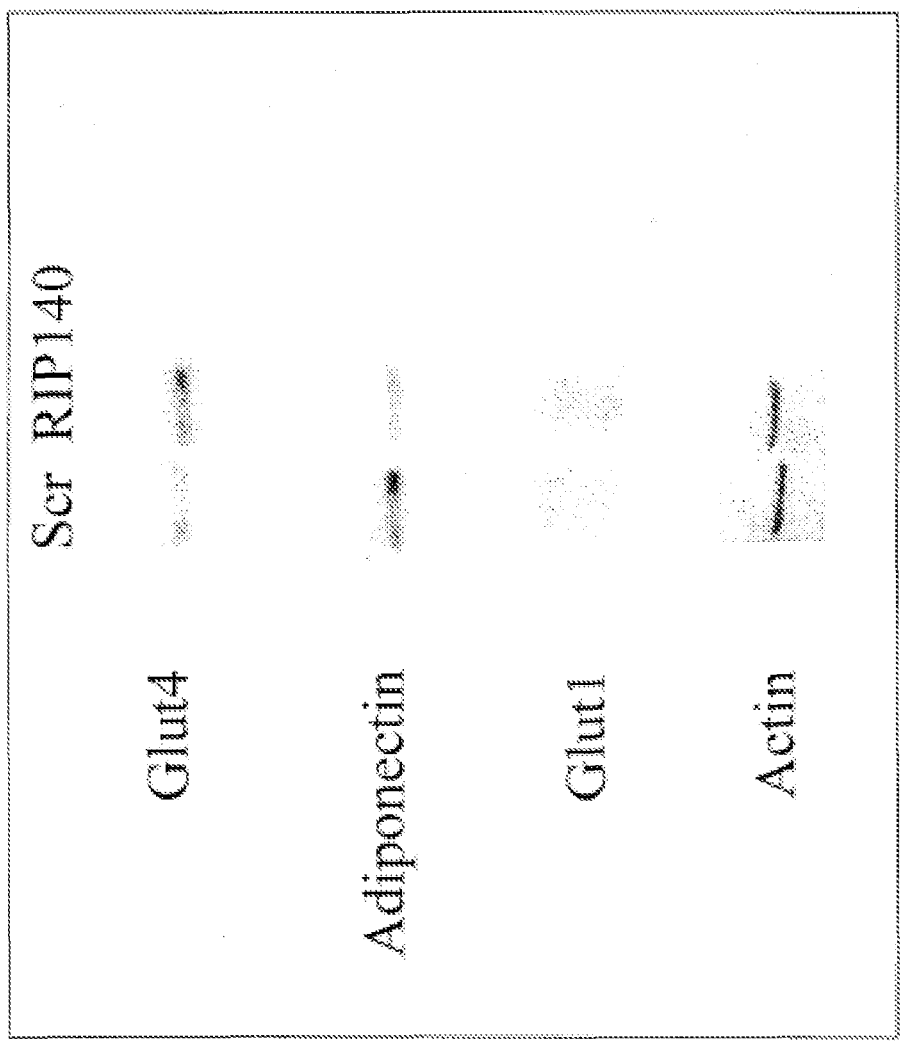
FIG. 6 is a set of photographs of Western blots depicting levels of GLUT4, adiponectin, GLUT1, and actin polypeptides in day 4 3T3-L1 adipocytes transfected with scrambled siRNA (Scr) or RIP140 siRNA. Cell lysates were used for SDS-PAGE to assess Glut4, adiponectin Acrp30 Glut1 and actin expression levels. RIP140 depletion enhances Glut4 expression.
Figure 7:
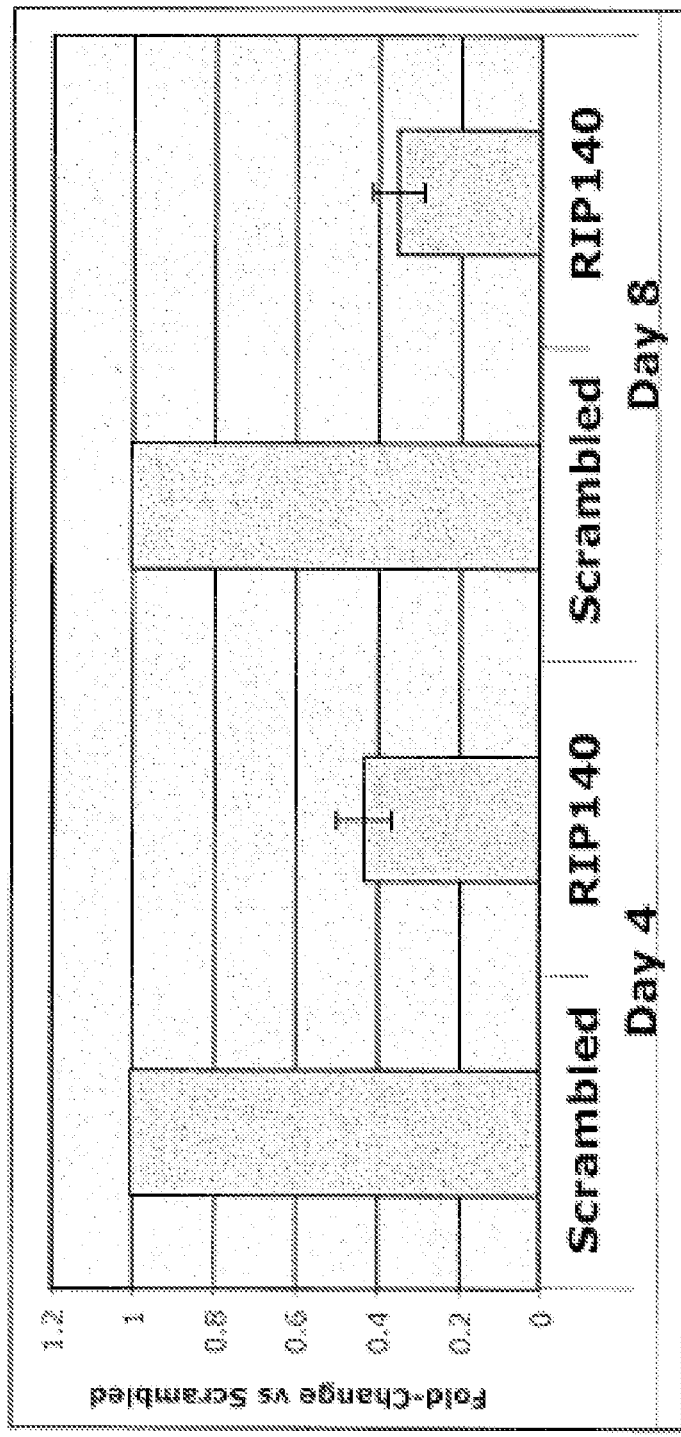
FIG. 7 is a bar graph depicting the results of assays to determine RIP140 depletion in day 4 or day 8 3T3-L1 adipocytes treated with scrambled siRNA or RIP140 siRNA. Day 4 of day 8 3T3-L1 adipocytes were transfected with scrambled siRNA or siRNA against RIP140. Levels were determined by real-time PCR after three days of expression. Depletion of RIP140 mRNA was confirmed by real-time PCR after three days of expression.

The data described in Example 2 show that RIP140 is a negative regulator of glucose uptake in 3T3-L1 cells. The enhanced glucose uptake observed when RIP140 is inhibited could be the result of increased insulin signaling, enhanced GLUT4 expression, or altered GLUT4 trafficking We found that RIP140 depletion significantly enhanced GLTU4 expression (FIG. 6). No change in GLUT1 expression was detected. Interestingly, knock-down of RIP140 decreased adiponectin expression, indicating that the change in GLUT4 expression is the result of a specific regulation by RIP140. RIP140 inhibition had no effect on actin expression. Effective depletion of RIP140 by an individual siRNA was confirmed using real-time PCR of in vitro transcribed message, as no effective antibody is currently available (FIG. 7).

Figure 8:
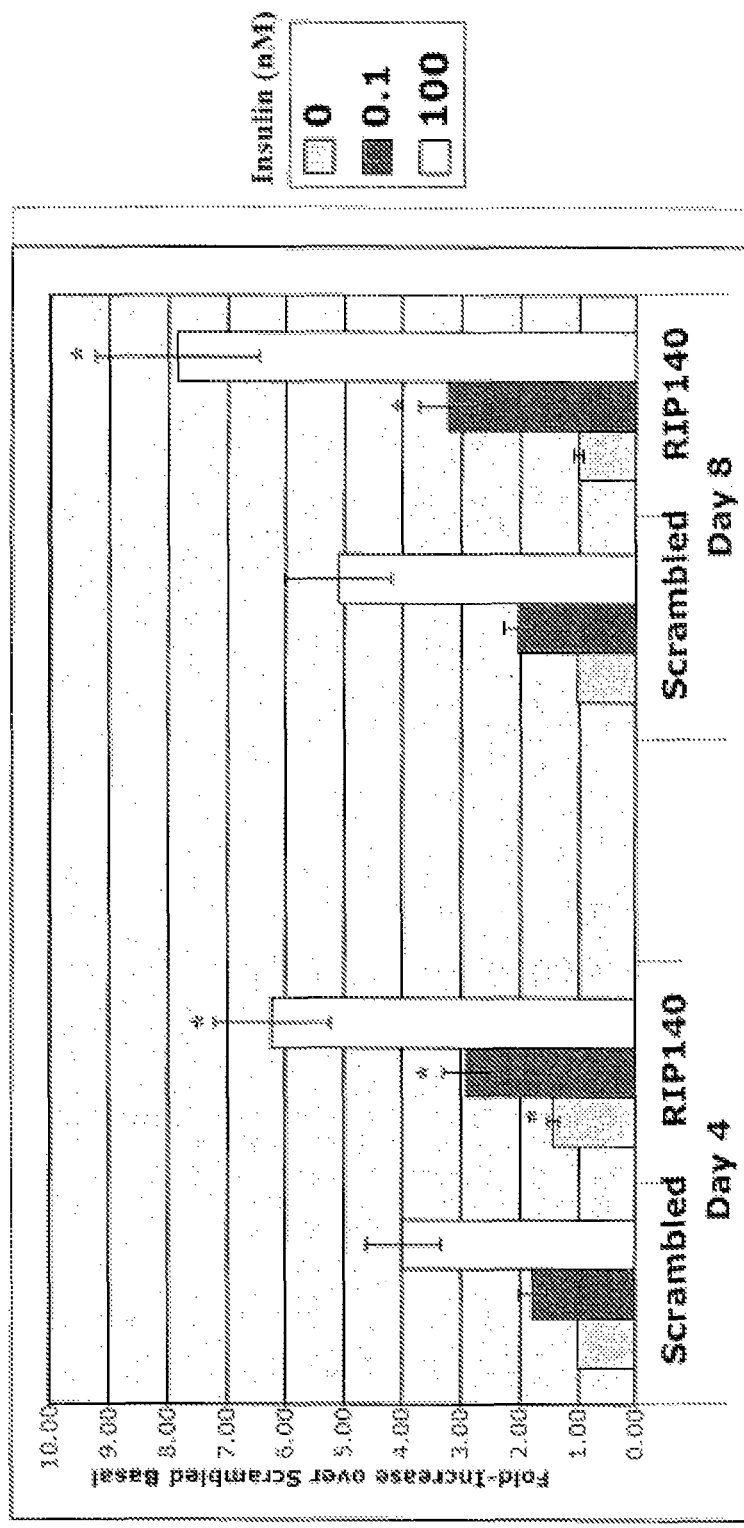
FIG. 8 is a bar graph depicting the results of assays to determine RIP140 regulation of glucose in 3T3-L1 adipocytes transfected with scrambled or RIP140 siRNA after 4 or 8 days of differentiation. The effect of RIP140 depletion on 2-DOG uptake was compared to 3T3-L1 adipocytes transfected with siRNA after 4 or 8 days of differentiation. Levels of 2-deoxyglucose depletion was measured in these assays. The graph shows the average and standard error of five or more independent experiments. *p<0.05 compared to scrambled by student's t-test. RIP140 regulation of glucose uptake is independent of adipogenesis.

We next investigated whether the RIP140 regulation of glucose uptake was dependent upon adipogenesis. As seen in FIG. 7, RIP140 siRNA effectively depletes its mRNA in cells electroporated on day 4 or day 8 post-differentiation. We found that RIP140 depletion effectively enhances glucose uptake in cells electroporated on day 4 or day 8 post-differentiation (FIG. 8). This is important because GLUT4 protein expression in 3T3-L1 cells becomes apparent on day 4 and increases until day 9, when its expression remains steady. Thus the absence of RIP140 is not altering the adipogenic program to change GLUT4 expression, but regulates GLUT4 expression independently of this process.

Example 4

RIP140 Regulation of GLUT4 Expression is Independent of PPARγ

Figure 9A:
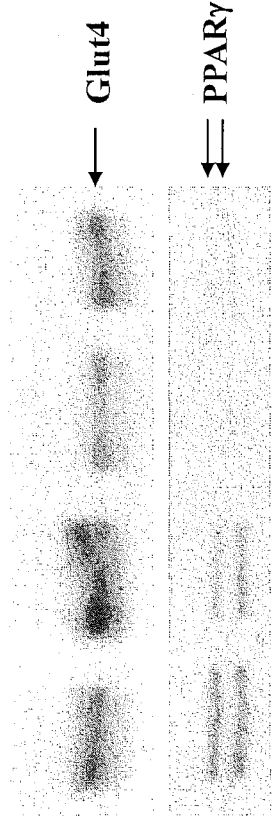
FIG. 9A is a set of photographs of Western blots depicting levels of GLUT4 and PPARγ protein in day 8 3T3-L1 adipocytes transfected with scrambled, RIP140, PPARγ, or RIP140+PPARγ siRNA. Expression was measured 72 hours after transfection.
Figure 9B:
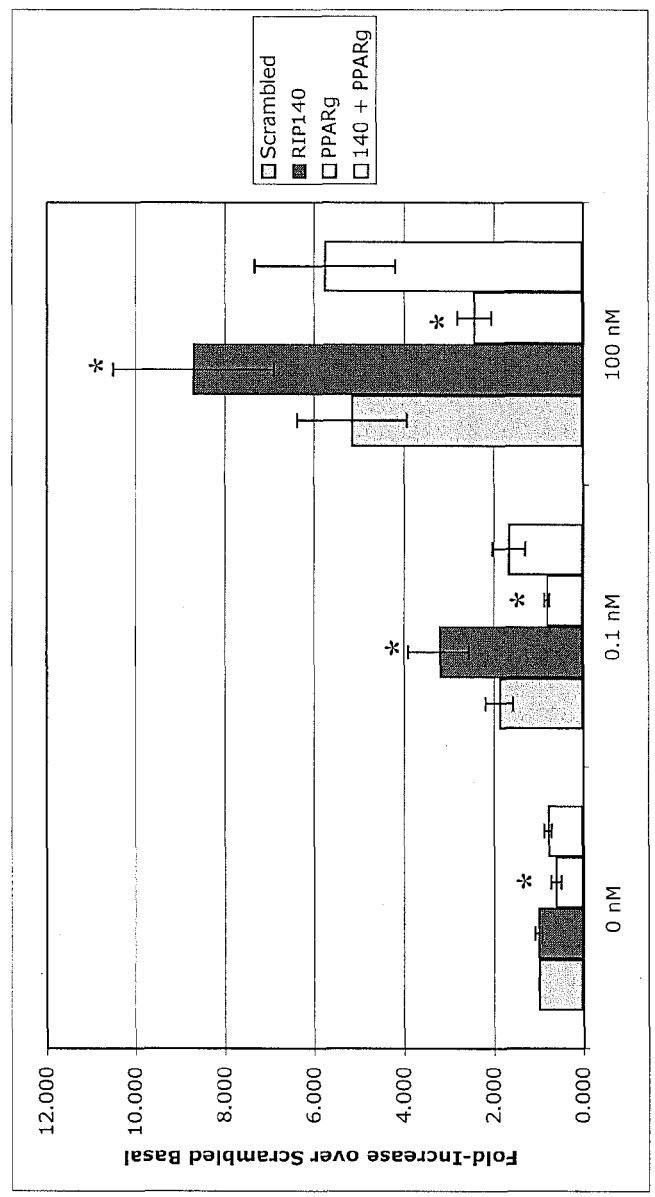
FIG. 9B is a bar graph depicting the results of assays to determine RIP140 regulation of glucose in 3T3-L1 adipocytes transfected with scrambled, RIP140, PPARγ, or RIP140+PPARγ siRNA after 8 days of differentiation. Levels of 2-deoxyglucose depletion was measured in these assays. The graph shows the average and standard error of five independent experiments. *p<0.05 compared to scrambled by student's t-test.

The enhancement in glucose uptake seen with RIP140 depletion is reminiscent of the increased insulin sensitivity and glucose uptake with rosiglitazone treatment, a peroxisome proliferator-activated receptor γ (PPARγ) agonist. To investigate whether RIP140 regulates glucose uptake by modulating PPARγ activity, we used siRNA to deplete RIP140, PPARγ, or RIP140 plus PPARγ. We used day 8 adipocytes to avoid complications resulting from changes in adipogenesis, as PPARγ is an important regulator of this process. Depletion of RIP140 enhanced, while PPARγ depletion inhibited, GLUT4 expression and glucose uptake (FIG. 9). The reduction in GLUT4 expression with PPARγ knockdown was not unexpected as it is required for the maintenance of the adipocyte phenotype (Tamori et al., *Diabetes*, 51(7): 2045-55, 2002). Co-depletion of PPARγ and RIP140 resulted in an enhancement of GLUT4 expression compared to PPARγ depletion alone. This suggests that RIP140 is able to regulate GLUT4 expression and thus glucose uptake in the absence of PPARγ.

Example 5

Effect of RIP140 Depletion on Adipocyte Gene Expression

Figure 10:
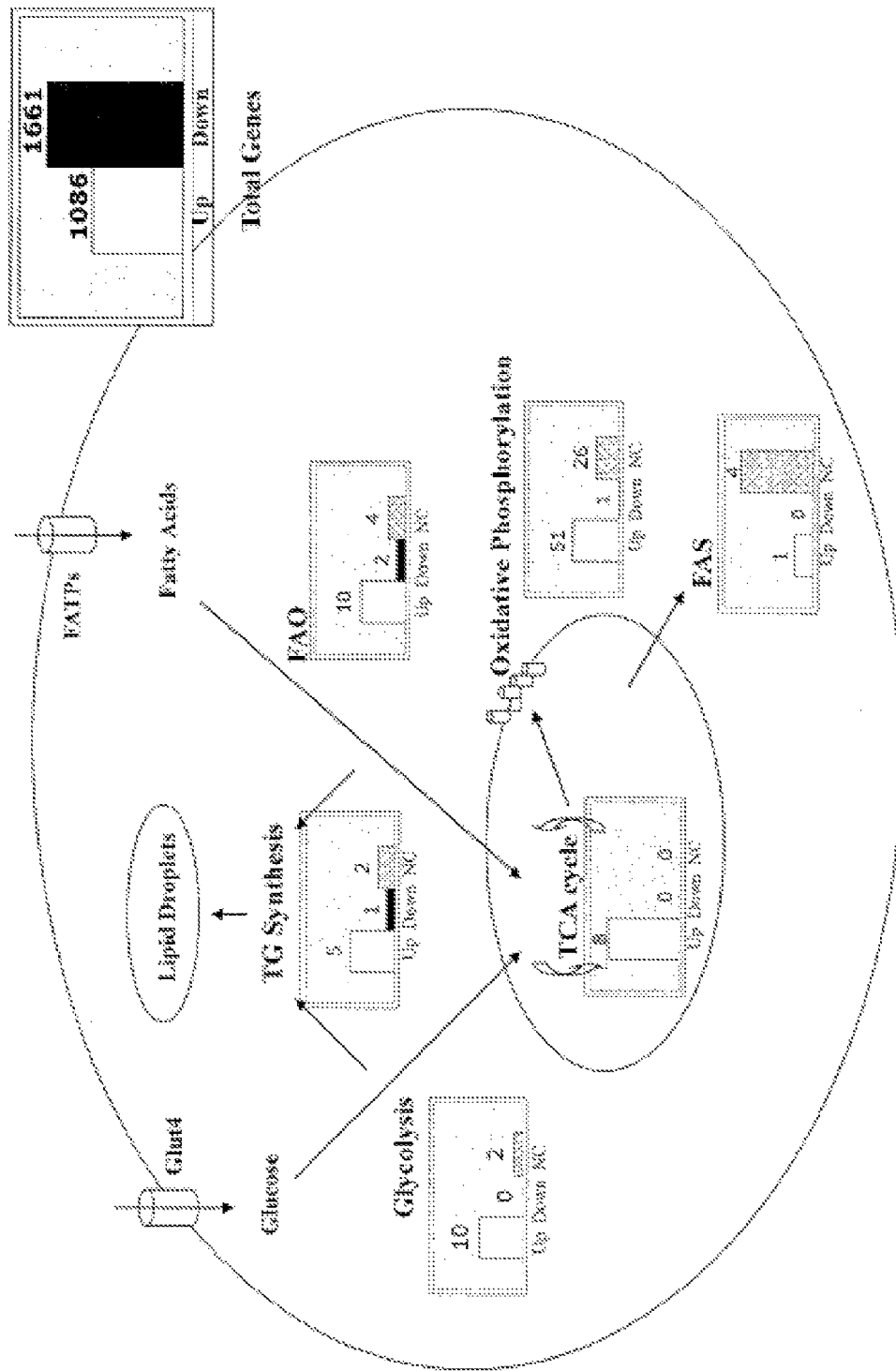
FIG. 10 is a diagram containing graphs of results of assays in which expression profiles of genes involved in glycolysis, fatty acid oxidation (FAO), the TCA cycle, and oxidative phosphorylation were examined by Affymetrix gene chip analysis. Day 8 3T3-L1 adipocytes were transfected with scrambled or RIP 140 siRNA. After 72 hours of expression, mRNA was harvested and used for Affymetrix gene chip analysis. Examination of the expression profiles illustrated that glycolysis, fatty acid oxidation, the TCA cycle, and oxidative phosphorylation genes were u re ulated. RIP140 knock-downenhances multiple metabolic pathways 3T3-L1 adipocytes.

We further analyzed how RIP140 depletion affects adipocyte biology by an analysis of gene expression changes upon RIP140 depletion by Affymetrix gene chip expression profiling. Day 8 3T3-L1 adipocytes were transfected with scrambled or RIP140 siRNA and, after 72 hours of expression, mRNA was harvested and used for Affymetrix gene chip analysis. Day 8 cells were again used to avoid any complications resulting from any alterations in adipogenesis. As shown in FIG. 10, the expression of 2747 genes changes significantly upon depletion of RIP140 (of these, 40% increased and 60% decreased). The changes in gene expression were not distributed randomly, but affected several metabolic pathways, including glycolysis, fatty acid oxidation (FAO), the TCA cycle, and oxidative phosphorylation. The changes in individual gene expression were usually small, on the order of 1.2-1.3 fold, but many genes in each pathway were upregulated. We also found that many mitochondrial genes were upregulated and preliminary data suggests that there may be an increase in the total number of mitochondria in RIP140-depleted cells (data not shown).

Expression of the following genes was increased significantly: C/EBP beta, C/EBP zeta, GA repeat binding protein alpha, LXR beta, EAR2, Nur77, nuclear receptor binding factor 1, nuclear receptor interacting protein 3, PPAR alpha, PPAR binding protein, PPAR gamma, coactivator 1 beta. Expression of the following genes was decreased significantly: C/EBP delta, C/EBP gamma, Rev-ErbA alpha, LXR alpha, COUP/TFII beta, NRIP1 (i.e., RIP140), progesterone receptor membrane component 1, progesterone receptor membrane component 2, and retinoid receptor beta. Modulation of the expression of these genes, or of the activity of polypeptides encoded by these genes, can be used in methods to regulate glucose transport and in methods of identifying agents useful for treatment of disorders related to glucose metabolism (e.g., diabetes, obesity).

The upregulation of mitochondrial genes suggested a change in mitochondrial number and/or function. Several transcription factors and coregulators are thought to be important in regulating mitochondrial biogenesis. These include the nuclear respiratory factors 1 (Nrf1) and 2 (Gabp), the PPARγ coactivator a (PGC-1α) (Kelly and Scarpulla, *Genes Dev.*, 18(4):357-68, 2004), and the nuclear hormone receptors estrogen related receptor (Errα) (Schreiber et al., *Proc Natl Acad Sci USA*, 101(17):6472-7, 2004; Mootha et al., *Proc Natl Acad Sci USA*, 101(17):6570-5, 2004) and thyroid hormone receptor (TR) (Weitzel et al., *Exp. Physiol.*, 88(1):121-8, 2003). Although we did not see a change in the expression of PGC-1α, which has been shown to regulate mitochondrial biogenesis in brown adipose tissue, we did see an increase in the expression of the related PPARγ coactivator PGC-1β and in Errα and Gabpa (FIG. 6). The increases in these transcription factors upon RIP140 depletion may be sufficient to increase the transcription of mitochondrial genes, suggesting that RIP140 is a negative regulator of mitochondrial biogenesis.

Changes in mitochondrial gene expression are also seen in white adipose tissue during adipogenesis (Wilson-Fritch et al., *Mol. Cell. Biol.*, 23(3):1085-94, 2003) and upon the rosiglitazone treatment of ob/ob mice (Wilson-Fritch et al., *J. Clin. Invest.*, 114(9):1281-9, 2004). Adipogenesis and rosiglitazone treatment both enhance insulin sensitivity, as does RIP140 depletion in 3T3-L1 adipocytes.

Example 6

Evaluating RIP140 siRNA Agents in an Animal Model

Agents that inhibit expression or activity of RIP140 in vitro are further tested in vivo in animal models. For example, scrambled siRNA or RIP140 siRNA including SEQ ID NO:1, SEQ ID NO:2, SEQ ID NO:3, and SEQ ID NO:4 are administered to ob/ob mice using hydrodynamic transfection as previously described (McCaffrey, 2002, supra). Ob/ob mice can be obtained from Jackson Laboratories (Strain Name: B6.V-Lep$^{ob}$/J). At various time points after administration of the siRNA, mRNA levels for RIP140 are measured. Additionally, the siRNA can be labeled and tracked using methods known in the art. Levels of glucose, glucose tolerance, and plasma insulin are monitored to determine whether the RIP140 siRNA has a beneficial effect on glucose metabolism, relative to control, i.e., whether the RIP140 siRNA causes a reduction in hyperglycemia or plasma insulin levels.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for increasing glucose transport into an adipocyte cell, the method comprising:
providing an adipocyte cell; and
contacting the adipocyte cell with an oligonucleotide selected from the group consisting of an inhibitory RNA, an antisense oligonucleotide, and a ribozyme, wherein said oligonucleotide inhibits RIP140 mRNA expression in the adipocyte cell, thereby increasing glucose transport into the adipocyte cell.

2. The method of claim 1, wherein the oligonucleotide is an inhibitory RNA.

3. The method of claim 2, wherein the inhibitory RNA is a small inhibitory RNA (siRNA).

4. The method of claim 3, wherein the siRNA comprises a sequence selected from SEQ ID NO: 1, SEQ ID NO: 2, SEQ ID NO: 3, and SEQ ID NO: 4.

5. The method of claim 1, wherein the oligonucleotide is an antisense oligonucleotide.

6. The method of claim 1, wherein the oligonucleotide is a ribozyme.

7. The method of claim 1, wherein the adipocyte cell is contacted in vitro.

8. The method of claim 1, wherein the adipocyte cell is contacted in vivo.

9. The method of claim 1, wherein the oligonucleotide enhances expression of GLUT4 protein in the adipocyte cell.

10. A method for increasing glucose transport into an adipocyte cell in a subject that is at risk for or suffering from a disorder related to glucose metabolism, the method comprising: administering to the subject an oligonucleotide selected from the group consisting of an inhibitory RNA, an antisense oligonucleotide, and a ribozyme, wherein said oligonucleotide inhibits RIP140 mRNA expression in an amount sufficient to increase glucose transport into an adipocyte cell in the subject, thereby increasing glucose transport into an adipocyte cell in the subject.

11. The method of claim 10, wherein the oligonucleotide is an inhibitory RNA.

12. The method of claim 10, wherein the inhibitory RNA is a small inhibitory RNA (siRNA).

13. The method of claim 12, wherein the siRNA comprises a sequence selected from SEQ ID NO: 1, SEQ ID NO: 2, SEQ ID NO: 3, and SEQ ID NO: 4.

14. The method of claim 10, wherein the oligonucleotide is an antisense oligonucleotide.

15. The method of claim 10, wherein the oligonucleotide is a ribozyme.

16. The method of claim 10, wherein the oligonucleotide enhances expression of GLUT4 protein in the adipocyte cell.

17. The method of claim 10, wherein the disorder is type I diabetes.

18. The method of claim 10, wherein the disorder is type II diabetes.

19. The method of claim 10, wherein the disorder is obesity.

* * * * *

SEQUENCE LISTING

```
<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: Primer

<400> SEQUENCE: 1
ggaatgagct cgattataa                                                  19

<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
ggacaaaggt catgagtga                                                  19

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
gaataacgct gccaccttt                                                  19

<210> SEQ ID NO 4
```

-continued

```
<211> LENGTH: 19
<212> TYPE: DNA
<213> ORGANISM: Artificial Sequence
<220> FEATURE:
<223> OTHER INFORMATION: Primer

<400> SEQUENCE: 4
gaaacgcgct caccataaa                                                  19

<210> SEQ ID NO 5
<211> LENGTH: 7292
<212> TYPE: DNA
<213> ORGANISM: Homo sapiens

<400> SEQUENCE: 5
aacactgata tttgcattta atggggaaca aaagatgaag aaggaaaagg aatatattca        60
ctaaggattc tatctgctta ctgctacaga cctatgtgtt aaggaattct tctcctcctc       120
cttgcgtaga agttgatcag cactgtggtc agactgcatt tatcttgtca ttgccagaag       180
aaatcttgga cagaatgtaa cagtacgtct ctctctgatt gcgatggaag gtgataaact       240
gatactcctt tattaaagtt acatcgcact caccacagaa aaccattctt taaagtgaat       300
agaaaccaag cccttgtgaa cacttctatt gaacatgact catggagaag agcttggctc       360
tgatgtgcac caggattcta ttgtttttaac ttacctagaa ggattactaa tgcatcaggc      420
agcaggggga tcaggtactg ccgttgacaa aaagtctgct gggcataatg aagaggatca       480
gaactttaac atttctggca gtgcatttcc cacctgtcaa agtaatggtc cagttctcaa       540
tacacataca tatcagggt ctggcatgct gcacctcaaa aaagccagac tgttgcagtc        600
ttctgaggac tggaatgcag caaagcggaa gaggctgtct gattctatca tgaatttaaa       660
cgtaaagaag gaagctttgc tagctggcat ggttgacagt gtgcctaaag gcaaacagga       720
tagcacatta ctggcctctt tgcttcagtc attcagctct aggctgcaga ctgttgctct       780
gtcacaacaa atcaggcaga gcctcaagga gcaaggatat gccctcagtc atgattcttt       840
aaaagtggag aaggatttaa ggtgctatgg tgttgcatca agtcacttaa aaactttgtt       900
gaagaaaagt aaagttaaag atcaaaagcc tgatacgaat cttcctgatg tgactaaaaa       960
cctcatcaga gataggtttg cagagtctcc tcatcatgtt ggacaaagtg aacaaaggt      1020 catgagtgaa ccgttgtcat gtgctgcaag attacaggct gttgcaagca tggtggaaaa      1080
aagggctagt cctgccacct cacctaaacc tagtgttgct tgtagccagt tagcattact      1140
tctgtcaagc gaagcccatt tgcagcgta ttctcgagaa cacgctttaa aaacgcaaaa       1200
tgcaaatcaa gcagcaagtg aaagacttgc tgctatggcc agattgcaag aaaatggcca      1260
gaaggatgtt ggcagttacc agctcccaaa aggaatgtca agccatctta atggtcaggc      1320
aagaacatca tcaagcaaac tgatggctag caaaagtagt gctacagtgt ttcaaaatcc      1380
aatgggtatc attccttctt cccctaaaaa tgcaggttat aagaactcac tggaaagaaa      1440
caatataaaa caagctgcta caatagtttt gcttttacat cttcttaaaa gccagactat      1500
acctaagcca atgaatggac acagtcacag tgagagagga agcattttg aggaaagtag       1560 tacacctaca actattgatg aatattcaga taacaatcct agttttacag atgacagcag      1620
tggtgatgaa agttccttatt ccaactgtgt tcccatagac ttgtcttgca acaccgaac      1680 tgaaaaatca gaatctgacc aacctgtttc cctggataac ttcactcaat ccttgctaaa      1740
cacttgggat ccaaaagtcc cagatgtaga tatcaaagaa gatcaagata cctcaaagaa      1800
ttctaagcta aactcacacc agaaagtaac acttcttcaa ttgctacttg gccataagaa      1860
```

```
tgaagaaaat gtagaaaaaa acaccagccc tcagggagta cacaatgatg tgagcaagtt    1920
caatacacaa aattatgcaa ggacttctgt gatagaaagc cccagtacaa atcggactac    1980
tccagtgagc actccacctt tacttacatc aagcaaagca gggtctccca tcaatctctc    2040
tcaacactct ctggtcatca aatggaattc cccaccatat gtctgcagta ctcagtctga    2100
aaagctaaca aatactgcat ctaaccactc aatggacctt acaaaaagca aagacccacc    2160
aggagagaaa ccagcccaaa atgaaggtgc acagaactct gcaacgttta gtgccagtaa    2220
gctgttacaa aatttagcac aatgtggaat gcagtcatcc atgtcagtgg aagagcagag    2280
acccagcaaa cagctgttaa ctggaaacac agataaaccg ataggtatga ttgatagatt    2340
aaatagccct ttgctctcaa ataaaacaaa tgcagttgaa gaaaataaag catttagtag    2400
tcaaccaaca ggtcctgaac cagggctttc tggttctgaa atagaaaatc tgcttgaaag    2460
acgtactgtc ctccagttgc tcctggggaa ccccaacaaa gggaagagtg aaaaaaaaga    2520
gaaaactccc ttaagagatg aaagtactca ggaacactca gagagagctt taagtgaaca    2580
aatactgatg gtgaaaataa aatctgagcc ttgtgatgac ttacaaattc ctaacacaaa    2640
tgtgcacttg agccatgatg ctaagagtgc cccattcttg ggtatggctc ctgctgtgca    2700
gagaagcgca cctgccttac cagtgtccga agactttaaa tcggagcctg tttcacctca    2760 ggattttttct ttctccaaga atggtctgct aagtcgattg ctaagacaaa atcaagatag    2820
ttacctggca gatgattcag acaggagtca cagaaataat gaaatggcac ttctagaatc    2880
aaagaatctt tgcatggtcc ctaagaaaag gaagctttat actgagccat agaaaatcc    2940 atttaaaaag atgaaaaaca acattgttga tgctgcaaac aatcacagtg ccccagaagt    3000
actgtatggg tccttgctta accaggaaga gctgaaattt agcagaaatg atcttgaatt    3060
taaatatcct gctggtcatg gctcagccag cgaaagtgaa cacaggagtt gggccagaga    3120
gagcaaaagc tttaatgttc tgaaacagct gcttctctca gaaaactgtg tgcgagattt    3180
gtccccgcac agaagtaact ctgtggctga cagtaaaaag aaaggacaca aaaataatgt    3240
gaccaacagc aaacctgaat ttagcatttc ttctttaaat ggactgatgt acagttccac    3300
tcagcccagc agttgcatgg ataacaggac atttttcatac ccaggtgtag taaaaactcc    3360
tgtgagtcct actttccctg agcacttggg ctgtgcaggg tctagaccag aatctgggct    3420
tttgaatggg tgttccatgc ccagtgagaa aggacccatt aagtgggtta tcactgatgc    3480
ggagaagaat gagtatgaaa aagactctcc aagattgacc aaaaccaacc caatactata    3540
ttacatgctt caaaaggag gcaattctgt taccagtcga gaaacacaag acaaggacat    3600
ttggagggag gcttcatctg ctgaaagtgt ctcacaggtc acagccaaag aagagttact    3660
tcctactgca gaaacgaaag cttctttctt taatttaaga agcccttaca atagccatat    3720
gggaaataat gcttctcgcc cacacagcgc aaatggagaa gtttatggac ttctgggaag    3780
cgtgctaacg ataaagaaag aatcagaata aaatgtacct gccatccagt tttgatctt    3840 tttaaaacta atgagtatga acttgagatc tgtataaata agagcatgat ttgaaaaaaa    3900
gcatggtata attgaaactt ttttcatttt gaaaagtatt ggttactggt gatgttgaaa    3960
tatgcatact aattttttgct taacattaga tgtcatgagg aaactactga actagcaatt    4020
ggttgtttaa cacttctgta tgcatcagat aacaactgtg agtagcctat gaatgaaatt    4080 ctttttataaa tattaggcat aaattaaaat gtaaaactcc attcatagtg gattaatgca    4140
ttttgctgcc tttattaggg tactttattt tgcttttcag aagtcagcct acataacaca    4200
tttttaaagt ctaaactgtt aaacaactct ttaaggata attatccaat aaaaaaaaac    4260
```

```
ctagtgctga ttcacagctt attatccaat tcaaaaataa attagaaaaa tatatgctta   4320 cattttcac ttttgctaaa aagaaaaaaa aaggtgttt atttttaact cttggaagag     4380
gttttgtggt tcccaatgtg tctgtcccac cctgatcctt ttcaatatat atttctttaa   4440
accttgtgct acttagtaaa aattgattac aattgaggga agtttgatag atcctttaaa   4500
aaaaaggcag atttccattt tttgtatttt aactacttta ctaaattaat actcctcctt   4560
ttacagaatt agaaaagtta acatttatct ttaggtggtt tcctgaaaag ttgaatattt   4620
aagaaattgt ttttaacaga agcaaaatgg cttttctttg acagttttc accatctctt    4680 gtaaaagtta attctcacca ttcctgtggt acctgcgagt gttatgacca ggattcctta   4740
aacctgaact cagaccactt gcattagaac catctggagc acttgtttta aaatgcagat   4800
tcataggcag catctcagat ctacagaaca agaatctctg ctaagtggac ctggaatctt   4860
ccatctgcat cttaacatgc tctctaggtg tttcttgtgt ttgagaacca tgacttatga   4920
ctttcctcag aacatgagac tgtaaaacaa aaacaaaaaa ctatgtgatg cctctatttt   4980
ccccaataca gtcacacatc agctcaaaat ttgcaatatt gtagttcata tattaccgtt   5040
atgtctttgg aaatcgggtt cagaacactt tttatgacaa aaattgggtg gaggggataa   5100
ctttcatatc tggctcaaca tctcaggaaa atctgtgatt atttgtgtgt tctaatgagt   5160
aacatctact tagttagcct tagggatgga aaaacagggc cacttaccaa actcaggtga   5220
ttccaggatg gtttggaaac ttctcctgaa tgcatcctta acctttatta aaaccattgt   5280
cctaagaaca atgccaacaa agcttacaac atttagttta aacccaagaa gggcactaaa   5340
ctcagattga ctaaataaaa agtacaaagg gcacatatac gtgacagaat tgtacacaat   5400
cactccattg gatcttttac tttaaagtag tgatgaaaag tacatgttga tactgtctta   5460
gaagaaatta atatattagt gaagccacat ggggtttcag ttgcgaaaca ggtctgtttt   5520
tatgttcagt ttgtacaatc cacaattcat tcaccagata ttttgttctt aattgtgaac   5580
caggttagca aatgacctat caaaaattat tctataatca ctactagtta ggatattgat   5640
ttaaaattgt tctacttgaa gtggtttcta agatttttat attaaaaata ggtgtgattt   5700 cctaatgatga tctaaaaccc taaatggtta ttttcctca gaatgatttg taaatagcta   5760
ctggaaatat tatacagtaa taggagtggg tattatgcaa catcatggag aagtgaaggc   5820
ataggcttat tctgacataa aattccactg gccagttgaa tatattctat tccatgtcca   5880
tactatgaca atcttattgt caacactata taaataagct tttaaacaag tcattttct    5940 tgatcgttgt ggaaggtttg gagccttaga ggtatgtcag aaaaaatatg ttggtattct   6000
cccttgggta gggggaaatg acctttttac aagagagtga atttaggtc agggaaaaga    6060 ccaagggcca gcattgctac ttttgtgtgt gtgtgtgtgg gttttgtttt gttttttgg    6120 ttggctggtt gttttcgttg ttgttaacaa aggaatgaga atatgtaata cttaaataaa   6180
catgaccacg aagaatgctg ttctgattta ctagagaatg ttcccaattt gaatttaggg   6240
tgattttaaa gaacagtgag aaagggcata catccacaga ttcactttgt ttatgcatat   6300
gtagatacaa ggatgcacat atacacattt tcaaggacta ttttagatat ctagacaatt   6360
tcttctaata aagtcatttg tgaaagggta ctacagctta ttgacatcag taaggtagca   6420
ttcattacct gtttattctc tgctgcatct tacagaagag taaactggtg agagtatata   6480
ttttatatat atatatatat atatatatat aatatgtata tatatatata ttgacttgtt   6540
acatgaagat gttaaaatcg gttttaaag gtgatgtaaa tagtgatttc cttaatgaaa    6600
aatacatatt ttgtattgtt ctaatgcaac agaaaagcct tttaatctct ttggttcctg   6660
```

```
tatattccat gtataagtgt aaatataatc agacaggttt aaaagttgtg catgtatgta   6720
tacagttgca agtctggaca aatgtataga ataaaccttt tatttaagtt gtgattacct   6780
gctgcatgaa aagtgcatgg gggaccctgt gcatctgtgc atttggcaaa atgtcttaac   6840
aaatcagatc agatgttcat cctaacatga cagtattcca tttctggaca tgacgtctgt   6900
ggtttaagct ttgtgaaaga atgtgctttg attcgaaggg tcttaaagaa ttttttttaat  6960 cgtcaaccac ttttaaacat aaagaattca cacaactact ttcatgaatt ttttaatccc   7020
attgcaaaca ttattccaag agtatcccag tattagcaat actggaatat aggcacatta   7080
ccattcatag taagaattct ggtgtttaca caaccaaatt tgatgcgatc tgctcagtaa   7140
tataatttgc cattttatt agaaatttaa tttcttcatg tgatgtcatg aaactgtaca    7200
tactgcagtg tgaattttt tgttttgttt tttaatcttt tagtgtttac ttcctgcagt    7260
gaatttgaat aaatgagaaa aaatgcattg tc                                 7292
```

<210> SEQ ID NO 6
<211> LENGTH: 1158
<212> TYPE: PRT
<213> ORGANISM: Homo sapiens

<400> SEQUENCE: 6

```
Met Thr His Gly Glu Glu Leu Gly Ser Asp Val His Gln Asp Ser Ile
 1               5                  10                  15

Val Leu Thr Tyr Leu Glu Gly Leu Leu Met His Gln Ala Ala Gly Gly
            20                  25                  30

Ser Gly Thr Ala Val Asp Lys Lys Ser Ala Gly His Asn Glu Glu Asp
        35                  40                  45

Gln Asn Phe Asn Ile Ser Gly Ser Ala Phe Pro Thr Cys Gln Ser Asn
    50                  55                  60

Gly Pro Val Leu Asn Thr His Thr Tyr Gln Gly Ser Gly Met Leu His
65                  70                  75                  80

Leu Lys Lys Ala Arg Leu Leu Gln Ser Ser Glu Asp Trp Asn Ala Ala
                85                  90                  95

Lys Arg Lys Arg Leu Ser Asp Ser Ile Met Asn Leu Asn Val Lys Lys
            100                 105                 110

Glu Ala Leu Leu Ala Gly Met Val Asp Ser Val Pro Lys Gly Lys Gln
        115                 120                 125

Asp Ser Thr Leu Leu Ala Ser Leu Leu Gln Ser Phe Ser Ser Arg Leu
    130                 135                 140

Gln Thr Val Ala Leu Ser Gln Gln Ile Arg Gln Ser Leu Lys Glu Gln
145                 150                 155                 160

Gly Tyr Ala Leu Ser His Asp Ser Leu Lys Val Glu Lys Asp Leu Arg
                165                 170                 175

Cys Tyr Gly Val Ala Ser Ser His Leu Lys Thr Leu Leu Lys Lys Ser
            180                 185                 190

Lys Val Lys Asp Gln Lys Pro Asp Thr Asn Leu Pro Asp Val Thr Lys
        195                 200                 205

Asn Leu Ile Arg Asp Arg Phe Ala Glu Ser Pro His His Val Gly Gln
    210                 215                 220

Ser Gly Thr Lys Val Met Ser Glu Pro Leu Ser Cys Ala Ala Arg Leu
225                 230                 235                 240

Gln Ala Val Ala Ser Met Val Glu Lys Arg Ala Ser Pro Ala Thr Ser
                245                 250                 255

Pro Lys Pro Ser Val Ala Cys Ser Gln Leu Ala Leu Leu Leu Ser Ser
            260                 265                 270
```

```
Glu Ala His Leu Gln Gln Tyr Ser Arg Glu His Ala Leu Lys Thr Gln
                275                 280                 285

Asn Ala Asn Gln Ala Ala Ser Glu Arg Leu Ala Ala Met Ala Arg Leu
        290                 295                 300

Gln Glu Asn Gly Gln Lys Asp Val Gly Ser Tyr Gln Leu Pro Lys Gly
305                 310                 315                 320

Met Ser Ser His Leu Asn Gly Gln Ala Arg Thr Ser Ser Ser Lys Leu
                325                 330                 335

Met Ala Ser Lys Ser Ser Ala Thr Val Phe Gln Asn Pro Met Gly Ile
            340                 345                 350

Ile Pro Ser Ser Pro Lys Asn Ala Gly Tyr Lys Asn Ser Leu Glu Arg
            355                 360                 365

Asn Asn Ile Lys Gln Ala Ala Asn Asn Ser Leu Leu Leu His Leu Leu
            370                 375                 380

Lys Ser Gln Thr Ile Pro Lys Pro Met Asn Gly His Ser His Ser Glu
385                 390                 395                 400

Arg Gly Ser Ile Phe Glu Glu Ser Ser Thr Pro Thr Ile Asp Glu
                405                 410                 415

Tyr Ser Asp Asn Asn Pro Ser Phe Thr Asp Asp Ser Ser Gly Asp Glu
                420                 425                 430

Ser Ser Tyr Ser Asn Cys Val Pro Ile Asp Leu Ser Cys Lys His Arg
            435                 440                 445

Thr Glu Lys Ser Glu Ser Asp Gln Pro Val Ser Leu Asp Asn Phe Thr
            450                 455                 460

Gln Ser Leu Leu Asn Thr Trp Asp Pro Lys Val Pro Asp Val Asp Ile
465                 470                 475                 480

Lys Glu Asp Gln Asp Thr Ser Lys Asn Ser Lys Leu Asn Ser His Gln
                485                 490                 495

Lys Val Thr Leu Leu Gln Leu Leu Gly His Lys Asn Glu Glu Asn
            500                 505                 510

Val Glu Lys Asn Thr Ser Pro Gln Gly Val His Asn Asp Val Ser Lys
            515                 520                 525

Phe Asn Thr Gln Asn Tyr Ala Arg Thr Ser Val Ile Glu Ser Pro Ser
            530                 535                 540

Thr Asn Arg Thr Thr Pro Val Ser Thr Pro Pro Leu Leu Thr Ser Ser
545                 550                 555                 560

Lys Ala Gly Ser Pro Ile Asn Leu Ser Gln His Ser Leu Val Ile Lys
                565                 570                 575

Trp Asn Ser Pro Pro Tyr Val Cys Ser Thr Gln Ser Glu Lys Leu Thr
            580                 585                 590

Asn Thr Ala Ser Asn His Ser Met Asp Leu Thr Lys Ser Lys Asp Pro
            595                 600                 605

Pro Gly Glu Lys Pro Ala Gln Asn Glu Gly Ala Gln Asn Ser Ala Thr
610                 615                 620

Phe Ser Ala Ser Lys Leu Leu Gln Asn Leu Ala Gln Cys Gly Met Gln
625                 630                 635                 640

Ser Ser Met Ser Val Glu Glu Gln Arg Pro Ser Lys Gln Leu Leu Thr
                645                 650                 655

Gly Asn Thr Asp Lys Pro Ile Gly Met Ile Asp Arg Leu Asn Ser Pro
                660                 665                 670

Leu Leu Ser Asn Lys Thr Asn Ala Val Glu Glu Asn Lys Ala Phe Ser
            675                 680                 685

Ser Gln Pro Thr Gly Pro Glu Pro Gly Leu Ser Gly Ser Glu Ile Glu
```

690                 695                 700
Asn Leu Leu Glu Arg Arg Thr Val Leu Gln Leu Leu Gly Asn Pro
705                 710                 715                 720

Asn Lys Gly Lys Ser Glu Lys Lys Glu Lys Thr Pro Leu Arg Asp Glu
                725                 730                 735

Ser Thr Gln Glu His Ser Glu Arg Ala Leu Ser Glu Gln Ile Leu Met
                740                 745                 750

Val Lys Ile Lys Ser Glu Pro Cys Asp Asp Leu Gln Ile Pro Asn Thr
                755                 760                 765

Asn Val His Leu Ser His Asp Ala Lys Ser Ala Pro Phe Leu Gly Met
770                 775                 780

Ala Pro Ala Val Gln Arg Ser Ala Pro Ala Leu Pro Val Ser Glu Asp
785                 790                 795                 800

Phe Lys Ser Glu Pro Val Ser Pro Gln Asp Phe Ser Phe Ser Lys Asn
                805                 810                 815

Gly Leu Leu Ser Arg Leu Leu Arg Gln Asn Gln Asp Ser Tyr Leu Ala
                820                 825                 830

Asp Asp Ser Asp Arg Ser His Arg Asn Asn Glu Met Ala Leu Leu Glu
                835                 840                 845

Ser Lys Asn Leu Cys Met Val Pro Lys Lys Arg Lys Leu Tyr Thr Glu
850                 855                 860

Pro Leu Glu Asn Pro Phe Lys Lys Met Lys Asn Asn Ile Val Asp Ala
865                 870                 875                 880

Ala Asn Asn His Ser Ala Pro Glu Val Leu Tyr Gly Ser Leu Leu Asn
                885                 890                 895

Gln Glu Glu Leu Lys Phe Ser Arg Asn Asp Leu Glu Phe Lys Tyr Pro
                900                 905                 910

Ala Gly His Gly Ser Ala Ser Glu Ser His Arg Ser Trp Ala Arg
                915                 920                 925

Glu Ser Lys Ser Phe Asn Val Leu Lys Gln Leu Leu Leu Ser Glu Asn
                930                 935                 940

Cys Val Arg Asp Leu Ser Pro His Arg Ser Asn Ser Val Ala Asp Ser
945                 950                 955                 960

Lys Lys Lys Gly His Lys Asn Asn Val Thr Asn Ser Lys Pro Glu Phe
                965                 970                 975

Ser Ile Ser Ser Leu Asn Gly Leu Met Tyr Ser Ser Thr Gln Pro Ser
                980                 985                 990

Ser Cys Met Asp Asn Arg Thr Phe Ser Tyr Pro Gly Val Val Lys Thr
                995                 1000                1005

Pro Val Ser Pro Thr Phe Pro Glu His Leu Gly Cys Ala Gly Ser Arg
    1010                1015                1020

Pro Glu Ser Gly Leu Leu Asn Gly Cys Ser Met Pro Ser Glu Lys Gly
1025                1030                1035                1040

Pro Ile Lys Trp Val Ile Thr Asp Ala Glu Lys Asn Glu Tyr Glu Lys
                1045                1050                1055

Asp Ser Pro Arg Leu Thr Lys Thr Asn Pro Ile Leu Tyr Tyr Met Leu
                1060                1065                1070

Gln Lys Gly Gly Asn Ser Val Thr Ser Arg Glu Thr Gln Asp Lys Asp
                1075                1080                1085

Ile Trp Arg Glu Ala Ser Ser Ala Glu Ser Val Ser Gln Val Thr Ala
                1090                1095                1100

Lys Glu Glu Leu Leu Pro Thr Ala Glu Thr Lys Ala Ser Phe Phe Asn
1105                1110                1115                1120

```
Leu Arg Ser Pro Tyr Asn Ser His Met Gly Asn Asn Ala Ser Arg Pro
        1125                1130                1135

His Ser Ala Asn Gly Glu Val Tyr Gly Leu Leu Gly Ser Val Leu Thr
        1140                1145                1150

Ile Lys Lys Glu Ser Glu
        1155

<210> SEQ ID NO 7
<211> LENGTH: 4531
<212> TYPE: DNA
<213> ORGANISM: Mus musculus

<400> SEQUENCE: 7
```

| | | | | | |
|---|---|---|---|---|---|
| gagacattgc | agcagagccc | cgaactcggg | aggcgacggc | gaccgcggcg | caggcggagg | 60 |
| acgagccggc | cccagcccgc | ccgagcgcag | cgcccgtggc | ctcgcgcggc | cgcagggcac | 120 |
| ggctaacctg | gaaggaggg | agcgacgcgg | atcggcggcc | cggagccgcg | gcggcctcga | 180 |
| aggcgtggac | tgtgagcggt | tgcagagctg | ttctcaggac | ataatccttt | aacattcggg | 240 |
| aggaacacat | ccaggaggtg | cgcagttgac | tgaggaggcc | cggagaatct | gaagactccg | 300 |
| atgacatcag | agttgctttt | caacagcctt | ctcagcttcc | tttcccacat | agcagaggct | 360 |
| caggctgagg | cagacgatac | tgacgtgcgt | ttggtgagca | cgaaagatg | atgaagaaag | 420 |
| aaaaccagca | tattccctga | cctgggtg | ccagcgctgc | cgctgtgcta | aggaagttgc | 480 |
| gaggctggcc | cttgcctagc | cactcatcag | tgctgtagtc | tgcacccgag | tttgccccag | 540 |
| cctctgagcc | cctcgtcact | gcctgaagat | ccctggtca | gaatgttaac | agtgcatctc | 600 |
| tgcccgactg | ctatgggagg | tgatcaggtg | acgctcactt | cctgacgtca | cgtgggatct | 660 |
| tactgacgag | aggagctctt | tcacgtgaac | ggaagccgag | cccctgtgag | cgcttgtatt | 720 |
| gaacatgact | catggagaag | agcttggctc | tgatgtgcat | caggattcta | ttgtcttaac | 780 |
| ttacctcgaa | gggttactaa | tgcatcaggc | agcaggggga | tcaggcactg | ccattaacaa | 840 |
| aaagtctgct | ggccacaaag | aggaagacca | gaactttaac | ctctcgggca | gtgcgtttcc | 900 |
| ctcctgtcaa | agcaatggtc | ccactgtcag | tacccagacg | taccagggat | ctggcatgct | 960 |
| gcacctcaaa | aaagccagac | tgctgcagtc | ttccgaggac | tggaacgcgg | caaagcggaa | 1020 |
| gaggctgtct | gattccatcg | tgaatttaaa | cgtaaagaag | gaagcgttgc | tggctggcat | 1080 |
| ggttgacagt | gtgcctaaag | gcaaacagga | tagcacattg | ctggcctctt | tgcttcagtc | 1140 |
| attcagctct | aggctgcaga | ctgttgctct | gtcacagcag | attagacaga | gcctcaagga | 1200 |
| gcagggatat | gccctcagtc | acgagtcttt | aaaagtggag | aaggatttaa | ggtgctatgg | 1260 |
| cgtggcctca | agtcacttaa | aaactctgtt | gaagaaaagt | aaaaccaagg | atcaaaagtc | 1320 |
| aggtcccacc | ctccctgacg | tgactccaaa | ccttatcaga | gatagctttg | ttgagtcatc | 1380 |
| ccatcccgca | gtgggacaaa | gtgggacaaa | ggtcatgagt | gagcccttgt | catgtgctgc | 1440 |
| aagattacag | gctgttgcca | gcatggtgga | gaaaagggcg | agtcccgctg | cctccccaaa | 1500 |
| gcctagtgtt | gcctgcagcc | agttggcgct | gctcctgtcc | agcgaggccc | acctgcagca | 1560 |
| gtactctcgg | gaacatgctc | taaaaacgca | gaacgcacat | caggtggcaa | gcgaaagact | 1620 |
| tgcagccatg | gccagattgc | aagagaatgg | gcagaaggac | gtgggcagtt | cgcagctctc | 1680 |
| caaaggggtg | tctggccatc | tcaacgggca | ggccagagca | ctgccggcaa | gcaaactggt | 1740 |
| ggccaacaag | aataacgctg | ccaccttca | gagtccaatg | ggtgttgtcc | cttcctcccc | 1800 |
| caaaacacg | agctataaga | actcactgga | agaaacaac | ctaaagcagg | ctgctaataa | 1860 |
| cagtctgctt | ttgcatctcc | tcaaaagcca | gaccataccc | acgccgatga | acgggcacag | 1920 |

```
ccagaacgag agagcgagca gttttgagag tagcacgccc accacgattg atgagtactc    1980
cgataacaac ccgagcttta cagatgacag cagtggagac gaaagctcgt actccaattg    2040
cgttcccata gacctgtctt gcaaacaccg gatcgaaaag ccggaagctg agcggcccgt    2100
ttcgctggag aacctaaccc agtccttgtt aaacacgtgg gatcccaaga tccccggcgt    2160
tgacatcaaa gaagatcaag ataccctcaac aaattccaag ctgaattcac accagaaagt    2220
cactcttctt cagttgctgc tcggccataa aagtgaagaa actgttgaaa ggaacgccag    2280
ccctcaggac atccatagtg atgggactaa gttcagtcct cagaattaca caaggacttc    2340
tgtcatcgaa agccccagta ccaacaggac taccccagtg agcactccac cactgtatac    2400
agccagccaa gcagagtctc ccatcaatct ttcccagcac tctctggtca tcaagtggaa    2460
ttccccgccg tatgcctgca gtactcccgc ttccaagctc acgaacaccg cgcctagcca    2520
cctgatggac ctcacgaaag gcaaagagtc ccaagccgag aaaccagccc cgagtgaagg    2580
tgcacaaaat tccgccacgt tcagtgccag taaactgtta caaaatttgg ctcagtgcgg    2640
attgcagtct tccgggccag gggaagagca gagaccctgc aaacagctgt aagtggaaa     2700
cccagacaaa cctctcggtc tgattgatag attaaacagc cctctgctct caaataaaac    2760
caatgcggct gaagagagca aagccttcag cagtcagcct gccgggcctg agccgggact    2820
tcctggttgt gagatagaaa atctcttgga aagacggact gtccttcagt tgctcctggg    2880
aaattccagc aaagggaaga atgagaagaa agagaaaacc cccgcacgag acgaggctcc    2940
tcaggagcat tcgagagggg ctgcaaatga acagatactc atggtgaaga ttaaatccga    3000
gccttgtgac gacttccaga cccacaacac aaacctgccc ttaaaccacg atgccaagag    3060
cgccccttc ttaggtgtga ctcccgccat ccacaggagc acagcggcct taccagtgtc    3120
ggaggacttt aaatccgagc ctgcttcacc tcaggatttc tctttctcaa agaacgggct    3180
gttgagtcgc ttgctgagac agaatcaaga gagttacccg gcagatgagc aggacaagag    3240
tcacagaaac agtgagctgc caaccctgga gtcgaagaac atctgcatgg tcccgaagaa    3300
aaggaagctg tatacggaac cactggagaa tccatttaaa aagatgaaaa atactgccgt    3360
agatactgcc aatcatcaca gcggcccgga agtactctac gggtcgttgc ttcatcagga    3420
agagctgaag tttagcagga atgagctcga ttataaatac cctgctgggc atagttcagc    3480
cagcgatggt gaccacagga gttgggccag agagagcaaa agcttcaatg ttctcaagca    3540
gctgctgctc tccgagaact gtgtgcgaga tctgtcccca cacaggagtg actctgtccc    3600
cgacacgaaa aagaaaggac acaaaaacaa cgcgcccggc agcaaacctg aattcggcat    3660
ttcttcttta aatggactga tgtatagttc cccgcagcct ggcagttgtg tgacggatca    3720
taggacattt tcatacccgg gaatggtaaa gacccctctg agccctcctt tcccagagca    3780
cttgggctgt gtggggtcca gaccagaacc tgggcttttg aatggatgtt ccgtgccgg    3840
tgagaaggga cccattaagt gggtcatcgc agatatggat aagaatgaat acgaaaaga    3900
ctctccaaga ctgaccaaaa ctaatccgat cctctattac atgctcccaga agggaggggg    3960
caattctgtt accacacaag aaacccagga caaagacatc tggagggagc ctgcgtcagc    4020
cgagagtctc tcacaggtta cagtcaaaga gagctactt cccgctgcag aaactaaagc    4080
ttctttcttt aatctaagaa gcccgtacaa tagccatatg ggaaataatg cttctcgccc    4140
acacagtaca aatggagaag tgtatggact tctgggaaac gcgctcacca taaaaaaga    4200
gtcagaataa atgtgtaacct gccataccac tttgggtctt tttaaaattt agtcagtatg    4260
aacttgagat ctgtataaat aagagcatga tttgagaaaa gcatggtata actgaaactc    4320
```

```
cttcctttg aaagtattgg tcactggtga tgtttaaata tgcatactaa tttttgctta     4380
acattagatg tcatgaggaa acaattgaac tcgaggttgg ttgtttacta tttctgtatg     4440
catcagataa caactgtgac tagcctacga atgaacctgt ttttataatc gtaaataaga     4500
ggcatacatt aaaatgcaca acttcaccag g                                    4531

<210> SEQ ID NO 8
<211> LENGTH: 1161
<212> TYPE: PRT
<213> ORGANISM: Mus musculus

<400> SEQUENCE: 8

Met Thr His Gly Glu Glu Leu Gly Ser Asp Val His Gln Asp Ser Ile
1               5                   10                  15

Val Leu Thr Tyr Leu Glu Gly Leu Leu Met His Gln Ala Ala Gly Gly
                20                  25                  30

Ser Gly Thr Ala Ile Asn Lys Lys Ser Ala Gly His Lys Glu Glu Asp
            35                  40                  45

Gln Asn Phe Asn Leu Ser Gly Ser Ala Phe Pro Ser Cys Gln Ser Asn
        50                  55                  60

Gly Pro Thr Val Ser Thr Gln Thr Tyr Gln Gly Ser Gly Met Leu His
65                  70                  75                  80

Leu Lys Lys Ala Arg Leu Leu Gln Ser Ser Glu Asp Trp Asn Ala Ala
                85                  90                  95

Lys Arg Lys Arg Leu Ser Asp Ser Ile Val Asn Leu Asn Val Lys Lys
            100                 105                 110

Glu Ala Leu Leu Ala Gly Met Val Asp Ser Val Pro Lys Gly Lys Gln
        115                 120                 125

Asp Ser Thr Leu Leu Ala Ser Leu Leu Gln Ser Phe Ser Ser Arg Leu
    130                 135                 140

Gln Thr Val Ala Leu Ser Gln Gln Ile Arg Gln Ser Leu Lys Glu Gln
145                 150                 155                 160

Gly Tyr Ala Leu Ser His Glu Ser Leu Lys Val Glu Lys Asp Leu Arg
                165                 170                 175

Cys Tyr Gly Val Ala Ser Ser His Leu Lys Thr Leu Leu Lys Lys Ser
            180                 185                 190

Lys Thr Lys Asp Gln Lys Ser Gly Pro Thr Leu Pro Asp Val Thr Pro
        195                 200                 205

Asn Leu Ile Arg Asp Ser Phe Val Glu Ser Ser His Pro Ala Val Gly
    210                 215                 220

Gln Ser Gly Thr Lys Val Met Ser Glu Pro Leu Ser Cys Ala Ala Arg
225                 230                 235                 240

Leu Gln Ala Val Ala Ser Met Val Glu Lys Arg Ala Ser Pro Ala Ala
                245                 250                 255

Ser Pro Lys Pro Ser Val Ala Cys Ser Gln Leu Ala Leu Leu Leu Ser
            260                 265                 270

Ser Glu Ala His Leu Gln Gln Tyr Ser Arg Glu His Ala Leu Lys Thr
        275                 280                 285

Gln Asn Ala His Gln Val Ala Ser Glu Arg Leu Ala Ala Met Ala Arg
    290                 295                 300

Leu Gln Glu Asn Gly Gln Lys Asp Val Gly Ser Gln Leu Ser Lys
305                 310                 315                 320

Gly Val Ser Gly His Leu Asn Gly Gln Ala Arg Ala Leu Pro Ala Ser
                325                 330                 335
```

-continued

```
Lys Leu Val Ala Asn Lys Asn Ala Ala Thr Phe Gln Ser Pro Met
            340                 345                 350
Gly Val Val Pro Ser Ser Pro Lys Asn Thr Ser Tyr Lys Asn Ser Leu
            355                 360                 365
Glu Arg Asn Asn Leu Lys Gln Ala Ala Asn Asn Ser Leu Leu Leu His
    370                 375                 380
Leu Leu Lys Ser Gln Thr Ile Pro Thr Pro Met Asn Gly His Ser Gln
385                 390                 395                 400
Asn Glu Arg Ala Ser Ser Phe Glu Ser Ser Thr Pro Thr Thr Ile Asp
                405                 410                 415
Glu Tyr Ser Asp Asn Asn Pro Ser Phe Thr Asp Ser Ser Gly Asp
            420                 425                 430
Glu Ser Ser Tyr Ser Asn Cys Val Pro Ile Asp Leu Ser Cys Lys His
            435                 440                 445
Arg Ile Glu Lys Pro Glu Ala Glu Arg Pro Val Ser Leu Glu Asn Leu
    450                 455                 460
Thr Gln Ser Leu Leu Asn Thr Trp Asp Pro Lys Ile Pro Gly Val Asp
465                 470                 475                 480
Ile Lys Glu Asp Gln Asp Thr Ser Thr Asn Ser Lys Leu Asn Ser His
                485                 490                 495
Gln Lys Val Thr Leu Leu Gln Leu Leu Leu Gly His Lys Ser Glu Glu
            500                 505                 510
Thr Val Glu Arg Asn Ala Ser Pro Gln Asp Ile His Ser Asp Gly Thr
            515                 520                 525
Lys Phe Ser Pro Gln Asn Tyr Thr Arg Thr Ser Val Ile Glu Ser Pro
    530                 535                 540
Ser Thr Asn Arg Thr Thr Pro Val Ser Thr Pro Pro Leu Tyr Thr Ala
545                 550                 555                 560
Ser Gln Ala Glu Ser Pro Ile Asn Leu Ser Gln His Ser Leu Val Ile
                565                 570                 575
Lys Trp Asn Ser Pro Pro Tyr Ala Cys Ser Thr Pro Ala Ser Lys Leu
            580                 585                 590
Thr Asn Thr Ala Pro Ser His Leu Met Asp Leu Thr Lys Gly Lys Glu
            595                 600                 605
Ser Gln Ala Glu Lys Pro Ala Pro Ser Glu Gly Ala Gln Asn Ser Ala
    610                 615                 620
Thr Phe Ser Ala Ser Lys Leu Leu Gln Asn Leu Ala Gln Cys Gly Leu
625                 630                 635                 640
Gln Ser Ser Gly Pro Gly Glu Glu Gln Arg Pro Cys Lys Gln Leu Leu
                645                 650                 655
Ser Gly Asn Pro Asp Lys Pro Leu Gly Leu Ile Asp Arg Leu Asn Ser
            660                 665                 670
Pro Leu Leu Ser Asn Lys Thr Asn Ala Ala Glu Glu Ser Lys Ala Phe
            675                 680                 685
Ser Ser Gln Pro Ala Gly Pro Glu Pro Gly Leu Pro Gly Cys Glu Ile
    690                 695                 700
Glu Asn Leu Leu Glu Arg Arg Thr Val Leu Gln Leu Leu Leu Gly Asn
705                 710                 715                 720
Ser Ser Lys Gly Lys Asn Glu Lys Glu Lys Thr Pro Ala Arg Asp
                725                 730                 735
Glu Ala Pro Gln Glu His Ser Glu Arg Ala Ala Asn Glu Gln Ile Leu
            740                 745                 750
Met Val Lys Ile Lys Ser Glu Pro Cys Asp Asp Phe Gln Thr His Asn
            755                 760                 765
```

Thr Asn Leu Pro Leu Asn His Asp Ala Lys Ser Ala Pro Phe Leu Gly
770                 775                 780

Val Thr Pro Ala Ile His Arg Ser Thr Ala Ala Leu Pro Val Ser Glu
785                 790                 795                 800

Asp Phe Lys Ser Glu Pro Ala Ser Pro Gln Asp Phe Ser Phe Ser Lys
                805                 810                 815

Asn Gly Leu Leu Ser Arg Leu Leu Arg Gln Asn Gln Glu Ser Tyr Pro
                820                 825                 830

Ala Asp Glu Gln Asp Lys Ser His Arg Asn Ser Glu Leu Pro Thr Leu
                835                 840                 845

Glu Ser Lys Asn Ile Cys Met Val Pro Lys Lys Arg Lys Leu Tyr Thr
850                 855                 860

Glu Pro Leu Glu Asn Pro Phe Lys Lys Met Lys Asn Thr Ala Val Asp
865                 870                 875                 880

Thr Ala Asn His His Ser Gly Pro Glu Val Leu Tyr Gly Ser Leu Leu
                885                 890                 895

His Gln Glu Glu Leu Lys Phe Ser Arg Asn Glu Leu Asp Tyr Lys Tyr
                900                 905                 910

Pro Ala Gly His Ser Ser Ala Ser Asp Gly Asp His Arg Ser Trp Ala
                915                 920                 925

Arg Glu Ser Lys Ser Phe Asn Val Leu Lys Gln Leu Leu Leu Ser Glu
930                 935                 940

Asn Cys Val Arg Asp Leu Ser Pro His Arg Ser Asp Ser Val Pro Asp
945                 950                 955                 960

Thr Lys Lys Lys Gly His Lys Asn Asn Ala Pro Gly Ser Lys Pro Glu
                965                 970                 975

Phe Gly Ile Ser Ser Leu Asn Gly Leu Met Tyr Ser Ser Pro Gln Pro
                980                 985                 990

Gly Ser Cys Val Thr Asp His Arg Thr Phe Ser Tyr Pro Gly Met Val
                995                 1000                1005

Lys Thr Pro Leu Ser Pro Pro Phe Pro Glu His Leu Gly Cys Val Gly
                1010                1015                1020

Ser Arg Pro Glu Pro Gly Leu Leu Asn Gly Cys Ser Val Pro Gly Glu
1025                1030                1035                1040

Lys Gly Pro Ile Lys Trp Val Ile Ala Asp Met Asp Lys Asn Glu Tyr
                1045                1050                1055

Glu Lys Asp Ser Pro Arg Leu Thr Lys Thr Asn Pro Ile Leu Tyr Tyr
                1060                1065                1070

Met Leu Gln Lys Gly Gly Gly Asn Ser Val Thr Thr Gln Glu Thr Gln
                1075                1080                1085

Asp Lys Asp Ile Trp Arg Glu Pro Ala Ser Ala Glu Ser Leu Ser Gln
                1090                1095                1100

Val Thr Val Lys Glu Glu Leu Leu Pro Ala Ala Glu Thr Lys Ala Ser
1105                1110                1115                1120

Phe Phe Asn Leu Arg Ser Pro Tyr Asn Ser His Met Gly Asn Asn Ala
                1125                1130                1135

Ser Arg Pro His Ser Thr Asn Gly Glu Val Tyr Gly Leu Leu Gly Asn
                1140                1145                1150

Ala Leu Thr Ile Lys Lys Glu Ser Glu
                1155                1160

<210> SEQ ID NO 9
<211> LENGTH: 5
<212> TYPE: PRT

```
<213> ORGANISM: Artificial Sequence
<220> FEATURE:
<223> OTHER INFORMATION: Motif
<220> FEATURE:
<221> NAME/KEY: VARIANT
<222> LOCATION: 2, 3
<223> OTHER INFORMATION: Xaa = any amino acid

<400> SEQUENCE: 9

Leu Xaa Xaa Leu Leu
 1               5

<210> SEQ ID NO 10
<211> LENGTH: 5
<212> TYPE: PRT
<213> ORGANISM: Artificial Sequence
<220> FEATURE:
<223> OTHER INFORMATION: Motif
<220> FEATURE:
<221> NAME/KEY: VARIANT
<222> LOCATION: 2
<223> OTHER INFORMATION: Xaa = any amino acid

<400> SEQUENCE: 10

Pro Xaa Asp Leu Ser
 1               5
```